United States Patent
Brands

(10) Patent No.: US 12,115,156 B2
(45) Date of Patent: *Oct. 15, 2024

(54) COMPOSITIONS OF CXCR4 INHIBITORS AND METHODS OF PREPARATION AND USE

(71) Applicant: X4 Pharmaceuticals, Inc., Boston, MA (US)

(72) Inventor: Karel Marie Joseph Brands, Todi (IT)

(73) Assignee: X4 Pharmaceuticals, Inc., Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/312,484

(22) Filed: May 4, 2023

(65) Prior Publication Data

US 2024/0058322 A1    Feb. 22, 2024

Related U.S. Application Data

(63) Continuation of application No. 17/359,391, filed on Jun. 25, 2021, now Pat. No. 11,672,793, which is a continuation of application No. 16/704,302, filed on Dec. 5, 2019, now Pat. No. 11,045,461, which is a continuation of application No. 16/215,963, filed on Dec. 11, 2018, now Pat. No. 10,548,889.

(60) Provisional application No. 62/726,010, filed on Aug. 31, 2018.

(51) Int. Cl.
   *A61K 31/4709*   (2006.01)
   *A61K 9/48*      (2006.01)
   *A61P 35/00*     (2006.01)

(52) U.S. Cl.
   CPC .......... *A61K 31/4709* (2013.01); *A61K 9/485* (2013.01); *A61K 9/4858* (2013.01); *A61K 9/4866* (2013.01); *A61P 35/00* (2018.01)

(58) Field of Classification Search
   CPC .. A61K 31/4709; A61K 9/485; A61K 9/4858; A61K 9/4866; A61P 35/00
   See application file for complete search history.

(56) References Cited

U.S. PATENT DOCUMENTS

| | | | |
|---|---|---|---|
| 4,933,447 A | 6/1990 | Koono et al. |
| 5,021,409 A | 6/1991 | Murrer et al. |
| 5,235,056 A | 8/1993 | Cunkle et al. |
| 5,563,151 A | 10/1996 | Bowles et al. |
| 5,582,823 A | 12/1996 | Souza |
| 5,583,131 A | 12/1996 | Bridger et al. |
| 5,698,546 A | 12/1997 | Bridger et al. |
| 5,817,807 A | 10/1998 | Bridger et al. |
| 5,932,749 A | 8/1999 | Li et al. |
| 6,001,826 A | 12/1999 | Murrer et al. |
| 6,245,799 B1 | 6/2001 | Asselin et al. |
| 6,268,354 B1 | 7/2001 | Nishimura et al. |
| 6,365,583 B1 | 4/2002 | MacFarland et al. |
| 6,506,770 B1 | 1/2003 | Bridger et al. |
| 6,552,065 B2 | 4/2003 | Remiszewski et al. |
| 6,635,278 B1 | 10/2003 | Dahl et al. |
| 6,683,192 B2 | 1/2004 | Baxter et al. |
| 6,734,191 B2 | 5/2004 | Bridger et al. |
| 6,734,194 B2 | 5/2004 | End et al. |
| 6,794,379 B2 | 9/2004 | Medina et al. |
| 6,825,351 B2 | 11/2004 | McEachern et al. |
| 6,835,731 B2 | 12/2004 | Bridger et al. |
| 6,864,265 B2 | 3/2005 | Bridger et al. |
| 6,878,714 B2 | 4/2005 | Askew et al. |
| 6,987,102 B2 | 1/2006 | Bridger et al. |
| 7,053,215 B2 | 5/2006 | Medina et al. |
| 7,071,189 B2 | 7/2006 | Kawashima et al. |
| 7,091,217 B2 | 8/2006 | Bridger et al. |
| 7,135,570 B2 | 11/2006 | McEachern et al. |
| 7,169,750 B2 | 1/2007 | Bridger et al. |
| 7,291,631 B2 | 11/2007 | Bridger et al. |
| 7,332,605 B2 | 2/2008 | Crawford et al. |
| 7,354,932 B2 | 4/2008 | Bridger et al. |
| 7,354,934 B2 | 4/2008 | Bridger et al. |
| 7,390,799 B2 | 6/2008 | Bruncko et al. |
| 7,452,994 B2 | 11/2008 | McEachern et al. |
| 7,491,544 B2 | 2/2009 | Canary et al. |
| 7,501,518 B2 | 3/2009 | Chen et al. |
| 7,550,484 B2 | 6/2009 | Bridger et al. |
| 7,592,351 B2 | 9/2009 | Sundermann et al. |
| 7,723,525 B2 | 5/2010 | Crawford et al. |
| 7,863,293 B2 | 1/2011 | Bridger et al. |
| 7,897,590 B2 | 3/2011 | Bridger et al. |

(Continued)

FOREIGN PATENT DOCUMENTS

| | | |
|---|---|---|
| EP | 0434385 A2 | 6/1991 |
| WO | WO-1997009976 A2 | 3/1997 |

(Continued)

OTHER PUBLICATIONS

"Common Terminology Criteria for Adverse Events (CTCAE), Version 4.0," 2010, commercially available from *U.S. Department of Health and Human Services, National Institutes of Health, National Cancer Institute*, NIH Publication No. 09-5410.

"Nivolumab," commercially available from European Medicines Agency, *Drugbank*, http://www.drugbank.ca/drugs/DB09035.

"Q3C—Tables and Lists, Guidance for Industry," 2018, commercially available from *U.S. Department of Health and Human Services, Food and Drug Adminstration, Center for Drug Evaluation and Research, Center for Biologics Evaluation and Research*, https://www.fda.gov/downloads/Drugs/GuidanceComplianceRegulatoryInformation/Guidances/UCM073395.pdf.

(Continued)

*Primary Examiner* — D Margaret M Seaman
(74) *Attorney, Agent, or Firm* — Dechert LLP; Andrea L. C. Reid; Joseph W. Arico

(57) ABSTRACT

The present invention provides compositions and methods of use for treating, preventing, or ameliorating a disease, disorder, or condition associated with a chemokine receptor such as CXCR4.

18 Claims, 10 Drawing Sheets

(56) References Cited

U.S. PATENT DOCUMENTS

| | | |
|---|---|---|
| 7,935,692 B2 | 5/2011 | Bridger et al. |
| 8,138,347 B2 | 3/2012 | Knight et al. |
| 8,168,783 B2 | 5/2012 | Kokubo et al. |
| 8,178,123 B2 | 5/2012 | Pauletti et al. |
| 8,778,967 B2 | 7/2014 | Bridger et al. |
| 8,889,159 B2 | 11/2014 | Cleary et al. |
| 8,906,682 B2 | 12/2014 | June et al. |
| 9,119,790 B2 | 9/2015 | Crowley et al. |
| 9,155,723 B2 | 10/2015 | Jain et al. |
| 9,267,934 B2 | 2/2016 | Singh et al. |
| 9,314,468 B2 | 4/2016 | Clark et al. |
| 10,548,889 B1* | 2/2020 | Brands ................ A61K 9/4858 |
| 10,610,527 B2 | 4/2020 | Arbeit et al. |
| 11,045,461 B2* | 6/2021 | Brands ................ A61P 35/00 |
| 11,672,793 B2* | 6/2023 | Brands ................ A61P 35/00 |
| | | 546/171 |
| 2003/0220341 A1 | 11/2003 | Bridger et al. |
| 2003/0232808 A1 | 12/2003 | Kobayashi et al. |
| 2005/0227958 A1 | 10/2005 | Wang et al. |
| 2007/0043012 A1 | 2/2007 | Bridger |
| 2007/0123538 A1 | 5/2007 | Dunkle et al. |
| 2007/0167459 A1 | 7/2007 | Habashita et al. |
| 2007/0232615 A1 | 10/2007 | Gudmundsson et al. |
| 2007/0259040 A1 | 11/2007 | Cherukuri |
| 2008/0045537 A1 | 2/2008 | Gudmundsson et al. |
| 2008/0058353 A1 | 3/2008 | Banks |
| 2008/0096861 A1 | 4/2008 | Gudmundsson et al. |
| 2008/0167341 A1 | 7/2008 | Bridger et al. |
| 2008/0171740 A1 | 7/2008 | Gudmundsson et al. |
| 2009/0093454 A1 | 4/2009 | Gudmundsson et al. |
| 2009/0203533 A1 | 8/2009 | Munnes et al. |
| 2009/0247570 A1 | 10/2009 | Mayer |
| 2009/0325877 A1 | 12/2009 | Grunt et al. |
| 2010/0002272 A1 | 1/2010 | Sato et al. |
| 2010/0022724 A1 | 1/2010 | Jacobsen et al. |
| 2010/0028299 A1 | 2/2010 | Einav et al. |
| 2010/0143301 A1 | 6/2010 | Desai et al. |
| 2011/0206607 A1 | 8/2011 | Olsson et al. |
| 2011/0293521 A1 | 12/2011 | Hyde et al. |
| 2012/0041028 A1 | 2/2012 | Cooper et al. |
| 2012/0141471 A1 | 6/2012 | Salvino et al. |
| 2013/0216531 A1 | 8/2013 | Jain et al. |
| 2014/0275260 A1 | 9/2014 | Kawale et al. |
| 2015/0004239 A1 | 1/2015 | Cullen et al. |
| 2015/0030561 A1 | 1/2015 | Dale et al. |
| 2015/0216843 A1 | 8/2015 | Fearon |
| 2015/0246019 A1 | 9/2015 | Bridger et al. |
| 2015/0301058 A1 | 10/2015 | Schettini et al. |
| 2015/0352208 A1 | 12/2015 | Fearon |
| 2016/0089385 A1 | 3/2016 | Sherman et al. |
| 2017/0090658 A1 | 3/2017 | Park et al. |
| 2017/0137401 A1 | 5/2017 | Cox et al. |
| 2017/0166591 A1 | 6/2017 | Ojima et al. |
| 2017/0234879 A1 | 8/2017 | Klinguer-Hamour et al. |
| 2017/0333436 A1 | 11/2017 | Treon et al. |
| 2018/0369167 A1 | 12/2018 | Arbeit et al. |
| 2018/0369229 A1 | 12/2018 | Ragan et al. |
| 2019/0030023 A1 | 1/2019 | Arbeit et al. |
| 2019/0083485 A1 | 3/2019 | Arbeit et al. |
| 2019/0160051 A1 | 5/2019 | Arbeit |
| 2019/0322671 A1 | 10/2019 | Bourque et al. |
| 2020/0123150 A1 | 4/2020 | Bourque et al. |
| 2020/0138804 A1 | 5/2020 | Parasuraman et al. |
| 2020/0253953 A1 | 8/2020 | Brands |
| 2020/0255414 A1 | 8/2020 | Bourque et al. |
| 2020/0268739 A1 | 8/2020 | Arbeit et al. |
| 2021/0025895 A1 | 1/2021 | Wang et al. |
| 2021/0127496 A1 | 4/2021 | Tuominen et al. |

FOREIGN PATENT DOCUMENTS

| | | |
|---|---|---|
| WO | WO-1999004794 A1 | 2/1999 |
| WO | WO-1999031264 A1 | 6/1999 |
| WO | WO-2000002870 A1 | 1/2000 |
| WO | WO-2000022599 A1 | 4/2000 |
| WO | WO-2000045814 A1 | 8/2000 |
| WO | WO-2000056729 A1 | 9/2000 |
| WO | WO-2001042241 A1 | 6/2001 |
| WO | WO-2002022600 A2 | 3/2002 |
| WO | WO-2002034745 A1 | 5/2002 |
| WO | WO-2002076948 A1 | 10/2002 |
| WO | WO-2003011277 A3 | 2/2003 |
| WO | WO-2003055876 A1 | 7/2003 |
| WO | WO-2003063794 A2 | 8/2003 |
| WO | WO-2004019973 A1 | 3/2004 |
| WO | WO-2004089925 A1 | 10/2004 |
| WO | WO-2004093817 A2 | 11/2004 |
| WO | WO-2004106328 A1 | 12/2004 |
| WO | WO-2004106493 A2 | 12/2004 |
| WO | WO-2005007623 A1 | 1/2005 |
| WO | WO-2005113554 A2 | 12/2005 |
| WO | WO-2006026703 A2 | 3/2006 |
| WO | WO-2006036816 A2 | 4/2006 |
| WO | WO-2006078846 A1 | 7/2006 |
| WO | WO-2006096444 A2 | 9/2006 |
| WO | WO-2006122806 A2 | 11/2006 |
| WO | WO-2006138259 A2 | 12/2006 |
| WO | WO-2007008539 A2 | 1/2007 |
| WO | WO-2007016176 A2 | 2/2007 |
| WO | WO-2007022523 A2 | 2/2007 |
| WO | WO-2007027999 A2 | 3/2007 |
| WO | WO-2007044729 A2 | 4/2007 |
| WO | WO-2007053452 A1 | 5/2007 |
| WO | WO-2007070514 A1 | 6/2007 |
| WO | WO-2007084786 A1 | 7/2007 |
| WO | WO-2007087548 A2 | 8/2007 |
| WO | WO-2007129161 A2 | 11/2007 |
| WO | WO-2008039218 A2 | 4/2008 |
| WO | WO-2008109943 A1 | 9/2008 |
| WO | WO-2008118802 A1 | 10/2008 |
| WO | WO-2009026251 A1 | 2/2009 |
| WO | WO-2009114512 A1 | 9/2009 |
| WO | WO-2009117710 | 9/2009 |
| WO | WO-2011090760 A1 | 7/2011 |
| WO | WO-2011147026 A2 | 12/2011 |
| WO | WO-2012049277 A1 | 4/2012 |
| WO | WO-2012075362 A2 | 6/2012 |
| WO | WO-2012094703 A1 | 7/2012 |
| WO | WO-2015030853 A1 | 3/2015 |
| WO | WO-2015038887 A1 | 3/2015 |
| WO | WO-2015069770 A1 | 5/2015 |
| WO | WO-2015143012 A1 | 9/2015 |
| WO | WO-2015200341 A1 | 12/2015 |
| WO | WO-2016008976 A1 | 1/2016 |
| WO | WO-2016090434 A1 | 6/2016 |
| WO | WO-2016146261 A1 | 9/2016 |
| WO | WO-2016201425 A1 | 12/2016 |
| WO | WO-2017048702 A1 | 3/2017 |
| WO | WO-2017106332 A1 | 6/2017 |
| WO | WO-2017112894 A1 | 6/2017 |
| WO | WO-2017127811 A1 | 7/2017 |
| WO | WO-2007087549 A2 | 8/2017 |
| WO | WO-2017177230 A1 | 10/2017 |
| WO | WO-2017181073 A1 | 10/2017 |
| WO | WO-2017223229 A1 | 12/2017 |
| WO | WO-2018237158 A1 | 12/2018 |
| WO | WO-2019094392 A1 | 5/2019 |
| WO | WO-2019126106 A1 | 6/2019 |
| WO | WO-2019200223 A1 | 10/2019 |
| WO | WO-2020047410 A1 | 3/2020 |

OTHER PUBLICATIONS

"Therapeutics," commercially available from *Encyclopedia Britannica Online*, https://www.britannica.com/science/therapeutics.

"WMA Declaration of Helsinki—Ethical Principles for Medical Research Involving Human Subjects," 2013, commercially available from *World Medical Association*, http://www.wma.net/en/30publications/10policies/b3/.

Abi-Younes et al., "The stromal cell-derived factor-1 chemokine is a potent platelet agonist highly expressed in atherosclerotic plaques," Circ Res. 2000;86(2):131-8.

(56) References Cited

OTHER PUBLICATIONS

Acharyya et al., "A CXCL1 paracrine network links cancer chemoresistance and metastasis," Cell. 2012;150(1):165-78.
Aduro Biotech, Inc., "Safety and Efficacy of MIW815 (ADU-S100) +/– Ipilimumab in Patients With Advanced/Metastatic Solid Tumors or Lymphomas," ClinicalTrials.gov: NCT02675439, First Posted: Feb. 5, 2016, Last Update: Sep. 26, 2018, https://clinicaltrials.gov/ct2/show/study/NCT02675439. Date Accessed, Mar. 18, 2019 (6 pages).
Aeglea Biotherapeutics, "A Multiple Dose, Dose Escalation Trial of AEB1102 in Patients With Advanced Solid Tumors," ClinicalTrials.gov: NCT02561234, First Posted: Sep. 28, 2015, Last Update: Mar. 22, 2019, https://clinicaltrials.gov/ct2/show/study/NCT02561234. Date Accessed, Mar. 25, 2019 (6 pages).
Aeglea Biotherapeutics, "A Multiple Dose, Dose Escalation Trial of AEB1102 in Patients With AML or MDS," ClinicalTrials.gov: NCT02732184, First Posted: Apr. 8, 2016, Last Update: Oct. 17, 2018, https://clinicaltrials.gov/ct2/show/study/NCT02732184. Date Accessed, Mar. 25, 2019 (6 pages).
Agenus Inc., "AGEN-1884, an Anti-CTLA-4 Antibody, in Advanced Solid Cancers," ClinicalTrials.gov: NCT02694822, First Posted: Mar. 1, 2016, Last Update: Jun. 27, 2017, https://clinicaltrials.gov/ct2/show/study/NCT02694822. Date Accessed, Mar. 25, 2019 (7 pages).
Aileron Therapeutics, "ALRN-6924 in Patients With Advanced Solid Tumors or Lymphomas," ClinicalTrials.gov: NCT02264613, First Posted: Oct. 15, 2014, Last Update: Jun. 27, 2017, https://clinicaltrials.gov/ct2/show/study/NCT02264613. Date Accessed, Mar. 25, 2019 (7 pages).
Aileron Therapeutics, "Safety Study of ALRN-6924 in Patients With Acute Myeloid Leukemia or Advanced Myelodysplastic Syndrome," ClinicalTrials.gov: NCT02909972, First Posted: Sep. 21, 2016, Last Update: Jun. 27, 2017, https://clinicaltrials.gov/ct2/show/study/NCT02909972. Date Accessed, Mar. 25, 2019 (7 pages).
ALX Oncology Inc., "A Study of ALX148 in Patients With Advanced Solid Tumors and Lymphoma," ClinicalTrials.gov: NCT03013218, First Posted: Jan. 6, 2017, Last Update: Aug. 8, 2018, https://clinicaltrials.gov/ct2/show/study/NCT03013218. Date Accessed, Mar. 18, 2019 (6 pages).
Ami and Ohrui, "Lipase-catalyzed Kinetic Resolution of (±)-trans- and cis-2-Azidocycloalkanols," Biosci Biotechnol Biochem. 1999;63(12):2150-6.
An et al., "Solution phase combinatorial chemistry. Discovery of 13- and 15-membered polyazapyridinocyclophane libraries with antibacterial activity," Tetrahedron. 1998;54(16):3999-4012.
Andtbacka et al., "X4P-001, an Orally Bioavailable CXCR4 Antagonist, Increase T Cell Infiltration in Human Metastatic Melanoma," *The Society for Immunotherapy of Cancer Annual Meeting*, National Harbor, Maryland, Nov. 8-12, 2017 (1 page).
Andtbacka et al., 2018, "X4P-001, and Orally Bioavailable CXCR4 Antagonist, Increases Immune Cell Infiltration and Tumor Inflammatory Status in the Microenvironment of Melanoma," The Society for Immunotherapy of Cancer Annual Meeting, Washington D.C., Nov. 7-11, 2018; Abstract.
AnorMed, "X4P-001 Product Page," 2019, commercially available from *Adis Insight*, http://adisinsight.springer.com/drugs/800017499.
Arenburg et al., "The role of CXC chemokines in the regulation of angiogenesis in non-small cell lung cancer," *Journal of Leukocyte Biology* 1997, 62:554-562.
Auiti et al.,"The Chemokine SDF-1 Is a Chemoattractant for Human CD34+ Hematopoietic Progenitor Cells and Provides a New Mechanism to Explain the Mobilization of CD34+ Progenitors to Peripheral Blood," *Journal of Experimental Medicine* 1997, 185(1):111-120.
Ayers et al., "IFN-y-related mRNA profile predicts clinical response to PD-1 blockade," *The Journal of Clinical Investigation* 2017, 127(8):2930-2940.
Azilji et al., "New Developments in the Treatment of Metastatic Melanoma: Immune Checkpoint Inhibitors and Targeted Therapies," *Anticancer Research*, 2014, 34:1493-1506.

Baggiolini, "Chemokines and leukocyte traffic," *Nature* 1998, 392:565-568.
Balabanian, et al., "Proper desensitization of CXCR4 is required for lymphocyte development and peripheral compartmentalization in mice," *Blood*, 2012, 119(24):5722-5730.
Balabanian, et al., "WHIM syndromes with different genetic anomalies are accounted for by impaired CXCR4 desensitization to CXCL12," *Blood* 2005, 105(6):2449-2457.
Bayer, "Phase I Study of BAY1436032 in IDH1-mutant Advanced Solid Tumors," ClinicalTrials.gov: NCT02746081, First Posted: Apr. 21, 2016, Last Update: Mar. 19, 2019, https://clinicaltrials.gov/ct2/show/study/NCT02746081. Date Accessed, Mar. 25, 2019 (8 pages).
Beaussant-Cohen, et al., 2012, "Description and outcome of a cohort of 8 patients with WHIM syndrome from the French Severe Chronic Neutropenia Registry," *Orphanet Journal of Rare Diseases* 7(71): 5722-5730.
Berge et al., "Pharmaceutical salts," J Pharm Sci. 1977;66(1):1-19.
Blaak et al., "In vivo HIV-1 infection of CD45RA+CD4+ T cells is established primarily by syncytium-inducing variants and correlates with the rate of CD4+ T cell decline," *Proceedings of the National Academy of Sciences of the United States of America*, 2000, 97(3)1269-1274.
Blanchette, S., "NCT02823405: X4P-001 and Prembrolizumab in Patents With Advanced Melanoma (X4P-001-MELA)," Jul. 6, 2016, https://clinicaltrials.gov/ct2/show/NCT02823405> Date Accessed Oct. 5, 2018 (7 pages).
Blanco et al., "The CXCR4 Antagonist AMD3100 Efficiently Inhibits Cell-Surface-Expressed Human Immunodeficiency Virus Type 1 Envelope-Induced Apoptosis," *Antimicrobial Agents and Chemotherapy*, 2000, 44(1)51-56.
Bleul et al., "B Lymphocyte Chemotaxis Regulated in Association with Microanatomic Localization, Differentiation State, and B Cell Receptor Engagement," *Journal of Experimental Medicine*, 1998, 187(5):753-762.
Bohinjec, "Myelokathexis: chronic neutropenia with hyperplastic bone marrow and hypersegmented neutrophils in two siblings," *Blut*, 1981, 42:191-196.
Boutsikou et al., "Tumour necrosis factor, interferon-gamma and interleukins as predictive markers of antiprogrammed cell-death protein-1 treatment in advanced non-small cell lung cancer: a pragmatic approach in clinical practice," *Therapeutic Advances in Medical Oncology*, 2018, 10:1-8.
Bristol-Myers Squibb, "A Phase I Open Label Study of the Safety and Tolerability of Elotuzumab (BMS-901608) Administered in Combination With Either Lirilumab (BMS-986015) or Urelumab (BMS-663513) in Subjects With Multiple Myeloma," ClinicalTrials.gov: NCT02252263, First Posted: Sep. 30, 2014, Last Update: Nov. 1, 2017, https://clinicaltrials.gov/ct2/show/study/NCT02252263. Date Accessed, Mar. 18, 2019 (7 pages).
Bristol-Myers Squibb, "An Investigational Immuno-therapy Study of Experimental Medication BMS-986178 by Itself or in Combination With Nivolumab and/or Ipilimumab in Patients With Solid Cancers That Are Advanced or Have Spread," ClinicalTrials.gov: NCT02737475, First Posted: Apr. 14, 2016, Last Update: Jan. 31, 2019, https://clinicaltrials.gov/ct2/show/study/NCT02737475. Date Accessed, Mar. 18, 2019 (11 pages).
Bristol-Myers Squibb, "An Investigational Immuno-therapy Study of Experimental Medication BMS-986179 Given Alone and in Combination With Nivolumab," ClinicalTrials.gov: NCT02754141, First Posted: Apr. 28, 2016, Last Update: Feb. 1, 2019, https://clinicaltrials.gov/ct2/show/study/NCT02754141. Date Accessed, Mar. 18, 2019 (8 pages).
Bristol-Myers Squibb, "An Investigational Immuno-Therapy Study to Determine the Safety and Effectiveness of Nivolumab and Daratumumab in Patients With Multiple Myeloma," ClinicalTrials.gov: NCT01592370, First Posted: May 7, 2012, Last Update: Jan. 15, 2019, https://clinicaltrials.gov/ct2/show/study/NCT01592370. Date Accessed, Mar. 18, 2019 (9 pages).
Bristol-Myers Squibb, "An Investigational Immuno-therapy Study to Evaluate the Safety and Effectiveness of Experimental Medication BMS-986207 by Itself and in Combination With Nivolumab in Solid Cancers That Are Advanced or Have Spread," ClinicalTrials.

(56) References Cited

OTHER PUBLICATIONS gov: NCT02913313, First Posted: Sep. 23, 2016, Last Update: Jan. 31, 2019, https://clinicaltrials.gov/ct2/show/study/NCT02913313. Date Accessed, Mar. 25, 2019 (9 pages).

Bristol-Myers Squibb, "An Investigational Immuno-therapy Study to Investigate the Safety and Effectiveness of Nivolumab, and Nivolumab Combination Therapy in Virus-associated Tumors (CheckMate358)," ClinicalTrials.gov: NCT02488759, First Posted: Jul. 2, 2015, Last Update: Oct. 19, 2018, https://clinicaltrials.gov/ct2/show/study/NCT02488759. Date Accessed Nov. 29, 2018 (7 pages).

Bristol-Myers Squibb, "Safety and Efficacy Study of Ulocuplumab and Nivolumab in Subjects With Solid Tumors (CXCessoR4)," ClinicalTrials.gov: NCT02472977, First Posted: Jun. 16, 2015, Last Update: Nov. 1, 2018, https://clinicaltrials.gov/ct2/show/study/NCT02472977. Date Accessed, Aug. 20, 2019 (7 pages).

Broxmeyer et al., "Effects of in vivo treatment with PIXY321 (GM-CSF/IL-3 fusion protein) on proliferation kinetics of bone marrow and blood myeloid progenitor cells in patients with sarcoma," Experimental Hematology, 1995, 23:335-340.

Broxmeyer, "A WHIM satisfactorily addressed," *Blood*, 2014, 123(15):2286-2288.

Burger et al., "Chronic Lymphocytic Leukemia B Cells Express Functional CXCR4 Chemokine Receptors That Mediate Spontaneous Migration Beneath Bone Marrow Stromal Cells," *Blood* 1999, 94(11):3658-3667.

Canadian Cancer Trials Group, "Reolysin Combined With Docetaxel and Prednisone or Docetaxel and Prednisone Alone in Metastatic Castration Resistant Prostate Cancer," ClinicalTrials.gov: NCT01619813, First Posted: Jun. 14, 2012, Last Update: Jan. 23, 2019, https://clinicaltrials.gov/ct2/show/study/NCT01619813. Date Accessed, Mar. 25, 2019 (8 pages).

Canadian Cancer Trials Group, "Reolysin in Combination With FOLFOX6 and Bevacizumab or FOLFOX6 and Bevacizumab Alone in Metastatic Colorectal Cancer," ClinicalTrials.gov: NCT01622543 First Posted: Jun. 19, 2012, Last Update: Feb. 1, 2018, https://clinicaltrials.gov/ct2/show/study/NCT01622543. Date Accessed, Mar. 25, 2019 (8 pages).

Cao, et al., "Effect of Low-Dose Ritonavir on the Pharmacokinetics of the CXCR4 Antagonist AMD070 in Healthy Volunteers," Antimicrobial Agents and Chemotherpy, 2008, 52(5):1630-1634.

Catalano et al., "Synthesis of a novel tricyclic 1, 2,3,4, 4a, 5,, 10b-octahydro-1, 10-phenanthroline ring system and CXCR4 antagonists with potent activity against HIV-1," *Bioorganic & Medicinal Chemistry Letters*, 2010, 20:2186-2190.

Celgene, "A Safety and Efficacy Study of Oral AG-120 Plus Subcutaneous Azacitidine and Oral AG-221 Plus Subcutaneous Azacitidine in Subjects With Newly Diagnosed Acute Myeloid Leukemia (AML)," ClinicalTrials.gov: NCT02677922, First Posted: Feb. 9, 2016, Last Update: Feb. 21, 2019, https://clinicaltrials.gov/ct2/show/study/NCT02677922. Date Accessed, Mar. 20, 2019 (11 pages).

Celgene, "A Study of CC-90002 in Subjects With Acute Myeloid Leukemia (AML) and High-risk Myelodysplastic Syndrome (MDS)," ClinicalTrials.gov: NCT02641002, First Posted: Dec. 29, 2015, Last Update: Oct. 18, 2018, https://clinicaltrials.gov/ct2/show/study/NCT02641002. Date Accessed, Mar. 18, 2019 (7 pages).

Celgene, "An Efficacy and Safety Study of AG-221 (CC-90007) Versus Conventional Care Regimens in Older Subjects With Late Stage Acute Myeloid Leukemia Harboring an Isocitrate Dehydrogenase 2 Mutation (IDHENTIFY)," ClinicalTrials.gov: NCT02577406, First Posted: Oct. 16, 2015, Last Update: Feb. 21, 2019, https://clinicaltrials.gov/ct2/show/study/NCT02577406. Date Accessed, Mar. 25, 2019 (12 pages).

Celldex Therapeutics, "A Dose Escalation and Cohort Expansion Study of Anti-CD27 (Varlilumab) and Anti-PD-1 (Nivolumab) in Advanced Refractory Solid Tumors," ClinicalTrials.gov: NCT02335918, First Posted: Jan. 12, 2015, Last Update: Jan. 7, 2019, https://clinicaltrials.gov/ct2/show/study/NCT02335918. Date Accessed, Mar. 18, 2019 (9 pages).

Celldex Therapeutics, "A Study of CDX-1127 (Varlilumab) in Patients With Select Solid Tumor Types or Hematologic Cancers," ClinicalTrials.gov: NCT01460134, First Posted: Oct. 26, 2011, Last Update: Jan. 31, 2018, https://clinicaltrials.gov/ct2/show/study/NCT01460134. Date Accessed, Mar. 18, 2019 (9 pages).

Centre Leon Berard, "Evaluation of Safety and Activity of an Anti-PDL1 Antibody (Durvalumab) Combined With CSF-1R TKI (Pexidartinib) in Patients With Metastatic/Advanced Pancreatic or Colorectal Cancers (Mediplex)," ClinicalTrials.gov: NCT02777710, First Posted: May 19, 2016, Last Update: Jan. 17, 2019, https://clinicaltrials.gov/ct2/show/study/NCT02777710. Date Accessed, Mar. 18, 2019 (10 pages).

Chen et al., 2015, "CXCR4 inhibition in tumor microenvironmental facilitates anti-programmed death receptor-1 immunotherapy in sorafenib-treated hepatocellular carcinoma in mice," *Hepatology* 61(5):1591-1602.

Choueiri et al., "Combination Therapy with the CXCR4 Inhibitor X4P-001 and Nivolumab Demonstrates Preliminary Anti-tumor Activity in RCC Patients that are Unresponsive to Nivolumab Alone," *2018 ESMO Congress*, Munich Germany, Oct. 19-23, 2018 (1 page).

Choueiri et al., 2018, "Combination Therapy with the CXCR4 Inhibitor X4P-001 and Nivolumab Demonstrates Preliminary Anti-tumor Activity in RCC Patients that are Unresponsive to Nivolumab Alone," *2018 ESMO Congress*, Munich Germany, Oct. 19-23, 2018 (1 page).

Choueiri, "Systematic Therapy for Metastatic Renal-Cell Carcinoma," The New England Journal of Medicine, 2017, 376:354-66.

Clark, PE., "Rationale for targeted therapies and potential role of pazopanib in advanced renal cell carcinoma," *Biologics: Targets and Therapy*, 2010, 4:187-197.

Cold Genesys, Inc., "Safety and Efficacy of CG0070 Oncolytic Virus Regimen for High Grade NMIBC After BCG Failure (BOND2)," ClinicalTrials.gov: NCT02365818, First Posted: Feb. 19, 2015, Last Update: Mar. 20, 2019, https://clinicaltrials.gov/ct2/show/study/NCT02365818. Date Accessed, Mar. 25, 2019 (9 pages).

Comba et al., "Catalytic Aziridination of Styrene with Copper Complexes for Substituted 3,7-Diazabicyclo[3.3.1]nonanones," *European Journal of Inorganic Chemistry*, 2003, 9:1711-1718.

Connolly et al., "Complexities of TGF-β Targeted Cancer Therapy," *International Journal of Biological Sciences* 2020, 8(7):964-978.

Connor et al., "Human Immunodeficiency Virus Type 1 Variants with Increased Replicative Capacity Develop during the Asymptomatic Stage before Disease Progression," *Journal of Virology* 1994, 68(7):4400-4408.

Courtney et al.,"Optimizing recent advances in metastatic renal cell carincoma," *Current Onocology Reports*, 2009, 11(3):218-226.

Crawford et al., "AMD070, a CXCR4 Chemokine Receptor Antagonist: Practical Large-Scale Laboratory Synthesis," *Organic Process Research and Development*, 2008, 12(5):823-830.

Crump et al., "Solution structure and basis for functional activity of stromal cell derived factor-1; dissociation of CXCR4 activation from binding and inhibition of HIV-1," *The EMBO Journal*, 1997, 16(23):6996-7007.

D'Alterio, et al., "Inhibition of stromal CXCR4 impairs development of lung metastases," *Cancer Immunology, Immunotherapy* 2012, 61:1713-1720.

Dale et al., Results of a phase 2 trial of an oral CXCR4 antagonist, mavorixafor, for treatment of WHIM syndrome. Blood. Dec. 24, 2020, Epub Aug. 31, 2020, vol. 136, No. 26, pp. 2994-3003.

Dale et al., 1998, "Effects of Granulocyte-Macrophage Colony-Stimulating Factor (GM-CSF) on Neutrophil Kinetics and Function in Normal Human Volunteers," *American Journal of Hematology* 57:7-15.

Dale et al., 2006, "The Severe Chronic Neutropenia International Registry: 10-Year Follow-up Report," *Supportive Cancer Therapy* 3(4):220-231.

Dale et al., 2011, "The CXCR4 antagonist plerixafor is a potential therapy for myelokathexis, WHIM syndrome," *Blood* 118(18):4963-4966.

Dana-Farber Cancer Institute, "LY3022855 With BRAF/MEK Inhibition in Patients With Melanoma," ClinicalTrials.gov: NCT03101254,

(56) References Cited

OTHER PUBLICATIONS

First Posted: Apr. 5, 2017, Last Update: Feb. 4, 2019, https://clinicaltrials.gov/ct2/show/study/NCT03101254. Date Accessed, Mar. 18, 2019 (9 pages).
Debnath et al., 2013, "Small molecule inhibitors of CXCR4," *Theranostics* 3(1):47-75.
DePrimo et al., 2007, "Circulating protein biomarkers of pharmacodynamic activity of sunitinib in patients with metastatic renal cell carcinoma: modulation of VEGF and VEGF-related proteins," *Journal of Translational Medicine* 5(32).
Doranz, 1997, "Chemokine receptors as fusion cofactors for human immunodeficiency virus type 1 (HIV-1)," *Immunologic Research* 16:15-28.
Dorwald, 2005, "Side Reactions in Organic Synthesis," Wiley: VCH, Weinheim, (p. IX of preface and pp. 1-15, 41).
Dotta et al., 2011, "Clinical and genetic features of warts, hypogammaglobulinemia, infections and myelokathexis (WHIM) syndrome," *Current Molecular Medicine* 11:317-325.
Duda et al., 2011, "CXCL12 (SDF1a)-CXCR4/CXCR7 Pathway Inhibition: An Emerging Sensitizer for Anticancer Therapies?," *Clinical Cancer Research* 17(8):2074-2080.
Dudley et al., 2010, "CD8+ Enriched "Young" Tumor Infiltrating Lymphocytes Can Mediate Regression of Metastatic Melanoma," *Clinical Cancer Research* 16(24):6122-6131.
Egberink et al., 1999, "Bicyclams, Selective Antagonists of the Human Chemokine Receptor CXCR4, Potently Inhibit Feline Immunodeficiency Virus Replication," *Journal of Virology* 73(8):6346-6352.
Eli Lilly and Company, "A Study of LY3022855 in Combination With Durvalumab or Tremelimumab in Participants With Advanced Solid Tumors," ClinicalTrials.gov: NCT02718911, First Posted: Mar. 24, 2016, Last Update: Jan. 15, 2019, https://clinicaltrials.gov/ct2/show/study/NCT02718911. Date Accessed, Mar. 18, 2019 (7 pages).
Eli Lilly and Company, "A Study of LY3321367 Alone or With LY3300054 in Participants With Advanced Relapsed/Refractory Solid Tumors," ClinicalTrials.gov: NCT03099109, First Posted: Apr. 4, 2017, Last Update: Mar. 5, 2019, https://clinicaltrials.gov/ct2/show/study/NCT03099109. Date Accessed, Mar. 25, 2019 (10 pages).
EMD Serono Research & Development Institute, Inc., "MSB0011359C (M7824) in Metastatic or Locally Advanced Solid Tumors," ClinicalTrials.gov: NCT02517398, First Posted: Aug. 7, 2015, Last Update: Nov. 19, 2018, https://clinicaltrials.gov/ct2/show/study/NCT02517398. Date Accessed, Mar. 25, 2019 (8 pages).
Facciabene et al., 2011, "Tumour hypoxia promotes tolerance and angiogenesis via CCL28 and Treg cells," *Nature* 475:226-230.
Fedyk et al., 1999, "Maturation decreases responsiveness of human bone marrow B lineage cells to stromal-derived factor 1 (SDF-1)," *Journal of Leukocyte Biology* 66:667-673.
Feig et al., 2013, "Targeting CXCL12 from FAP-expressing carcinoma-associated fibroblasts synergizes with anti-PD-L1 immunotherapy in pancreatic cancer," *PNAS* 110(50):20212-20217.
Finke J. et al., 2011, "MDSC as a mechanism of tumor escape from sunitinib mediated anti-angiogenic therapy," *International Immunopharmacology* 11(7):856-61.
Forty Seven, Inc., "CAMELLIA: Anti-CD47 Antibody Therapy in Haematological Malignancies," ClinicalTrials.gov: NCT02678338, First Posted: Feb. 9, 2016, Last Update: Feb. 21, 2019, https://clinicaltrials.gov/ct2/show/study/NCT02678338. Date Accessed, Mar. 18, 2019 (5 pages).
Forty Seven, Inc., "Trial of Hu5F9-G4 in Combination With Cetuximab in Patients With Solid Tumors and Advanced Colorectal Cancer," ClinicalTrials.gov: NCT02953782, First Posted: Nov. 3, 2016, Last Update: Aug. 1, 2018, https://clinicaltrials.gov/ct2/show/study/NCT02953782. Date Accessed, Mar. 18, 2019 (7 pages).
Forty Seven, Inc., "Trial of Hu5F9-G4 in Combination With Rituximab in Relapsed/Refractory B-cell Non-Hodgkin's Lymphoma," ClinicalTrials.gov: NCT02953509, First Posted: Nov. 2, 2016, Last Update: Feb. 8, 2019, https://clinicaltrials.gov/ct2/show/study/NCT02953509. Date Accessed, Mar. 18, 2019 (8 pages).
Gacche, RN., 2015, "Compensatory angiogenesis and tumor refractoriness," *Oncogenesis* 4(e153).
Gale et al., 1999, "Chemokines: extracellular messengers for all occasions?," *BioEssays* 21:17-28.
Galsky et al., 2014, "A Phase I Trial of LY2510924, a CXCR4 Peptide Antagonist, in Patients with Advanced Cancer," *Clinical Cancer Research* 20(16):3581-3588; 4414.
Gao et al., 2007, "Intratumoral Balance of Regulatory and Cytotoxic T Cells Is Associated With Prognosis of Hepatocellular Carcinoma After Resection," *Journal of Clinical Oncology* 25(18):2586-2593.
Gassenmeier et al., 2013, "CXC Chemokine Receptor 4 is Essential for Maintenance of Renal cell Carcinoma-Initiating Cells and Predicts Metastasis," *Stem Cells Journals*, vol. 31, No. 8, (pp. 1467-1476).
Genelux Corporation, "GL-ONC1 Oncolytic Immunotherapy in Patients With Recurrent or Refractory Ovarian Cancer," ClinicalTrials.gov: NCT02759588, First Posted: May 3, 2016, Last Update: Nov. 8, 2018, https://clinicaltrials.gov/ct2/show/study/NCT02759588. Date Accessed, Mar. 25, 2019 (8 pages).
Genelux GmbH, "A Study of GL-ONC1, an Oncolytic Vaccinia Virus, in Patients With Advanced Peritoneal Carcinomatosis," ClinicalTrials.gov: NCT01443260, First Posted: Sep. 29, 2011, Last Update: Mar. 10, 2015, https://clinicaltrials.gov/ct2/show/study/NCT01443260. Date Accessed, Mar. 25, 2019 (6 pages).
Genzyme, a Sanofi Company, "Safety and Efficacy Study of GC1008 to Treat Renal Cell Carcinoma or Malignant Melanoma," ClinicalTrials.gov: NCT00356460, First Posted: Jul. 26, 2006, Last Update: Mar. 19, 2014, https://clinicaltrials.gov/ct2/show/study/NCT00356460. Date Accessed, Mar. 25, 2019 (10 pages).
Glaspy et al., 1997, "Peripheral Blood Progenitor Cell Mobilization Using Stem Cell Factor in Combination With Filgrastim in Breast Cancer Patients," *Blood* 90:2939-2951.
GlaxoSmithKline, "Dose Escalation and Expansion Study of GSK3359609 in Subjects With Selected Advanced Solid Tumors (INDUCE-1)," ClinicalTrials.gov: NCT02723955, First Posted: Mar. 31, 2016, Last Update: Feb. 25, 2019, https://clinicaltrials.gov/ct2/show/study/NCT02723955. Date Accessed, Mar. 18, 2019 (25 pages).
GlaxoSmithKline, "GSK3174998 Alone or With Pembrolizumab in Subjects With Advanced Solid Tumors (ENGAGE-1)," ClinicalTrials.gov: NCT02528357, First Posted: Aug. 19, 2015, Last Update: Jun. 1, 2018, https://clinicaltrials.gov/ct2/show/study/NCT02528357. Date Accessed, Mar. 18, 2019 (11 pages).
Gonzalo et al., 2000, "Critical Involvement of the Chemotactic Axis CXCR4/Stromal Cell-Derived Factor-1? in the Inflammatory Component of Allergic Airway Disease," Journal of Immunology 165(1):499-508.
Gudmundsson, K.S., 2009, "Amine sustituted N-(1H-benzimidazol-2ylmethyl)-5,6,7,8-tetrahydro-8-quino-linamines as CXCR4 antagonists with potent activity against HIV-1," *Bioorganic & Medicinal Chemistry Letters*.
Gulino et al., 2014, "Altered leukocyte response to CXCL12 in patients with warts hypogammaglobulinemia, infections, myelokathexis (WHIM) syndrome," *Blood* 104(2):444-452.
H. Lee Moffitt Cancer Center and Research Institute, "Combining PD-1 Blockade, CD137 Agonism and Adoptive Cell Therapy for Metastatic Melanoma," ClinicalTrials.gov: NCT02652455, First Posted: Jan. 11, 2016, Last Update: Dec. 4, 2018, https://clinicaltrials.gov/ct2/show/study/NCT02652455. Date Accessed, Mar. 18, 2019 (9 pages).
Hainsworth et al., "A Randomized, Open-Label Phase 2 Study of the CXCR4 Inhibitor LY2510924 in Combination with Sunitinib Versus Sunitinib Alone in Patients with Metastatic Renal Cell Carcinoma," *Target Oncology*, 2016, 11:643-653.
Hamid et al., 2013, "Safety and Tumor Responses with Lambrolizumab (Anti-PD-1) in Melanoma," *New England Journal of Medicine* 369(2):134-144.
Hendrix et al., 2000, "Pharmacokinetics and safety of AMD-3100, a novel antagonist of the CXCR-4 chemokine receptor, in human volunteers," *Antimicrobial Agents and Chemotherapy* 44(6):1667-1673.

(56) References Cited

OTHER PUBLICATIONS

Hendrix, et al., 2004, "Safety, Pharmacokinetics, and Antiviral Activity of AMD3100, a Selective CXCR4 Receptor Inhibitor, in HIV-1 Infection," *Journal of Acquired Immune Deficiency Syndrome* 37(2)1253-1262.

Hernandez et al., 2003, "Mutations in the chemokine receptor gene CXCR4 are associated with WHIM syndrome, a combined immunodeficiency disease," *Nature Genetics* 34(1)70-74.

Hesselgesser et al., 1997, "CD-4-independent association between HIV-1 gp120 and CXCR4: functional chemokine receptors are expressed in human neurons," *Current Biology* 7(2):112-121.

Hesselgesser et al., 1998, "Neuronal apoptosis inducted by HIV-1 gp120 and chemokine SDF-1α is mediated by the chemokine receptor CXCR4," *Current Biology* 8(10):595-598.

Highfill et al., 2014, "Disruption of CXCR2-mediated MDSC tumor trafficking enhances anti-PD1 efficacy," *Science Translational Medicine* 6(237):1-13.

Husain Z. et al., 2013, "Tumor-derived lactate modifies antitumor immune response: Effect on myeloid-derived suppressor cells and NK cells," *Journal of Immunology* 191:1486-95.

Immutep Australia Pty. Ltd., "Phase 1 Study of IMP321 (Eftilagimod Alpha) Adjuvant to Anti-PD-1 Therapy in Unresectable or Metastatic Melanoma (TACTI-mel)," ClinicalTrials.gov: NCT02676869, First Posted: Feb. 8, 2016, Last Update: Jan. 11, 2019, https://clinicaltrials.gov/ct2/show/study/NCT02676869. Date Accessed, Mar. 25, 2019 (6 pages).

Immutep S.A., "IMP321 (Eftilagimod Alpha) as Adjunctive to a Standard Chemotherapy Paclitaxel Metastatic Breast Carcinoma," ClinicalTrials.gov: NCT02614833, First Posted: Nov. 25, 2015, Last Update: Mar. 18, 2019, https://clinicaltrials.gov/ct2/show/study/NCT02614833. Date Accessed, Mar. 25, 2019 (9 pages).

Immutep S.A., "IMP321 Plus First-line Paclitaxel in Metastatic Breast Carcinoma," ClinicalTrials.gov: NCT00349934, First Posted: Jul. 10, 2006, Last Update: Jan. 7, 2010, https://clinicaltrials.gov/ct2/show/study/NCT00349934. Date Accessed, Mar. 25, 2019 (7 pages).

Incyte Biosciences International Sàrl, "An Open-Label, Dose-Escalation, Safety Study of INCAGN01876 in Subjects With Advanced or Metastatic Solid Tumors," ClinicalTrials.gov: NCT02697591, First Posted: Mar. 3, 2016, Last Update: Oct. 31, 2018, https://clinicaltrials.gov/ct2/show/study/NCT02697591. Date Accessed, Mar. 18, 2019 (6 pages).

Incyte Biosciences International Sàrl, "Phase 1/2 Study Exploring the Safety, Tolerability, and Efficacy of INCAGN01876 Combined With Immune Therapies in Advanced or Metastatic Malignancies," ClinicalTrials.gov: NCT03126110, First Posted: Apr. 24, 2017, Last Update: Dec. 10, 2018, https://clinicaltrials.gov/ct2/show/study/NCT03126110. Date Accessed, Mar. 18, 2019 (7 pages).

Innate Pharma, "Combination Study of IPH2201 With Ibrutinib in Patients With Relapsed, Refractory or Previously Untreated Chronic Lymphocytic Leukemia, " ClinicalTrials.gov: NCT02557516, First Posted: Sep. 23, 2015, Last Update: Apr. 24, 2018, https://clinicaltrials.gov/ct2/show/study/NCT02557516. Date Accessed, Mar. 20, 2019 (6 pages).

Innate Pharma, "Efficacy Study of Anti-KIR Monoclonal Antibody as Maintenance Treatment in Acute Myeloid Leukemia (Effikir) (Effikir)," ClinicalTrials.gov: NCT01687387, First Posted: Sep. 18, 2012, Last Update: Feb. 8, 2019, https://clinicaltrials.gov/ct2/show/study/NCT01687387. Date Accessed, Mar. 18, 2019 (9 pages).

Innate Pharma, "Study of IPH4102 in Patients With Relapsed/Refractory Cutaneous T-cell Lymphomas (CTCL)," ClinicalTrials.gov: NCT02593045, First Posted: Oct. 30, 2015, Last Update: Feb. 12, 2019, https://clinicaltrials.gov/ct2/show/study/NCT02593045. Date Accessed, Mar. 18, 2019 (6 pages).

Innate Pharma, "Study of Monalizumab and Cetuximab in Patients With Recurrent or Metastatic Squamous Cell Carcinoma of the Head and Neck," ClinicalTrials.gov: NCT02643550, First Posted: Dec. 31, 2015, Last Update: Sep. 13, 2018, https://clinicaltrials.gov/ct2/show/study/NCT02643550. Date Accessed, Mar. 20, 2019 (9 pages).

Innate Pharma, "Study on the Anti-tumor Activity, Safety and Pharmacology of IPH2101 in Patients With Smoldering Multiple Myeloma (KIRMONO)," ClinicalTrials.gov: NCT01222286, First Posted: Oct. 18, 2010, Last Update: May 9, 2014, https://clinicaltrials.gov/ct2/show/study/NCT01222286. Date Accessed, Mar. 18, 2019 (7 pages).

Innate Pharma, "Study on the Safety, Anti-tumor Activity and Pharmacology of IPH2101 Combined With Lenalidomide in Patients With Multiple Myeloma Experiencing a First or Second Relapse (KIRIMID)," ClinicalTrials.gov: NCT01217203, First Posted: Oct. 8, 2010, Last Update: Feb. 28, 2014, https://clinicaltrials.gov/ct2/show/study/NCT01217203. Date Accessed, Mar. 18, 2019 (7 pages).

International Search Report issued by the United States Patent and Trademark Office as International Searching Authority for International Patent Application No. PCT/US2005/08268, mailed May 26, 2005 (3 pages).

Ishii et al., 1999, "Expression of Stromal Cell-Derived Factor-1/Pre-B Cell Growth-Stimulating Factor Receptor, CXC Chemokine Receptor 4, on CD34+ Human Bone Marrow Cells Is a Phenotypic Alteration for Committed Lymphoid Progenitors," *The Journal of Immunology* 163:3612-3620.

Iwakura et al., 2002, "AMD-3100, a CXCR4 Antagonist, Augments Incorporation of Bone Marrow-Derived Eendothelial Progenitor Cells into Sites of Myocardial Neovascularization," Abstract # 1127, Poster Board #-Session: 2931 , *Blood* 100(11):293A-294A.

Jackson et al., 2011, "Regeneration of ischemic cardiac muscle and vascular endothelium by adult stem cells," *The Journal of Clinical Investigation* 107(1):1395-1402.

Jennerex Biotherapeutics, "A Study of Recombinant Vaccinia Virus to Treat Malignant Melanoma," ClinicalTrials.gov: NCT00429312, First Posted: Jan. 31, 2007, Last Update: Jan. 15, 2015, https://clinicaltrials.gov/ct2/show/study/NCT00429312. Date Accessed, Mar. 25, 2019 (7 pages).

Jounce Therapeutics, Inc., "JTX-2011 Alone and in Combination With Anti-PD-1 or Anti-CTLA-4 in Subjects With Advanced and/or Refractory Solid Tumors (Iconic)," ClinicalTrials.gov: NCT02904226, First Posted: Sep. 16, 2016, Last Update: Jun. 28, 2018, https://clinicaltrials.gov/ct2/show/study/NCT02904226. Date Accessed, Mar. 18, 2019 (11 pages).

Kawai et al., 2005, "Enhanced function with decreased internalization of carboxy-terminus truncated CXCR4 responsible for WHIM syndrome," Experimental Hematology 33:460-468.

Kawai et al., 2007, "WHIM syndrome myelokathexis reproduced in the NOD/SCID mouse xenotransplant model engrafted with healthy human stem cells transduced with C-terminus-truncated CXCR4," *Blood* 109(1):78-84.

Kawai et al., 2009, "WHIM syndrome: congenital immune deficiency disease," *Current Opinion in Hematology* 16(1):20-26.

Kim, et al., 2010, "CXCR4 signaling regulates metastasis of chemoresistant melanoma cells by a lymphatic metastatic niche," *Cancer Research* 70(24):10411-10421.

King, A. G. et al., 2001, "Rapid Mobilization of Murine Hematopoietic Stem Cells With Enhanced Engraftment Properties and Evaluation of Hematopoietic Progenitor Cell Mobilization in Rhesus Monkeys by a Single Injection of SB-251353, a Specific Truncated Form of the Human CXC Chemokine GROI3," *Blood* 97:(6):1534-1542.

Kirkland et al., 1996, "Quantitation of Mafosfamide-Resistant Pre-Colony-Forming Units in Allogeneic Bone Marrow Transplantation: Relationship With Rate of Engraftment and Evidence for Long-Lasting Reduction in Stem Cell Numbers," *Blood* 87(9):3963-69.

Kocher et al., 2001, "Neovascularization of ischemic myocardium by human bone-marrow-derived angioblasts prevents cardiomyocyte apoptosis, reduces remodeling and improves cardiac function," *Nature Medicine* 7:430-436.

Lagane et al., 2008, "CXCR4 dimerization and beta-arrestin-mediated signaling account for the enhanced chemotaxis to CXCL12 in WHIM syndrome," *Blood* 112(1):34-44.

Langan et al., 2012, "Liver Directed Therapy for Renal Cell Carcinoma," *Journal of Cancer* 3:184-190.

(56) References Cited

OTHER PUBLICATIONS

Lapidot et al., 2002, "Current understanding of stem cell mobilization: the roles of chemokines, proteolytic enzymes, adhesion molecules, cytokines, and stromal cells," *Experimental Hematology* 30:973-981.
Lapidot et al., 2002, "The essential roles of the chemokine SDF-1 and its receptor CXCR4 in human stem cell homing and repopulation of transplanted immune-deficient NOD/SCID and NOD/SCID/B2m(null) mice," *Leukemia* 16:1992-2003.
Lataillade et al., 1999, "Chemokine SDF-1 enhances circulating CD341 cell proliferation in synergy with cytokines: possible role in progenitor survival," *Blood* 95(3):756-768.
Leap Therapeutics, Inc., "Phase 1 Open-label Study of TRX518 Monotherapy and TRX518 in Combination With Gemcitabine, Pembrolizumab, or Nivolumab," ClinicalTrials.gov: NCT02628574, First Posted: Dec. 11, 2015, Last Update: Jan. 17, 2018, https://clinicaltrials.gov/ct2/show/study/NCT02628574. Date Accessed, Mar. 18, 2019 (8 pages).
Leap Therapeutics, Inc., "Trial of TRX518 (Anti-GITR mAb) in Stage III or IV Malignant Melanoma or Other Solid Tumors (TRX518-001)," ClinicalTrials.gov: NCT01239134, First Posted: Nov. 11, 2010, Last Update: Aug. 14, 2018, https://clinicaltrials.gov/ct2/show/study/NCT01239134. Date Accessed, Mar. 18, 2019 (8 pages).
Lee et al., 1999, "Coreceptor/Chemokine Receptor Expression on Human Hematopoietic Cells: Biological Implications for Human Immunodeficiency Virus-Type 1 Infection," *Blood* 93(4):1145-1156.
Li, Z. et al., "Design, synthesis, and structure-activity-relationship of a novel series of CXCR4 antagonists," European Journal of Medicinal Chemistry, 2018, 149:30-44.
Liu et al., 1996, "Homozygous defect in HIV-1 coreceptor accounts for resistance of some multiply-exposed individuals to HIV-1 infection," *Cell* 86(3):367-377.
Lord, B. I. et al., 1995, "Mobilization of Early Hematopoietic Progenitor Cells with BB-1001-: A Genetically Engineered Variant of Human Macrophage Inflammatory Protein-1 alpha," *Blood* 85(12):3412-3415.
Ludwig Institute for Cancer Research, "A Phase 1/2 Study of Motolimod (VTX-2337) and MEDI4736 in Subjects With Recurrent, Platinum-Resistant Ovarian Cancer for Whom Pegylated Liposomal Doxorubicin (PLD) is Indicated," ClinicalTrials.gov: NCT02431559, First Posted: May 1, 2015, Last Update: Aug. 7, 2018, https://clinicaltrials.gov/ct2/show/study/NCT02431559. Date Accessed, Mar. 25, 2019 (9 pages).
Ludwig Institute for Cancer Research, "A Phase 1/2 Study to Investigate the Safety, Biologic and Anti-tumor Activity of ONCOS-102 in Combination With Durvalumab in Subjects With Advanced Peritoneal Malignancies," ClinicalTrials.gov: NCT02963831, First Posted: Nov. 15, 2016, Last Update: Mar. 18, 2019, https://clinicaltrials.gov/ct2/show/study/NCT02963831. Date Accessed, Mar. 25, 2019 (8 pages).
Lukacs et al., 2002, "AMD3100, a CxCR4 Antagonist, Attenuates Allergic Lung Inflammation and Airway Hyperreactivity," American Journal of Pathology 16(4):1353-1360.
Lycera Corp., "Study of LYC-55716 in Adult Subjects With Locally Advanced or Metastatic Cancer," ClinicalTrials.gov: NCT02929862, First Posted: Oct. 11, 2016, Last Update: May 7, 2018, https://clinicaltrials.gov/ct2/show/study/NCT02929862. Date Accessed, Mar. 25, 2019 (6 pages).
M.D. Anderson Cancer Center, "Lirilumab and Azacitidine in Treating Patients With Refractory or Relapsed Acute Myeloid Leukemia," ClinicalTrials.gov: NCT02399917, First Posted: Mar. 26, 2015, Last Update: Nov. 30, 2018, https://clinicaltrials.gov/ct2/show/study/NCT02399917. Date Accessed, Mar. 18, 2019 (8 pages).
M.D. Anderson Cancer Center, "Lirilumab and Nivolumab With 5-Azacitidine in Patients With Myelodysplastic Syndromes (MDS)," ClinicalTrials.gov: NCT02599649, First Posted: Nov. 6, 2015, Last Update: Feb. 1, 2019, https://clinicaltrials.gov/ct2/show/study/NCT02599649. Date Accessed, Mar. 18, 2019 (8 pages).
M.D. Anderson Cancer Center, "Lirilumab With Rituximab for Relapsed, Refractory or High-risk Untreated Chronic Lymphocytic Leukemia (CLL) Patients," ClinicalTrials.gov: NCT02481297, First Posted: Jun. 25, 2015, Last Update: Jul. 3, 2018, https://clinicaltrials.gov/ct2/show/study/NCT02481297. Date Accessed, Mar. 18, 2019 (7 pages).
M.D. Anderson Cancer Center, "Nivolumab and HPV-16 Vaccination in Patients With HPV-16 Positive Incurable Solid Tumors," ClinicalTrials.gov: NCT02426892, First Posted: Apr. 27, 2015, Last Update: Aug. 6, 2018, https://clinicaltrials.gov/ct2/show/NCT02426892. Date Accessed Nov. 29, 2018 (8 pages).
Ma et al., 1999, "The chemokine receptor CXCR4 is required for retention of B lineage and granulocytic precursors in the bone marrow microenvironment," *Immunity* 10:463-471.
Maciejweski-Duval et al., 2015, "Altered chemotactic response to CXCL12 in patients carrying GATA2 mutations," *Journal of Leukocyte Biology* 99(6):1065-1076.
Maekawa et al., 2000, "Chemokine/Receptor Dynamics in the Regulation of Hematopoiesis," *Internal Medicine* 39(2):90-100.
Marco et al., "Ligand-guided optimization of CXCR4 homology models for virtual screening using a multiple chemotype approach," Journal of Computer-Aided Molecular Design, 2010, 24:1023-1033.
Matthys et al., 2001, "AMD3100, a potent and specific antagonist of the stromal cell-derived factor-1 chemokine receptor CXCR4, inhibits autoimmune joint inflammation in IFN-gamma receptor-deficient mice," *Journal of Immunology* 167(8):4686-4692.
Maximilian Diehn, "SABR-ATAC: A Trial of TGF-beta Inhibition and Stereotactic Ablative Radiotherapy for Early Stage Non-small Cell Lung Cancer," ClinicalTrials.gov: NCT02581787, First Posted: Oct. 21, 2015, Last Update: Feb. 5, 2019, https://clinicaltrials.gov/ct2/show/study/NCT02581787. Date Accessed, Mar. 25, 2019 (7 pages).
McCormick et al., 2009, "Impaired recruitment of Grk6 and beta-Arrestin 2 causes delayed internalization and desensitization of a WHIM syndrome-associated CXCR4 mutant receptor," *PLoS One* 4:e8102.
McDermott et al., 2010, "Severe congenital neutropenia resulting from G6PC3 deficiency with increased neutrophil CXCR4 expression and myelokathexis," *Blood Journal* 116:2793-2802.
McDermott et al., 2011, "The CXCR4 antagonist plerixafor corrects panleukopenia in patients with WHIM syndrome," *Blood* 118(18):4957-4962.
McDermott et al., 2014, "A phase 1 clinical trial of long-term, low-dose treatment of WHIM syndrome with the CXCR4 antagonist plerixafor," Blood 123(15):2308-2316.
McDermott et al., 2019, "Safety and Efficacy of the Oral CXCR4 Inhibitor X4P-001 + Axitnib in Advanced Renal Cell Carcinoma Patients: An Analysis of Subgroup Responses by Prior Treatment," *ESMO Congress*, Barcelona, Spain, Sep. 30, 2019 (1 page).
McDermott, D., 2018, "Whim Syndrome," *National Organization for Rare Disorders*, 2013, 2016, https://rarediseases.org/rare-diseases/whim-syndrome. Date Accessed Sep. 27, 2019.
MedImmune LLC, "A Phase 1 Study of MEDI0562 in Adult Subjects With Selected Advanced Solid Tumors," ClinicalTrials.gov: NCT02318394, First Posted: Dec. 17, 2014, Last Update: Jan. 29, 2018, https://clinicaltrials.gov/ct2/show/study/NCT02318394. Date Accessed, Mar. 18, 2019 (7 pages).
MedImmune LLC, "A Study in Adult Subjects With Select Advanced Solid Tumors," ClinicalTrials.gov: NCT02583165, First Posted: Oct. 22, 2015, Last Update: Jan. 8, 2019, https://clinicaltrials.gov/ct2/show/study/NCT02583165. Date Accessed, Mar. 18, 2019 (7 pages).
MedImmune LLC, "A Study to Evaluate MEDI0562 in Combination With Immune Therapeutic Agents in Adult Subjects With Advanced Solid Tumors," ClinicalTrials.gov: NCT02705482, First Posted: Mar. 10, 2016, Last Update: Feb. 19, 2019, https://clinicaltrials.gov/ct2/show/study/NCT02705482. Date Accessed, Mar. 18, 2019 (10 pages).
MedImmune LLC, "MEDI9447 Alone and in Combination With MEDI4736 in Adult Subjects With Select Advanced Solid Tumors," ClinicalTrials.gov: NCT02503774, First Posted: Jul. 21, 2015, Last

(56) References Cited

OTHER PUBLICATIONS

Update: Mar. 11, 2019, https://clinicaltrials.gov/ct2/show/study/NCT02503774. Date Accessed, Mar. 18, 2019 (8 pages).
Merck KGaA, Darmstadt, Germany, "MSB0011359C (M7824) in Subjects With Metastatic or Locally Advanced Solid Tumors,"; ClinicalTrials.gov: NCT02699515, First Posted: Mar. 4, 2016, Last Update: Sep. 12, 2018, https://clinicaltrials.gov/ct2/show/study/NCT02699515. Date Accessed, Mar. 25, 2019 (8 pages).
Merck Sharp & Dohme Corp., "Study of MK-1454 Alone or in Combination With Pembrolizumab in Participants With Advanced/Metastatic Solid Tumors or Lymphomas (MK-1454-001)," ClinicalTrials.gov: NCT03010176, First Posted: Jan. 4, 2017, Last Update: Mar. 15, 2019, https://clinicaltrials.gov/ct2/show/study/NCT03010176. Date Accessed, Mar. 18, 2019 (11 pages).
Merck Sharp & Dohme Corp., "Study of MK-4166 and MK-4166 in Combination With Pembrolizumab (MK-3475) in Participants With Advanced Solid Tumors (MK-4166-001)," ClinicalTrials.gov: NCT02132754, First Posted: May 7, 2014, Last Update: Sep. 24, 2018, https://clinicaltrials.gov/ct2/show/study/NCT02132754. Date Accessed, Mar. 18, 2019 (6 pages).
Michael et al., 1998, "Exclusive and Persistent Use of the Entry Coreceptor CXCR4 by Human Immunodeficiency Virus Type 1 from a Subject Homozygous for CCR5 ?32," Journal of Virology 72(7):6040-6047.
Miller, J. et al., 2010, "Novel N-substituted benzimidazole CXCR4 antagonists as potential anti-HIV agents," Bioorganic & Medicinal Chemistry Letters 20:2125-2128.
Miller, J. et al., 2010, "Synthesis and SAR of novel isoquinoline CXCR4 antagonists with potent anti-HIV activity," *Bioorganic & Medicinal Chemistry Letters* 20:3026-3030.
Montane et al., 2011, "Prevention of murine autoimmune diabetes by CCL22-mediated Treg recruitment to pancreatic islets," *Journal of Clinical Investigation* 121(8):3024-3028.
Morimoto et al., "Enhancement of the CXCL12/CXCR4 axis due to acquisition of gemcitabine resistance in pancreatic cancer: effect of CXCR4 antagonists," BMC Cancer. 2016, 16(305):1-13.
Mosi R. M. et al., 2012, "The molecular pharmacology of AMD11070: An orally bioavailable CXCR4 HIV entry inhibitor," *Biochemical Pharmacology* 83:472-479.
Moskovits N. et al., 2006, "p53 attenuates cancer cell migration and invasion through repression of SDF-1/CXCL12 expression in stromal fibroblasts," *Cancer Research* 66(22):10671-10676.
Motzer et al., "Nivolumab for Metastatic Renal Cell Carcinoma: Results of a Randomized Phase II Trial," Journal of Clinical Oncology, vol. 33, No. 13, 2015 (pp. 1430-1437).
Motzer et al., 2015, "Nivolumab for Metastatic Renal Cell Carcinoma: Results of a Randomized Phase II Trial," *Journal of Clinical Oncology* 33(13):1430-1437.
Motzer et al., 2015,"Nivolumab versus Everolimus in Advanced Renal-Cell Carcinoma," *New England Journal of Medicine* 373(19):1803-1813.
Moyle, et al., 2009, "Proof of Activity with AMD11070, an Orally Bioavailable Inhibitor of CXCR4-Tropic HIV Type 1," *Clinical Infectious Diseases* 48:798-805.
Murdoch et al., 2000, "Chemokine receptors and their role in inflammation and infectious diseases," *Blood* 95:3032-3043.
Nagaraj S. et al., 2007, "Altered recognition of antigen is a mechanism of CD8+ T cell tolerance in cancer," *Natural Medicine* 13(7):828-835.
Nagase et al., 2000, "Expression of CXCR4 in Eosinophils: Functional Analyses and Cytokine-Mediated Regulation," *The Journal of Immunology* 164(11):5935-5943.
Nanki et al., 2000, "Cutting Edge: Stromal Cell-Derived Factor-1 Is a Costimulator for CD4+ T Cell Activation," *The Journal of Immunology* 164:5010-5014.
Nash et al., 2003, "Allogeneic HSCT for autoimmune diseases: conventional conditioning regimens," *Bone Marrow Transplantation* 32:S77-S80.
National Cancer Institute (NCI), "A Phase I Study of Intravenous Recombinant Human IL-15 in Adults With Refractory Metastatic Malignant Melanoma and Metastatic Renal Cell Cancer," ClinicalTrials.gov: NCT01021059, First Posted: Nov. 26, 2009, Last Update: Feb. 26, 2019, https://clinicaltrials.gov/ct2/show/study/NCT01021059. Date Accessed, Mar. 20, 2019 (9 pages).
National Cancer Institute (NCI), "Anti-ICOS Monoclonal Antibody MEDI-570 in Treating Patients With Relapsed or Refractory Peripheral T-cell Lymphoma Follicular Variant or Angioimmunoblastic T-cell Lymphoma," ClinicalTrials.gov: NCT02520791, First Posted: Aug. 13, 2015, Last Update: Feb. 6, 2019, https://clinicaltrials.gov/ct2/show/study/NCT02520791. Date Accessed, Mar. 18, 2019 (13 pages).
National Cancer Institute (NCI), "Part 2 of Phase 1 Study of GC1008 to Treat Advanced Melanoma (Part 2 Will Only Accept and Treat Patients With Advanced Malignant Melanoma)," ClinicalTrials.gov: NCT00923169, First Posted: Jun. 18, 2009, Last Update: Mar. 12, 2019, https://clinicaltrials.gov/ct2/show/study/NCT00923169. Date Accessed, Mar. 25, 2019 (8 pages).
National Cancer Institute (NCI), "Subcutaneous Recombinant Human IL-15 (s.c. rhIL-15) and Alemtuzumab for People With Refractory or Relapsed Chronic and Acute Adult T-cell Leukemia (ATL)," ClinicalTrials.gov: NCT02689453, First Posted: Feb. 24, 2016, Last Update: Mar. 20, 2019, https://clinicaltrials.gov/ct2/show/study/NCT02689453. Date Accessed, Mar. 20, 2019 (9 pages).
National Cancer Institute (NCI), "Trametinib and Navitoclax in Treating Patients With Advanced or Metastatic Solid Tumors," ClinicalTrials.gov: NCT02079740, First Posted: Mar. 6, 2014, Last Update: Feb. 6, 2019, https://clinicaltrials.gov/ct2/show/study/NCT02079740. Date Accessed, Mar. 25, 2019 (12 pages).
National Cancer Institute (NCI), "Use of IL-15 After Chemotherapy and Lymphocyte Transfer in Metastatic Melanoma," ClinicalTrials.gov: NCT01369888, First Posted: Jun. 9, 2011, Last Update: Jan. 27, 2015, https://clinicaltrials.gov/ct2/show/study/NCT01369888. Date Accessed, Mar. 20, 2019 (9 pages).
National Cancer Institute, "Nivolumab and Ipilimumab in Treating Patients With HIV Associated Relapsed or Refractory Classical Hodgkin Lymphoma or Solid Tumors That Are Metastatic or Cannot Be Removed by Surgery," ClinicalTrials.gov: NCT02408861, First Posted: Apr. 6, 2016, Last Update: Jun. 12, 2018, https://clinicaltrials.gov/ct2/show/study/NCT02408861. Date Accessed, Nov. 29, 2018 (13 pages).
National Cancer Institute, "Nivolumab in Treating Patients With HTLV-Associated T-Cell Leukemia/Lymphoma," ClinicalTrials.gov: NCT02631746, First Posted: Dec. 16, 2015, Last Update: Aug. 28, 2018, https://clinicaltrials.gov/ct2/show/study/NCT02631746. Date Accessed, Nov. 29, 2018 (9 pages).
Neumedicines Inc., "NM-IL-12 (rHuIL?12) In Relapsed/Refractory Diffuse Large B-Cell Lymphoma (DLBCL) Undergoing Salvage Chemotherapy," ClinicalTrials.gov: NCT02544724, First Posted: Sep. 9, 2015, Last Update: Aug. 3, 2016, https://clinicaltrials.gov/ct2/show/study/NCT02544724. Date Accessed, Mar. 20, 2019 (8 pages).
Neumedicines Inc., "NM-IL-12 in Cutaneous T-Cell Lymphoma (CTCL) Undergoing Total Skin Electron Beam Therapy (TSEBT)," ClinicalTrials.gov: NCT02542124, First Posted: Sep. 4, 2015, Last Update: Nov. 16, 2018, https://clinicaltrials.gov/ct2/show/study/NCT02542124. Date Accessed, Mar. 20, 2019 (8 pages).
Neves, M. et al., 2010, Ligand-guided optimization of CXCR4 homology models for virtual screening using a multiple chemotype approach, *Journal of Computer-Aided Molecular Design* 24(12):1023-1033.
Nicholas Butowski, "A Study of Varlilumab and IMA950 Vaccine Plus Poly-ICLC in Patients With WHO Grade II Low-Grade Glioma (LGG)," ClinicalTrials.gov: NCT02924038, First Posted: Oct. 5, 2016, Last Update: Mar. 6, 2019, https://clinicaltrials.gov/ct2/show/study/NCT02924038. Date Accessed, Mar. 18, 2019 (9 pages).
No author listed, SciFinder Search Results, No month listed, 2015 (39 pages).
No author listed, SciFinder Search Results, No month listed, 2015 (9 pages).
Novartis Pharmaceuticals, "A Phase I/Ib Study of NIZ985 in Combination With PDR001 in Adults With Metastatic Cancers," ClinicalTrials.gov: NCT02452268, First Posted: May 22, 2015, Last

(56) References Cited

OTHER PUBLICATIONS

Update: Oct. 2, 2018, https://clinicaltrials.gov/ct2/show/study/NCT02452268. Date Accessed, Mar. 20, 2019 (7 pages).
Novartis Pharmaceuticals, "Phase I/Ib Study of GWN323 Alone and in Combination With PDR001 in Patients With Advanced Malignancies and Lymphomas," ClinicalTrials.gov: NCT02740270, First Posted: Apr. 15, 2016, Last Update: Feb. 18, 2019, https://clinicaltrials.gov/ct2/show/study/NCT02740270. Date Accessed, Mar. 28, 2019 (6 pages).
Novartis Pharmaceuticals, "Phase I/Ib Study of NIS793 in Combination With PDR001 in Patients With Advanced Malignancies.," ClinicalTrials.gov: NCT02947165, First Posted: Oct. 27, 2016, Last Update: Nov. 6, 2018, https://clinicaltrials.gov/ct2/show/study/NCT02947165. Date Accessed, Mar. 25, 2019 (9 pages).
Novartis Pharmaceuticals, "Phase I/II Study of BLZ945 Single Agent or BLZ945 in Combination With PDR001 in Advanced Solid Tumors," ClinicalTrials.gov: NCT02829723, First Posted: Jul. 12, 2016, Last Update: Jul. 12, 2018, https://clinicaltrials.gov/ct2/show/study/NCT02829723. Date Accessed, Mar. 18, 2019 (7 pages).
Novartis Pharmaceuticals, "Safety and Efficacy of MBG453 as Single Agent and in Combination With PDR001 in Patients With Advanced Malignancies," ClinicalTrials.gov: NCT02608268, First Posted: Nov. 18, 2015, Last Update: Oct. 2, 2018, https://clinicaltrials.gov/ct2/show/study/NCT02608268. Date Accessed, Mar. 25, 2019 (10 pages).
Novartis Pharmaceuticals, "Study of the Safety and Efficacy of MIW815 With PDR001 to Patients With Advanced/Metastatic Solid Tumors or Lymphomas," ClinicalTrials.gov: NCT03172936, First Posted: Jun. 1, 2017, Last Update: Feb. 18, 2019, https://clinicaltrials.gov/ct2/show/study/NCT03172936. Date Accessed, Mar. 18, 2019 (9 pages).
Nyunt, et al., 2008, "Pharmacokinetic Effect of AMD070, an Oral CXCR4 Antagonist, on CYP3A4 and CYP2D6 Substrates Midazolam and Dextromethorphan in Healthy Volunteers," *Journal of Acquired Immune Deficiency Syndrome* 47:559-565.
O'Boyle et al., 2013, "Inhibition of CXCR4-CXCL12 chemotaxis in melanoma by AMD11070," British Journal of Cancer 108(8):1634-1640.
O'Hagen et al., 1999, "Apoptosis Induced by Infection of Primary Brian Cultures with Diverse Human Immunodeficiency Virus Type 1 Isolates: Evidence for a Role of the Envelope," *Journal of Virology* 73(2):897-906.
Okazaki, T. et al., 2013, "A rheostat for immune responses: the unique properties of PD1 and their advantages for clinical application," *Nature Immunology* 14(12):1212-1218.
Oncolytics Biotech, "A Study of REOLYSIN® in Combination With Gemcitabine in Patients With Advanced Pancreatic Adenocarcinoma," ClinicalTrials.gov: NCT00998322, First Posted: Oct. 20, 2009, Last Update: Apr. 10, 2015, https://clinicaltrials.gov/ct2/show/study/NCT00998322. Date Accessed, Mar. 25, 2019 (6 pages).
Oncolytics Biotech, "Efficacy Study of REOLYSIN® in Combination With Paclitaxel and Carboplatin in Platinum-Refractory Head and Neck Cancers," ClinicalTrials.gov: NCT01166542, First Posted: Jul. 21, 2010, Last Update: Nov. 5, 2014, https://clinicaltrials.gov/ct2/show/study/NCT01166542. Date Accessed, Mar. 25, 2019 (7 pages).
Oncolytics Biotech, "Phase 2 Study of REOLYSIN® in Combination With Paclitaxel and Carboplatin for Non-Small Cell Lung Cancer With KRAS or EGFR Activation," ClinicalTrials.gov: NCT00861627, First Posted: Mar. 13, 2009, Last Update: Dec. 2, 2015, https://clinicaltrials.gov/ct2/show/study/NCT00861627. Date Accessed, Mar. 25, 2019 (7 pages).
OncoMed Pharmaceuticals, Inc., "A Study of OMP-313M32 in Subjects With Locally Advanced or Metastatic Solid Tumors," ClinicalTrials.gov: NCT03119428, First Posted: Apr. 18, 2017, Last Update: Dec. 7, 2018, https://clinicaltrials.gov/ct2/show/study/NCT03119428. Date Accessed, Mar. 25, 2019 (7 pages).

Panka et al., 2016, "MDSC trafficking and function in RCC by CXCR4 in the presence of a VEGF-R antagonist is dependent on HIF-2α expression," *European Journal of Cancer*, 69(Supp 1): 146 (1 page).
Panka, DJ. et al., 2013, "HDM2 antagonism delays the development of sunitinib resistance in RCC xenografts: Effects of MI-319 on sunitinib-induced p53 activation, SDF-1 induction, and tumor infiltration by CD11b+/Gr-1+ myeloid suppressor cells," Molecular Cancer 12(17):1-12.
Parameswaran et al., 2011, "Combination of drug therapy in acute lymphblastic leukemia with CXCR4 antagonist," Leukemia 25(8):1314-1323.
PCT International Preliminary Examination Report from PCT/US2002/041407 dated Aug. 1, 2003.
PCT International Preliminary Report on Patentability from PCT/US2004/015977 dated May 2, 2006.
PCT International Search Report and Written Opinion from PCT/US2016/066634 dated Feb. 16, 2017.
PCT International Search Report and Written Opinion from PCT/US2016/066639 dated Feb. 16, 2017.
PCT International Search Report and Written Opinion from PCT/US2016/068394 dated Mar. 3, 2017.
PCT International Search Report and Written Opinion from PCT/US2017/014578 dated Apr. 4, 2017.
PCT International Search Report and Written Opinion from PCT/US2017/026819 dated Jul. 21, 2017.
PCT International Search Report and Written Opinion from PCT/US2018/038776 dated Nov. 20, 2018.
PCT International Search Report and Written Opinion from PCT/US2018/059482 dated Jan. 17, 2019.
PCT International Search Report and Written Opinion from PCT/US2018/066141 dated Mar. 8, 2019.
PCT International Search Report and Written Opinion from PCT/US2019/027169 dated Jul. 3, 2019.
PCT International Search Report and Written Opinion from PCT/US2019/049065 dated Nov. 15, 2019.
PCT International Search Report and Written Opinion from PCT/US2020/066099 dated Mar. 23, 2021.
PCT International Search Report and Written Opinion from PCT/US2021/021713 dated May 18, 2021.
PCT International Search Report from PCT/US05/34491 dated Apr. 11, 2006.
PCT International Search Report from PCT/US05/34950 dated Oct. 4, 2006.
PCT International Search Report from PCT/US2002/029372 dated Aug. 10, 2004.
PCT International Search Report from PCT/US2004/011328 dated Oct. 20, 2004.
PCT International Search Report from PCT/US2004/012627 dated Jan. 13, 2005.
PCT International Search Report from PCT/US2004/015977 dated Jul. 15, 2005.
PCT International Search Report from PCT/US2005/08268 dated May 26, 2005.
Peled et al., 2000, "The chemokine SDF-1 activates the integrins LFA-1, VLA-4, and VLA-5 on immature human CD34(+) cells: role in transendothelial/stromal migration and engraftment of NOD/SCID mice," *Blood* 95(11):3289-3296.
Pfizer, "A Study Of Avelumab In Combination With Other Cancer Immunotherapies In Advanced Malignancies (JAVELIN Medley)," ClinicalTrials.gov: NCT02554812, First Posted: Sep. 18, 2015, Last Update: Mar. 13, 2019, https://clinicaltrials.gov/ct2/show/study/NCT02554812. Date Accessed, Mar. 18, 2019 (13 pages).
Pfizer, "Avelumab In Combination Regimens That Include An Immune Agonist, Epigenetic Modulator, CD20 Antagonist and/or Conventional Chemotherapy in Patients With Relapsed or Refractory Diffuse Large B-cell Lymphoma (R/R DLBCL) (Javelin DLBCL)," ClinicalTrials.gov: NCT02951156, First Posted: Nov. 1, 2016, Last Update: Jan. 29, 2019, https://clinicaltrials.gov/ct2/show/study/NCT02951156. Date Accessed, Mar. 18, 2019 (11 pages).
Pike et al., 1984, "A Cell Renewal System," Nutrition: An Integrated Approach, Third Edition, John Wiley & Sons: 538-539.

(56) References Cited

OTHER PUBLICATIONS

Plexxikon, "A Combination Clinical Study of PLX3397 and Pembrolizumab To Treat Advanced Melanoma and Other Solid Tumors," ClinicalTrials.gov: NCT02452424, First Posted: May 22, 2015, Last Update: Nov. 15, 2018, https://clinicaltrials.gov/ct2/show/study/NCT02452424. Date Accessed, Mar. 18, 2019 (9 pages).
Ponath et al., 1998, "Chemokine receptor antagonists: novel therapeutics for inflammation and AIDS," *Expert Opinion on Investigational Drugs* 7(1):1-18.
Portella et al., Preclinical Development of a Novel Class of CXCR4 Antagonist Impairing Solid Tumors Growth and Metastases, PLOS One, 2013, 8(9):1-9.
Providence Health & Services, "Anti-OX40 Antibody (MEDI6469) in Patients With Metastatic Colorectal Cancer," ClinicalTrials.gov: NCT02559024, First Posted: Sep. 24, 2015, Last Update: Oct. 10, 2018, https://clinicaltrials.gov/ct2/show/study/NCT02559024. Date Accessed, Mar. 18, 2019 (6 pages).
Providence Health & Services, "Anti-OX40 Antibody in Head and Neck Cancer Patients," ClinicalTrials.gov: NCT02274155, First Posted: Oct. 24, 2014, Last Update: Nov. 26, 2018, https://clinicaltrials.gov/ct2/show/study/NCT02274155. Date Accessed, Mar. 18, 2019 (6 pages).
Providence Health & Services, "Anti-OX40, Cyclophosphamide (CTX) and Radiation in Patients With Progressive Metastatic Prostate Cancer," ClinicalTrials.gov: NCT01303705, First Posted: Feb. 25, 2011, Last Update: Aug. 29, 2018, https://clinicaltrials.gov/ct2/show/study/NCT01303705. Date Accessed, Mar. 18, 2019 (10 pages).
Providence Health & Services, "Stereotactic Body Radiation and Monoclonal Antibody to OX40 (MEDI6469) in Breast Cancer Patients With Metastatic Lesions (OX40 Breast)," ClinicalTrials.gov: NCT01862900, First Posted: May 27, 2013, Last Update: Mar. 6, 2019, https://clinicaltrials.gov/ct2/show/study/NCT01862900. Date Accessed, Mar. 18, 2019 (7 pages).
PsiOxus Therapeutics Ltd, "Phase I / Dose Expansion Study of Enadenotucirev in Ovarian Cancer Patients (OCTAVE)," ClinicalTrials.gov: NCT02028117, First Posted: Jan. 6, 2014, Last Update: Feb. 26, 2019, https://clinicaltrials.gov/ct2/show/study/NCT02028117. Date Accessed, Mar. 25, 2019 (8 pages).
PsiOxus Therapeutics Ltd, "Phase I Study of Enadenotucirev and PD-1 Inhibitor in Subjects With Metastatic or Advanced Epithelial Tumors (SPICE)," ClinicalTrials.gov: PsiOxus Therapeutics Ltd, First Posted: Dec. 21, 2015, Last Update: Mar. 4, 2019, https://clinicaltrials.gov/ct2/show/study/NCT02636036. Date Accessed, Mar. 25, 2019 (9 pages).
PubChem Open Chemistry Database, Compound Summary for CID 10890081, created Oct. 25, 2006 (14 pages).
PubChem Open Chemistry Database, Compound Summary for CID 12087079, created Feb. 7, 2007 (14 pages).
PubChem Open Chemistry Database, Compound Summary for CID 19046926, created Dec. 4, 2017 (11 pages).
PubChem Open Chemistry Database, Compound Summary for CID 70962830, created Mar. 21, 2013 (12 pages).
PubChem Open Chemistry Database, Compound Summary for SID 219642471, created Oct. 21, 2014 (12 pages).
Raman et al., 2015, "Immunotherapy in Metastatic Renal Cell Carcinoma: A Comprehensive Review," Biomed Research International 2015:1-9.
Rana et al., 1997, "Role of CCR5 in infection of primary macrophages and lymphocytes by macrophage-tropic strains of human immunodeficiency virus: resistance to patient-derived and prototype isolates resulting from the delta ccr5 mutation," Journal of Virology 71(4):3219-3227.
Ratajczak, et al., 2006, "The pleotropic effects of the SDF-1-CXCR4 axis in organogenesis, regeneration, and tumorigenesis," *Leukemia* 20:1915-1924.
Reagen-Shaw et al., 2007, "Dose translation from animal to human studies revisited," *The FASEB Journal* 22:659-661.
Reetz et al., 1994, "Highly Efficient Lipase-Catalyzed Kinetic Resolution of Chiral Amines" *Chimia International Journal for Chemistry* 48(12):570.

Regeneron Pharmaceuticals, "An Exploratory Tumor Biopsy-driven Study to Understand the Relationship Between Biomarkers and Clinical Response in Melanoma Patients Receiving REGN2810 (Anti-PD-1)," ClinicalTrials.gov: NCT03002376, First Posted: Dec. 23, 2016, Last Update: Jan. 11, 2019, https://clinicaltrials.gov/ct2/show/study/NCT03002376. Date Accessed, Mar. 25, 2019 (6 pages).
Regeneron Pharmaceuticals, "PD-1 in Patients With Advanced Basal Cell Carcinoma Who Experienced Progression of Disease on Hedgehog Pathway Inhibitor Therapy, or Were Intolerant of Prior Hedgehog Pathway Inhibitor Therapy," ClinicalTrials.gov: NCT03132636, First Posted: Apr. 28, 2017, Last Update: Oct. 2, 2018, https://clinicaltrials.gov/ct2/show/study/NCT03132636. Date Accessed, Mar. 25, 2019 (6 pages).
Regeneron Pharmaceuticals, "Study of REGN 2810 Compared to Platinum-Based Chemotherapies in Participants With Metastatic Non-Small Cell Lung Cancer (NSCLC)," ClinicalTrials.gov: NCT03088540, First Posted: Mar. 23, 2017, Last Update: Nov. 5, 2018, https://clinicaltrials.gov/ct2/show/study/NCT03088540. Date Accessed, Mar. 25, 2019 (9 pages).
Regeneron Pharmaceuticals, "Study of REGN2810 and REGN1979 in Patients With Lymphoma," ClinicalTrials.gov: NCT02651662, First Posted: Jan. 11, 2016, Last Update: Sep. 11, 2018, https://clinicaltrials.gov/ct2/show/study/NCT02651662. Date Accessed, Mar. 25, 2019 (7 pages).
Regeneron Pharmaceuticals, "Study of REGN2810 in Patients With Advanced Cutaneous Squamous Cell Carcinoma," ClinicalTrials.gov: NCT02760498, First Posted: May 3, 2016, Last Update: Jan. 14, 2019, https://clinicaltrials.gov/ct2/show/study/NCT02760498. Date Accessed, Mar. 25, 2019 (6 pages).
Regeneron Pharmaceuticals, "Study of REGN3767 (Anti-LAG-3) With or Without REGN2810 (Anti-PD1) in Advanced Cancers," ClinicalTrials.gov: NCT03005782, First Posted: Dec. 29, 2016, Last Update: Jun. 18, 2018, https://clinicaltrials.gov/ct2/show/study/NCT03005782. Date Accessed, Mar. 25, 2019 (7 pages).
Righi E. et al., 2011, "CXCL12/CXCR4 Blockade Induces Multimodal Antitumor Effects That Prolong Survival in an Immunocompetent Mouse Model of Ovarian Cancer," *Cancer Research* 71(16):5522-5534.
Rini et al., 2011, "Comparative effectiveness of axitinib versus soragenib in advanced renal cell carcinoma (AXIS): a randomised phase 3 trial," Lancet 378:1931-1939.
Robert Lowsky, "A Phase I/II Study of Intratumoral Injection of SD-101," ClinicalTrials.gov: NCT02254772, First Posted: Oct. 2, 2014, Last Update: Sep. 29, 2017, https://clinicaltrials.gov/ct2/show/study/NCT02254772. Date Accessed, Mar. 25, 2019 (9 pages).
Robert, et al., 2015, "Pembrolizumab versus Ipilimumab in Advanced Melanoma," *New England Journal of Medicine* 372:2521-2532.
Salcedo et al., 1999, "Vascular endothelial growth factor and basic fibroblast growth factor induce expression of CXCR4 on human endothelial cells: In vivo neovascularization induced by stromal-derived factor-1 alpha.Am," The American Journal of Pathology 154(4):1125-1135.
Saxena et al., 2017, "Efficacy and Mechanism of Action of CXCR4 Inhibition in B16 OVA Melanoma Model," *The Society for Immunotherapy of Cancer Annual Meeting*, National Harbor, Maryland, Nov. 8-12.
Saxena et al., 2017, "Efficacy and Mechanism of Action of CXCR4 Inhibition in B16-OVA Melanoma Model," *Journal for ImmunoTherapy of Cancer*, Abstract 5(Suppl. 2):356.
Scala S., 2015, "Molecular Pathways: Targeting the CXCR4-CXCL12 Axis—Untapped Potential in the Tumor Microenvironment," *Clinical Cancer Research* 21(19):4278-4285.
Scala, et al., 2005, "Expression of CXCR4 predicts poor prognosis in patients with malignant melanoma," *Clinical Cancer Research* 11:1835-1841.
Schlabach et al., 2008, "Cancer proliferation gene discovery through functional genomics," *Science* 319(5863):620-624.
Schols et al., 1997, "Bicyclams, a class of potent anti-HIV agents, are targeted at the HIV coreceptor for Fusin/CXCR-4," *Antiviral Research* 35:147-156.
Schols et al., 1997, "Inhibition of T-tropic HIV Strains by Selective Antagonization of the Chemokine Receptor CXCR4J," *Journal of Experimental Medicine* 186(8):1383-1388.

(56) References Cited

OTHER PUBLICATIONS

Schramm et al., 2000, "Cytopathicity of Human Immunodeficiency Virus Type 2 (HIV-2) in Human Lymphoid Tissue Is Coreceptor Dependent and Comparable to That of HIV-1," *Journal of Virology* 74(20):184-192.
Schuitemaker et al., 1992, "Biological phenotype of human immunodeficiency virus type 1 clones at different stages of infection: progression of disease is associated with a shift from monocytotropic to T-cell-tropic virus population," *Journal of Virology* 66(3):1354-1360.
Sharma, P. et al., 2017, "Primary, Adaptive, and Acquired Resistance to Cancer Immunotherapy," *Cell* 168(4):707-723.
Shen et al., 2013, "CXCR4-mediated STAT3 activation is essential for CXCL12-induced invasion in bladder cancer," *Tumour Biology* 34:1839-45.
Shojaei F. et al., 2007, "Tumor refractoriness to anti-VEGF treatment is mediated by CD11b+Gr1+ myeloid cells," Nature Biotechnology 25(8):911-920.
Sidney Kimmel Comprehensive Cancer Center at Johns Hopkins, "Anti-LAG-3 Alone & in Combination w/ Nivolumab Treating Patients w/ Recurrent GBM (Anti-CD137 Arm Closed Oct. 16, 2018)," ClinicalTrials.gov: NCT02658981, First Posted: Jan. 20, 2016, Last Update: Feb. 11, 2019, https://clinicaltrials.gov/ct2/show/study/NCT02658981. Date Accessed, Mar. 18, 2019 (13 pages).
Sidney Kimmel Comprehensive Cancer Center at Johns Hopkins, "Pilot Study With CY, Pembrolizumab, GVAX, and IMC-CS4 (LY3022855) in Patients With Borderline Resectable Adenocarcinoma of the Pancreas," ClinicalTrials.gov: NCT03153410, First Posted: May 15, 2017, Last Update: Mar. 19, 2019, https://clinicaltrials.gov/ct2/show/study/NCT03153410. Date Accessed, Mar. 18, 2019 (8 pages).
Sillajen, Inc., "Hepatocellular Carcinoma Study Comparing Vaccinia Virus Based Immunotherapy Plus Sorafenib vs Sorafenib Alone (PHOCUS)," ClinicalTrials.gov: NCT02562755, First Posted: Sep. 29, 2015, Last Update: Feb. 6, 2019, https://clinicaltrials.gov/ct2/show/study/NCT02562755. Date Accessed, Mar. 25, 2019 (7 pages).
Silva et al., 2008, "Profiling essential genes in human mammary cells by multiplex RNA1 screening," Science 319:617-20.
Simmons et al., 1996, "Primary, syncytium-inducing human immunodeficiency virus type 1 isolates are dual-tropic and most can use either Lestr or CCR5 as coreceptors for virus entry," *Journal of Virolology* 70(12):8355-8360.
Simmons et al., 1998, "CXCR4 as a Functional Coreceptor for Human Immunodeficiency Virus Type 1 Infection of Primary Macrophages," Journal of Virology 72(10):8453-8457.
SK Chemicals Co., Ltd., "Study to Evaluate SID 530 Compared to Taxotere," ClinicalTrials.gov: NCT00931008, First Posted: Jul. 2, 2009, Last Update: Jan. 24, 2013, https://clinicaltrials.gov/ct2/show/study/NCT00931008. Date Accessed, Mar. 25, 2019 (6 pages).
Skerlj R. et al., 2010, "Discovery of Novel Small Molecule Orally Bioavailable C-X-C Chemokine Receptor 4 Antagonists That Are Potent Inhibitors of T-Tropic (X4) HIV-1 Replication," *Journal of Medicinal Chemistry* 53(8):3376-3388.
Stone, et al., 2007, "Multiple-Dose Escalation Study of the Safety, Pharmacokinetics, and Biologic Activity of Oral AMD070, a Selective CXCR4 Receptor Inhibitor, in Human Subjects.," Antimicrobial Agents and Chemotherapy 51(7):2351-2358.
Sullivan et al., 2015, "Pembrolizumab for Treatment of Patients with Advanced or Unresectable Melanoma," *Clincal Cancer Research* 12(13):2892-2897.
Supplementary European Search Report from European Patent App. No. 04752905.2 dated Mar. 12, 2010.
Supplementary European Search Report from European Patent App. No. 02775823.4, dated Dec. 23, 2004.
Supplementary European Search Report from European Patent App. No. 02805977.2 dated Apr. 16, 2008.
Supplementary European Search Report from European Patent App. No. 04814091.7 dated Mar. 10, 2008.
Supplementary European Search Report from European Patent App. No.04760161.2 dated Jun. 10, 2008.
Syndax Pharmaceuticals, "A Phase 2 Multi-Center Study of Entinostat (SNDX-275) in Patient With Relapsed or Refractory Hodgkin's Lymphoma," ClinicalTrials.gov: NCT00866333, First Posted: Mar. 20, 2009, Last Update: Jul. 1, 2016, https://clinicaltrials.gov/ct2/show/study/NCT00866333. Date Accessed, Mar. 20, 2019 (6 pages).
Targovax Oy, "A Pilot Study of Sequential ONCOS-102, an Engineered Oncolytic Adenovirus Expressing GMCSF, and Pembrolizumab in Patients With Advanced or Unresectable Melanoma Progressing After Programmed Cell Death Protein 1 (PD1) Blockade," ClinicalTrials. gov: NCT03003676, First Posted: Dec. 28, 2016, Last Update: Oct. 25, 2018, https://clinicaltrials.gov/ct2/show/study/NCT03003676. Date Accessed, Mar. 25, 2019 (8 pages).
Tarhini, et al., 2014, "Immune Monitoring of the Circulation and the Tumor Microenvironment in Patients with Regionally Advanced Melanoma Receiving Neoadjuvant Ipilimumab," *PLoS One* 9(2):e87705.
Teasdale et al., 2013, "Risk Assessment of Genotoxic Impurities in New Chemical Entities: Strategies To Demonstrate Control," *Organic Process Research and Development* 17:221-230.
Tersmette et al., 1988, "Differential Syncytium-Inducing Capacity of Human Immunodeficiency Virus Isolates: Frequent Detection of Syncytium-Inducing Isolates in Patients with Aquired Immune Deficiency Syndrome (AIDS) and AIDS-Related Complex," *Journal of Virology* 62(6):2026-2032.
Tesaro, Inc., "A Phase 1 Study of TSR-022, an Anti-TIM-3 Monoclonal Antibody, in Patients With Advanced Solid Tumors (AMBER)," ClinicalTrials.gov: NCT02817633, First Posted: Jun. 29, 2016, Last Update: Mar. 19, 2019, https://clinicaltrials.gov/ct2/show/study/NCT02817633. Date Accessed, Mar. 25, 2019 (8 pages).
Therasse et al., 2000, "New Guidelines to Evaluate the Response to Treatment in Solid Tumors," *Journal of the National Cancer Institute* 92(3):205-216.
Tortorici et al., 2011, "Influence of mild and moderate hepatic impairment on axitinib pharmacokinetics," Investigational New Drugs 29:1370-1380.
Toyozawa, et al., 2012, "Chemokine receptor CXCR4 is a novel marker for the progression of cutaneous malignant melanoma," *Japan Society of Histochemisty and Cytochemistry* 45(5):293-299.
Trillium Therapeutics Inc., "A Trial of TTI-621 for Patients With Hematologic Malignancies and Selected Solid Tumors," ClinicalTrials. gov: NCT02663518, First Posted: Jan. 26, 2016, Last Update: Oct. 29, 2018, https://clinicaltrials.gov/ct2/show/study/NCT02663518. Date Accessed, Mar. 18, 2019 (9 pages).
Trillium Therapeutics Inc., "Trial of Intratumoral Injections of TTI-621 in Subjects With Relapsed and Refractory Solid Tumors and Mycosis Fungoides," ClinicalTrials.gov: NCT02890368, First Posted: Sep. 7, 2016, Last Update: Mar. 13, 2019, https://clinicaltrials. gov/ct2/show/study/NCT02890368. Date Accessed, Mar. 18, 2019 (9 pages).
Tu S.P. et al., 2012, "Curcumin induces the differentiation of myeloid-derived suppressor cells and inhibits their interaction with cancer cells and related tumor growth," *Cancer Prevention Research* 5(2);205-215.
Tumeh, et al., 2014, "PD-1 blockade induces responses by inhibiting adaptive immune resistance," Nature 515(7528):568-571.
U.S. Appl. No. 16/311,083, filed Dec. 18, 2018 (276 pages).
University of Southern California, "Axitinib With or Without Anti-OX40 Antibody PF-04518600 in Treating Patients With Metastatic Kidney Cancer," ClinicalTrials.gov: NCT03092856, First Posted: Mar. 28, 2017, Last Update: Aug. 13, 2018, https://clinicaltrials. gov/ct2/show/study/NCT03092856. Date Accessed, Mar. 18, 2019 (11 pages).
University of Texas Southwestern Medical Center, "Phase 2 Study of IDH305 in Low Grade Gliomas," ClinicalTrials.gov: NCT02987010, First Posted: Dec. 8, 2016, Last Update: Oct. 11, 2017, https://clinicaltrials.gov/ct2/show/study/NCT02987010. Date Accessed, Mar. 25, 2019 (7 pages).
Vaishampayan et al., "A Phase 1/2 Study Evaluating the Efficacy and Safety of the Oral CXCR4 Inhibitor X4P-001 in Combination with Axitinib in Patients with Advanced Renal Cell Carcinoma,"

(56) References Cited

OTHER PUBLICATIONS

2018 American Society for Clinical Oncology Annual Meeting, Chicago, Illinois, Jun. 2, 2018 (1 page).
Vanharanta et al., 2013, "Epigenetic expansion of VHL-HIF signal output drives multiorgan metastasis in renal cancer," Natural Medicine 19(1):50-56.
VentiRx Pharmaceuticals Inc., "A Phase Ib Study of Neoadjuvant of Cetuximab Plus Motolimod and Cetuximab Plus Motolimod Plus Nivolumab," ClinicalTrials.gov: NCT02124850, First Posted: Apr. 28, 2014, Last Update: Jul. 22, 2016, https://clinicaltrials.gov/ct2/show/study/NCT02124850. Date Accessed, Mar. 25, 2019 (6 pages).
Ward et al., 2009, "Genetic and molecular diagnosis of severe congenital neutropenia," *Current Opinion in Hematology* 16(1):9-13.
Wong, 2008, "Comparison of the potential multiple binding modes of bicyclam, monocyclam, and noncyclam small molecule CXC chemokine receptor 4 inhibitors," *Molecular Pharmacology* 74(6):1485-1495.
X4 Pharmaceuticals, "Trial of X4P-001 in Patients with Advanced Renal Cell Carcinoma," ClinicalTrials.gov: NCT02667886, First Posted: Jan. 29, 2016, https://clinicaltrials.gov/ct2/show/study/NCT02667886. Date Accessed, Aug. 18, 2021 (10 pages).
Zagzag et al., "Stromal Cell-Derived Factor-1 and CXCR4 Expression in Hemangioblastoma and Clear Cell-Renal Cell Carcinoma: von Hippel-Lindau Loss-of-Function Induces Expression of a Ligand and its Receptor," Cancer Research 2005; 65(14): 6178-6188.
Zea A.H. et al., 2005, "Arginase-producing myeloid suppressor cells in renal cell carcinoma patients: a mechanism of tumor evasion," *Cancer Research* 65(8):3044-3048.
Zhang et al., 1998, "Chemokine Coreceptor Usage by Diverse Primary Isolates of Human Immunodeficiency Virus Type 1," *Journal of Virology* 72(11):9307-9312.
Zhang et al., 1999, "Will Multiple Coreceptors Need To Be Targeted by Inhibitors of Human Immunodeficiency Virus Type 1 Entry?," *Journal of Virology* 73(4):3443-3448.
Zhang et al., 2006, "Preferential involvement of CXCR4 and CXCL12 in T cell migration toward melanoma cells," *Cancer Biology & Therapy* 5(10):1034-1312.
Zhao et al., 2012, "TNF signaling drives myeloid-derived suppressor cell accumulation," Journal of Clinical Investigation 122(11):4094-4104.
Zlotnik et al., 2000, "Chemokines: a new classification system and their role in immunity," *Immunity* 12:121-127.
Zou et al., "PD-L1 (B7-H1) and PD-1 pathway blockage for cancer therapy: Mechanisms, response biomarkers, and combinations," Sci Transl. Med. 2016;8(328):328rv4.
Zuelzer, 1964, "'Myelokathexis'—A New Form of Chronic Granulocytopenia. Report of a case," New England Journal of Medicine 270(14): 699-704.
X4 Pharmaceuticals, "Addition of X4P-001 to Nivolumab Treatment in Patients With Renal Cell Carcinoma", ClinicalTrails.gov Identifier: NCT02923531. First submitted Feb. 8, 2017, Lastest version submitted Jul. 24, 2019, https://clinicaltrials.gov/ct2/history/NCT02923531?V_4=View#StudyPageTop.
X4 Pharmaceuticals, "X4 Pharmaceuticals announces new data for lead candidate X4P-001 in renal cell carcinoma at EORTC-NCI-AACR Molecular Targets and Cancer Therapeutic Symposium", Nov. 30, 2016, Cambridge Mass, https://www.x4pharma.com/news/x4-pharmaceuticals-announces-new-data-lead-candidate-x4p-001-renal-cell-carcinoma-eortc-nci-aacr-molecular-targets-cancer-therapeutics-symposium/.
Hughes et al., "HIF-2? downregulation in the absence of functional VHL is not sufficient for renal cell differentiation", Cancer Cell Int. Jun. 28, 2007;7:13.
Moch and Lukamowicz-Rajska. "miR-30c-2-3p and miR-30a-3p: New Pieces of the Jigsaw Puzzle in HIF2? Regulation", Cancer Discov (2014) 4 (1): 22-24.
Dale and Bolyard, "An update on the diagnosis and treatment of chronic idiopathic neutropenia." Curr Opin Hematol. 2017. 24:46-53.
PCT International Search Report and Written Opinion from PCT/US2023/016451 dated Aug. 4, 2023.

* cited by examiner

COMPOSITIONS OF CXCR4 INHIBITORS AND METHODS OF PREPARATION AND USE

TECHNICAL FIELD OF THE INVENTION

The present invention relates to compounds that inhibit C-X-C receptor type 4 (CXCR4). The invention also provides pharmaceutically acceptable compositions comprising compounds of the present invention and methods of using said compositions in the treatment of various disorders.

CROSS-REFERENCE TO RELATED APPLICATIONS

This application is a continuation of U.S. patent application Ser. No. 17/359,391, filed Jun. 25, 2021, now U.S. Pat. No. 11,672,793; which is a continuation of U.S. patent application Ser. No. 16/704,302, now U.S. Pat. No. 11,045,461, filed Dec. 5, 2019; which is a continuation of U.S. patent application Ser. No. 16/215,963, now U.S. Pat. No. 10,548,889, filed Dec. 11, 2018; which claims the benefit of U.S. Provisional Patent Application No. 62/726,010, filed Aug. 31, 2018; the entirety of each of which is hereby incorporated by reference.

BACKGROUND OF THE INVENTION

C-X-C chemokine receptor type 4 (CXCR4), also known as fusin or cluster of differentiation 184 (CD184), is a seven transmembrane G-protein coupled receptor (GPCR) belonging to Class I GPCR or rhodopsin-like GPCR family. Under normal physiological conditions, CXCR4 carries out multiple roles and is principally expressed in the hematopoietic and immune systems. CXCR4 was initially discovered as one of the co-receptors involved in human immunodeficiency virus (HIV) cell entry. Subsequent studies showed that it is expressed in many tissues, including brain, thymus, lymphatic tissues, spleen, stomach, and small intestine, and also specific cell types such as hematopoietic stem cells (HSC), mature lymphocytes, and fibrobRlasts. CXCL12, previously designated SDF-1α, is the only known ligand for CXCR4. CXCR4 mediates migration of stem cells during embryonic development as well as in response to injury and inflammation. Multiple roles have been demonstrated for CXCR4 in human diseases such as cellular proliferative disorders, Alzheimer's disease, HIV, rheumatoid arthritis, pulmonary fibrosis, and others. For example, expression of CXCR4 and CXCL12 have been noted in several tumor types. CXCL12 is expressed by cancer-associated fibroblast (CAFs) and is often present at high levels in the tumor microenvironment (TME). In clinical studies of a wide range of tumor types, including breast, ovarian, renal, lung, and melanoma, expression of CXCR4/CXCL12 has been associated with a poor prognosis and with an increased risk of metastasis to lymph nodes, lung, liver, and brain, which are sites of CXCL12 expression. CXCR4 is frequently expressed on melanoma cells, particularly the CD133+ population that is considered to represent melanoma stem cells; in vitro experiments and murine models have demonstrated that CXCL12 is chemotactic for such cells.

Furthermore, there is now evidence implicating the CXCL12/CXCR4 axis in contributing to the loss or lack of tumor responsiveness to angiogenesis inhibitors (also referred to as "angiogenic escape"). In animal cancer models, interference with CXCR4 function has been demonstrated to alter the TME and sensitize the tumor to immune attack by multiple mechanisms such as elimination of tumor re-vascularization and increasing the ratio of CD8+ T cells to Treg cells. These effects result in significantly decreased tumor burden and increased overall survival in xenograft, syngeneic, and transgenic cancer models. See Vanharanta et al. (2013) Nat Med 19: 50-56; Gale and McColl (1999) BioEssays 21: 17-28; Highfill et al. (2014) Sci Transl Med 6: ra67; Facciabene et al. (2011) Nature 475: 226-230.

These data underscore the significant, unmet need for CXCR4 inhibitors to treat the many diseases and conditions mediated by aberrant or undesired expression of the receptor, for example in cellular proliferative disorders.

SUMMARY OF THE INVENTION

It has now been found that disclosed X4P-001 compositions of the present invention, and pharmaceutically acceptable compositions thereof, are effective as CXC receptor type 4 (CXCR4) inhibitors. In one aspect, the present invention provides an X4P-001 composition comprising a compound of formula I:

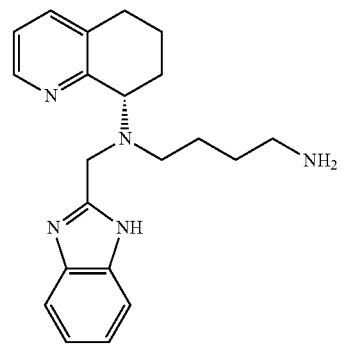

I or a pharmaceutically acceptable salt thereof; and at least one compound selected from the following:

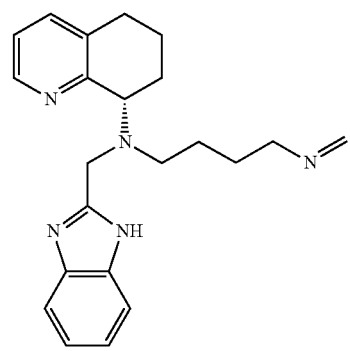

I-1

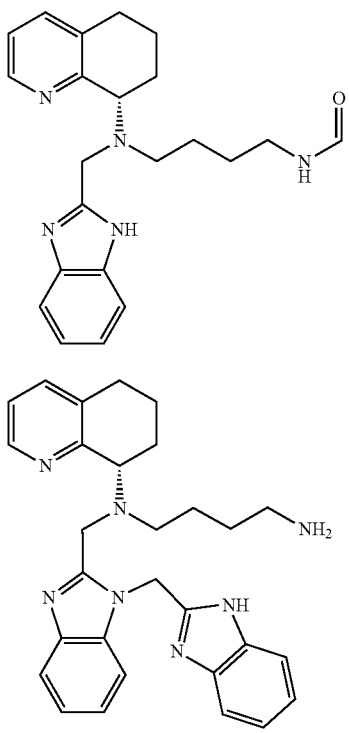

I-2

I-3

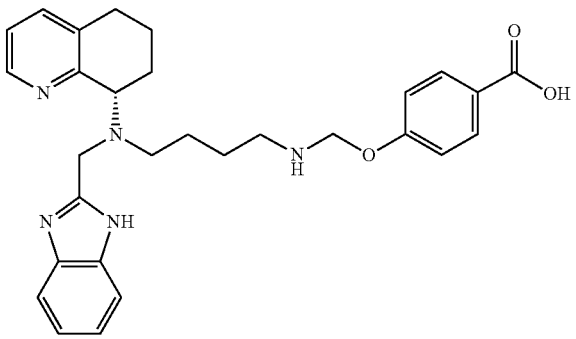

I-4

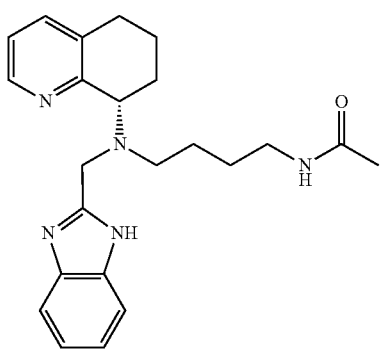

I-5

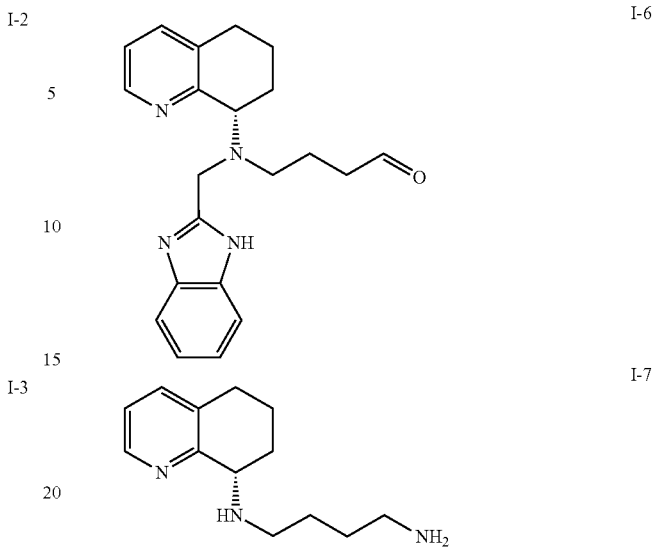

I-6

I-7 or a pharmaceutically acceptable salt thereof.

X4P-001 compositions of the present invention, and pharmaceutically acceptable compositions thereof, are useful for treating a variety of diseases, disorders, or conditions associated with CXCR4, such as hyperproliferative conditions including various cancers. Such diseases, disorders, or conditions include those described herein.

DETAILED DESCRIPTION OF THE INVENTION

Figure 1:
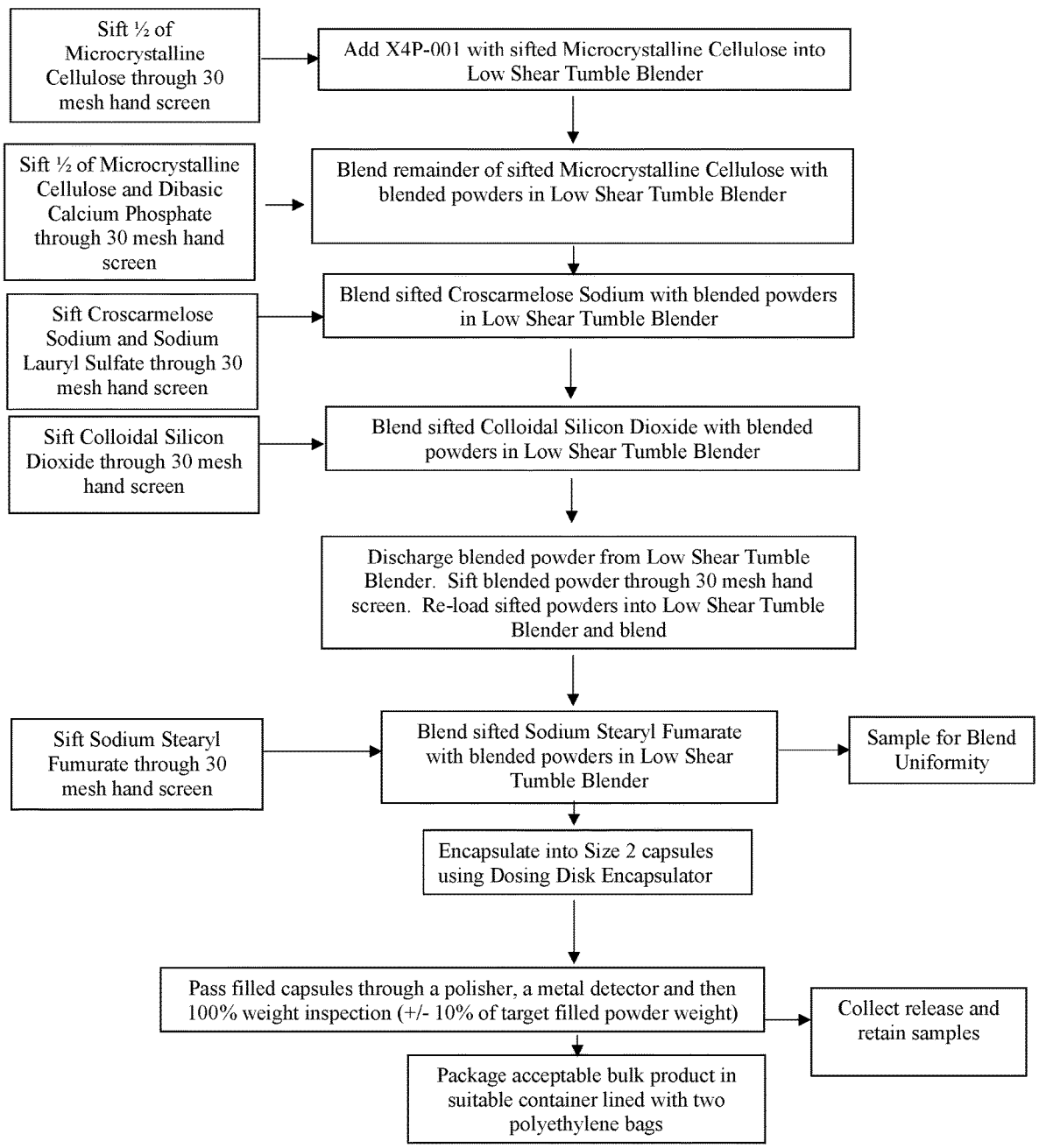
FIG. 1 shows a detailed summary of the manufacturing process for capsules containing a solid drug product formulation (unit dosage form) of X4P-001.

1. General Description of Certain Aspects of the Invention

In one aspect, the present invention provides compounds and compositions thereof useful for treatment, prevention, and/or reduction of a risk of a disease, disorder, or condition in which CXCR4 is implicated in the pathogenesis. In some embodiments, such compounds include those of the formulae described herein, or a pharmaceutically acceptable salt thereof.

In another aspect, the present invention provides compositions, including formulations and unit dosage forms, comprising X4P-001 (i.e., a compound of formula I, whose structure is shown below) or a pharmaceutically acceptable salt thereof, wherein such compositions exhibit an improved purity profile. In some embodiments, a disclosed X4P-001 composition exhibits reduced levels of known impurities such as those described herein, and/or reduced levels of unknown impurities, in comparison with similar compositions prepared by conventional means.

In another aspect, the present invention provides an X4P-001 composition comprising a compound of formula I:

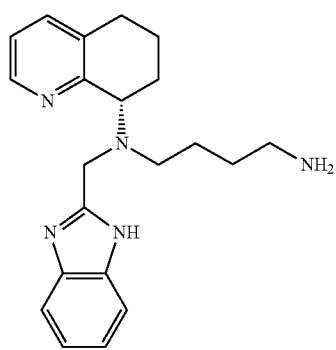

I or a pharmaceutically acceptable salt thereof; and at least one compound selected from the following:

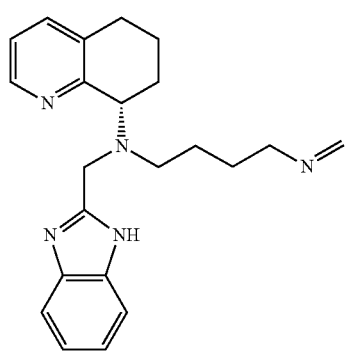

I-1

-continued

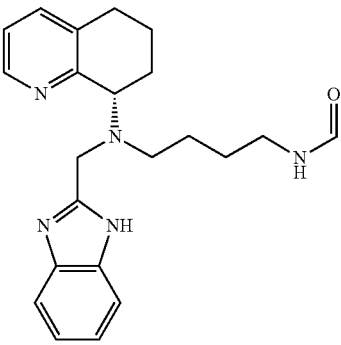

I-2

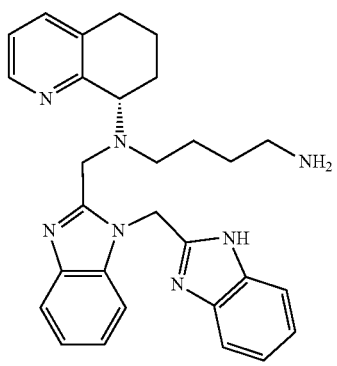

I-3

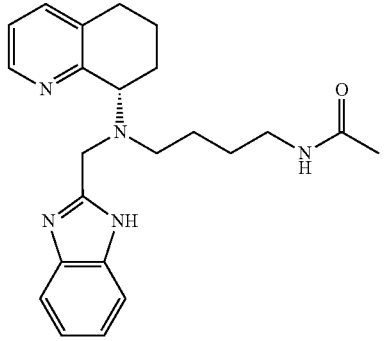

I-4

I-5

-continued

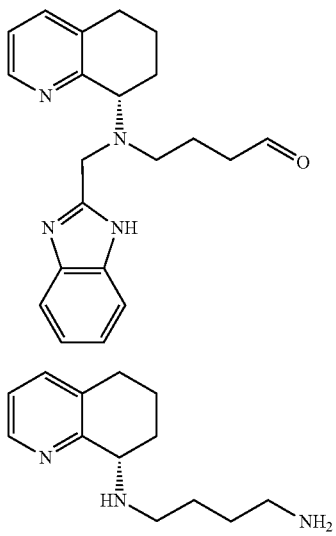

I-6

I-7 or a pharmaceutically acceptable salt thereof.

2. Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry," 5$^{th}$ Ed., Ed.: Smith, M. B. and March, J., John Wiley & Sons, New York: 2001, the entire contents of each of which are hereby incorporated by reference.

As used herein, the term "X4P-001 composition" or "disclosed X4P-001 composition" refers to a composition comprising a compound of formula I (i.e., X4P-001), or a pharmaceutically acceptable salt thereof, in combination with at least one additional compound selected from I-1, I-2, I-3, I-4, I-5, I-6, or I-7. For clarity, a "pharmaceutical composition" of a disclosed X4P-001 composition refers to a composition comprising a compound of formula I (i.e., X4P-001), or a pharmaceutically acceptable salt thereof, in combination with at least one additional compound selected from I-1, I-2, I-3, I-4, I-5, I-6, or I-7, together with a pharmaceutically acceptable excipient, e.g., adjuvant, filler, binder, carrier, or vehicle.

Additional known or unknown impurities may be present in a disclosed X4P-001 composition. As used herein, the term "impurity" includes one or more degradants which arise during storage of X4P-001 and/or one or more by-products formed in a chemical reaction used in manufacturing of X4P-001. In some embodiments, an impurity results from oxidation, light-initiated decomposition, reaction with a residual solvent such as water or isopropyl acetate, a side reaction that takes place during the process used to prepare X4P-001, or a reaction of X4P-001 with an excipient present in an X4P-001 pharmaceutical composition.

As used herein, the term "inhibitor" is defined as a compound that binds to and/or inhibits CXCR4 with measurable affinity. In certain embodiments, an inhibitor has an $IC_{50}$ and/or binding constant of less than about 100 μM, less than about 50 μM, less than about 1 μM, less than about 500 nM, less than about 100 nM, less than about 10 nM, or less than about 1 nM.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts include salts of a basic group (e.g. an amino group) formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid; or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemi sulfate, heptanoate, hexanoate, hydroiodide, 2-hydroxy-ethanesulfonate, lactobionate, lactate, laurate, lauryl sulfate, malate, maleate, malonate, mesylate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, ($C_{1-6}$ alkyl)sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

As used herein, a "therapeutically effective amount" or "an effective amount" means an amount of a substance (e.g., a therapeutic agent, composition, and/or formulation) that elicits a desired biological response. In some embodiments, a therapeutically effective amount of a substance is an amount that is sufficient, when administered as part of a dosing regimen to a subject suffering from or susceptible to a disease, condition, or disorder, to treat, diagnose, prevent, and/or delay the onset of the disease, condition, or disorder. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, condition, or disorder is the amount that alleviates, ameliorates, relieves, inhibits, prevents, delays onset of, reduces severity of and/or reduces incidence of one or more symptoms or features of the disease, condition, or disorder. In some embodiments, a "therapeutically effective amount" is at least a minimal amount of a compound, or composition containing a compound, which is sufficient for treating one or more symptoms of a disease or disorder.

As used herein, the terms "treatment," "treat," and "treating" refer to partially or completely alleviating, inhibiting, delaying onset of, preventing, ameliorating and/or relieving a disease or disorder, or one or more symptoms of the disease or disorder, as described herein. In some embodiments, treatment may be administered after one or more symptoms have developed. In some embodiments, the term "treating" includes preventing or halting the progression of a disease or disorder. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence. Thus, in some embodiments, the term "treating" includes preventing relapse or recurrence of a disease or disorder.

As used herein, the term "CXCR4-mediated" in reference to a disorder, disease, and/or condition means any disease, disorder, or condition in which CXCR4, or a mutant thereof, is known to play a role. Accordingly, another embodiment of the present invention relates to treating or lessening the severity of one or more diseases in which CXCR4, or a mutant thereof, is known to play a role. "CXCR4-mediated" also includes diseases, disorders, and conditions in which the CXCR4/CXCL12 axis is implicated.

The term "unit dosage form" as used herein refers to a physically discrete unit of therapeutic formulation appropriate for the subject to be treated. It will be understood, however, that the total daily usage of the X4P-001 compositions of the present invention will be decided by the attending physician within the scope of sound medical judgment. The specific effective dose level for any particular subject or organism will depend upon a variety of factors including the disorder being treated and the severity of the disorder; activity of specific active agent employed; specific composition employed; age, body weight, general health, sex and diet of the subject; time of administration, and rate of excretion of the specific active agent employed; duration of the treatment; drugs and/or additional therapies used in combination or coincidental with specific compound(s) employed, and like factors well known in the medical arts.

3. Description of Exemplary Compounds

It has now been found that compounds of the present invention, and compositions thereof, are useful for treating, preventing, and/or reducing a risk of a disease, disorder, or condition associated with CXCR4 or for which CXCR4 is associated with its pathogenesis.

In one aspect, the present invention provides a composition comprising X4P-001, or a pharmaceutically acceptable salt thereof, in at least 98.5% purity. In some embodiments, the X4P-001 in the composition is at least 98.5% pure and contains less than 1.5% w/w impurities. In some embodiments, the composition comprises X4P-001 or a pharmaceutically acceptable salt thereof in at least 98.6%, 98.7%, 98.8%, 98.9%, 99.0%, 99.1%, 99.2%, 99.3%, 99.4%, 99.5%, 99.6%, 99.7%, 99.8%, or 99.9% purity.

In one aspect, the present invention provides an X4P-001 composition comprising a compound of formula I:

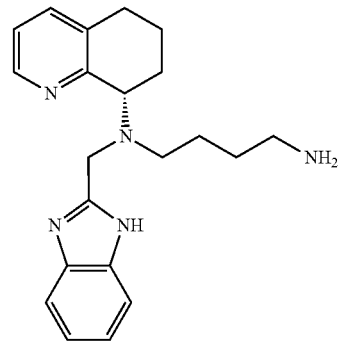

I or a pharmaceutically acceptable salt thereof; and a detectable amount of at least one of the following compounds:

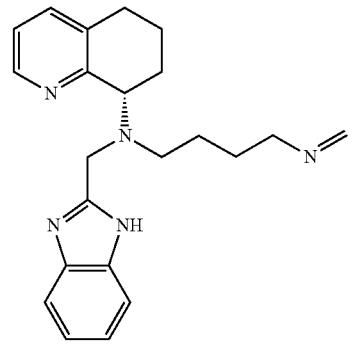

I-1

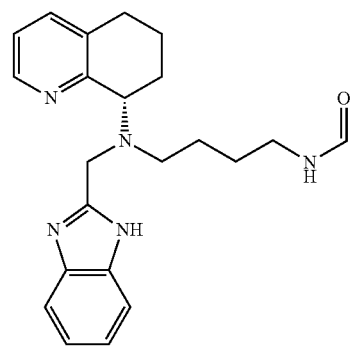

I-2

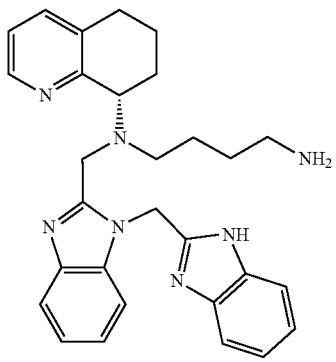

I-3

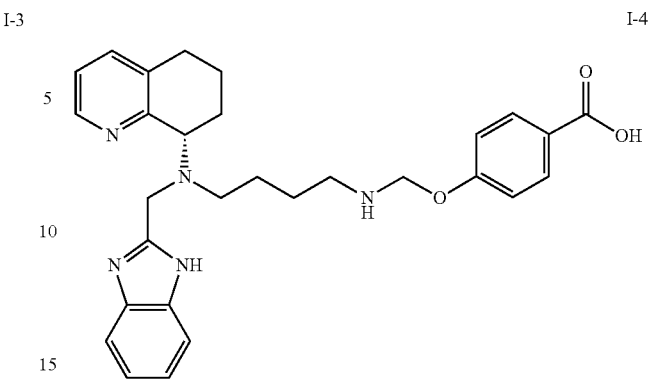

I-4

I-5

I-6

I-7 or a pharmaceutically acceptable salt thereof; and wherein the X4P-001 composition does not include the following compound in a detectable amount:

or a pharmaceutically acceptable salt thereof.

In some embodiments, the X4P-001 composition comprises each of I-1, I-2, I-3, I-5, I-6, and I-7; or a pharmaceutically acceptable salt thereof.

In some embodiments, the amount of I-1, or a pharmaceutically acceptable salt thereof, is less than about 0.5% w/w of the X4P-001 composition.

In some embodiments, the amount of I-2, or a pharmaceutically acceptable salt thereof, is less than about 0.3% w/w of the X4P-001 composition.

In some embodiments, the amount of I-3, or a pharmaceutically acceptable salt thereof, is less than about 0.4% w/w of the X4P-001 composition.

In some embodiments, the amount of I-5, or a pharmaceutically acceptable salt thereof, is less than about 0.4% w/w of the X4P-001 composition.

In some embodiments, the amount of I-6, or a pharmaceutically acceptable salt thereof, is less than about 0.4% w/w of the X4P-001 composition.

In some embodiments, the amount of I-7, or a pharmaceutically acceptable salt thereof, is less than about 0.25% w/w of the X4P-001 composition.

In some embodiments, the amount of I-1, or a pharmaceutically acceptable salt thereof, is from about 0.02 to about 0.5% w/w of the X4P-001 composition.

In some embodiments, the amount of I-2, or a pharmaceutically acceptable salt thereof, is from about 0.01 to about 0.3% w/w of the X4P-001 composition.

In some embodiments, the amount of I-3, or a pharmaceutically acceptable salt thereof, is from about 0.01 to about 0.4% w/w of the X4P-001 composition.

In some embodiments, the amount of I-5, or a pharmaceutically acceptable salt thereof, is from about 0.01 to about 0.4% w/w of the X4P-001 composition.

In some embodiments, the amount of I-6, or a pharmaceutically acceptable salt thereof, is from about 0.01 to about 0.4% w/w of the X4P-001 composition.

In some embodiments, the amount of I-7, or a pharmaceutically acceptable salt thereof, is from about 0.01 to about 0.25% w/w of the X4P-001 composition.

In one aspect, the present invention provides a pharmaceutical composition comprising a disclosed X4P-001 composition, and a pharmaceutically acceptable adjuvant, carrier, or vehicle.

In some embodiments, the pharmaceutically acceptable adjuvant includes at least one diluent, a disintegrant, a lubricant, and a flow aid.

In another aspect, the present invention provides a pharmaceutical composition comprising a disclosed X4P-001 composition, wherein:

(a) the amount of I-1, or a pharmaceutically acceptable salt thereof, is less than about 0.5% w/w of the X4P-001 composition;
(b) the amount of I-2, or a pharmaceutically acceptable salt thereof, is less than about 0.3% w/w of the X4P-001 composition;
(c) the amount of I-3, or a pharmaceutically acceptable salt thereof, is less than about 0.4% w/w of the X4P-001 composition;
(d) the amount of I-5, or a pharmaceutically acceptable salt thereof, is less than about 0.4% w/w of the X4P-001 composition;
(e) wherein the amount of I-6, or a pharmaceutically acceptable salt thereof, is less than about 0.4% w/w of the X4P-001 composition; and
(f) the amount of I-7, or a pharmaceutically acceptable salt thereof, is less than about 0.25% w/w of the X4P-001 composition.

In one aspect, the present invention provides a pharmaceutical composition comprising a disclosed X4P-001 composition, wherein:
(a) the amount of I-1, or a pharmaceutically acceptable salt thereof, is from about 0.02 to about 0.5% w/w of the X4P-001 composition;
(b) the amount of I-2, or a pharmaceutically acceptable salt thereof, is from about 0.01 to about 0.3% w/w of the X4P-001 composition;
(c) the amount of I-3, or a pharmaceutically acceptable salt thereof, is from about 0.01 to about 0.4% w/w of the X4P-001 composition;
(d) the amount of I-5, or a pharmaceutically acceptable salt thereof, is from about 0.01 to about 0.4% w/w of the X4P-001 composition;
(e) the amount of I-6, or a pharmaceutically acceptable salt thereof, is from about 0.01 to about 0.4% w/w of the X4P-001 composition; and
(f) the amount of I-7, or a pharmaceutically acceptable salt thereof, is from about 0.01 to about 0.25% w/w of the X4P-001 composition.

In another aspect, the present invention provides a unit dosage form comprising a pharmaceutical composition comprising:
(a) a disclosed X4P-001 composition, in about 10-20% by weight of the composition;
(b) microcrystalline cellulose in about 70-85% by weight of the composition;
(c) croscarmellose sodium in about 5-10% by weight of the composition;
(d) sodium stearyl fumarate in about 0.5-2% by weight of the composition; and
(e) colloidal silicon dioxide in about 0.1-1.0% by weight of the composition.

In another aspect, the present invention provides a unit dosage form comprising a pharmaceutical composition comprising:
(a) a disclosed X4P-001 composition, in about 35-75% by weight of the composition;
(b) microcrystalline cellulose in about 5-28% by weight of the composition;
(c) dibasic calcium phosphate dihydrate in about 7-30% by weight of the composition;
(d) croscarmellose sodium in about 2-10% by weight of the composition;
(e) sodium stearyl fumarate in about 0.3-2.5% by weight of the composition;
(f) colloidal silicon dioxide in about 0.05-1.2% by weight of the composition; and (g) sodium lauryl sulfate in about 0.2-1.2% by weight of the composition.

In one aspect, the present invention provides a method of treating, preventing, or reducing a risk of a disease, disorder, or condition associated with CXCR4 in a subject in need thereof, comprising administering to the subject an effective amount of a disclosed X4P-001 composition.

In some embodiments, the disease, disorder, or condition is a cancer selected from kidney cancer, renal tumor, renal carcinoma, ovarian cancer, or melanoma.

In one aspect, the present invention provides an X4P-001 composition comprising a compound of formula I:

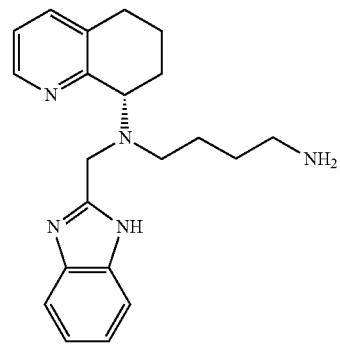

I or a pharmaceutically acceptable salt thereof; and at least one compound selected from the following:

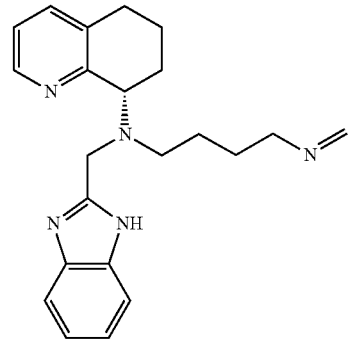

I-1

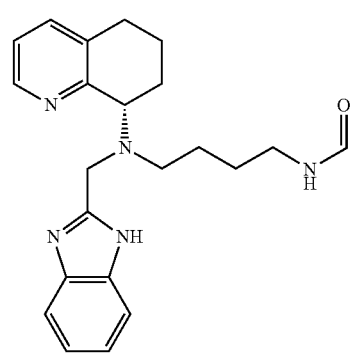

I-2

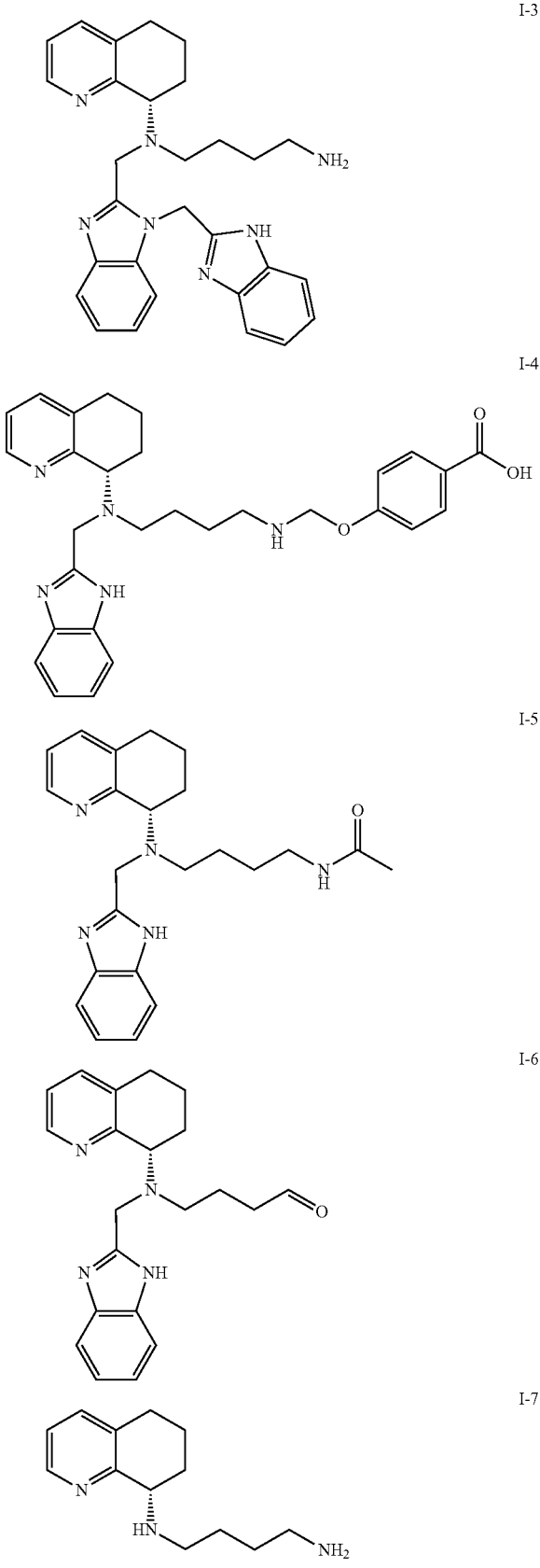
or a pharmaceutically acceptable salt thereof.
In another aspect, the present invention provides an X4P-001 composition comprising a compound of formula I:
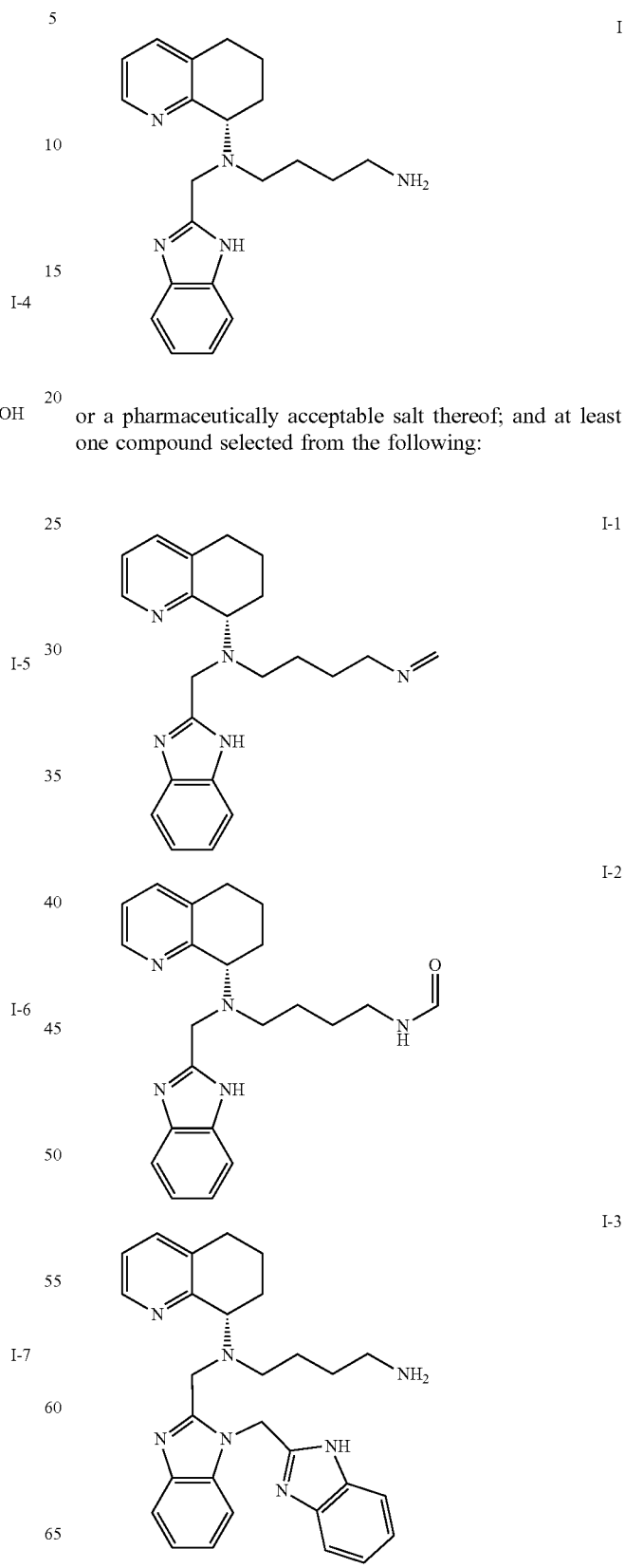
or a pharmaceutically acceptable salt thereof; and at least one compound selected from the following:

I-5

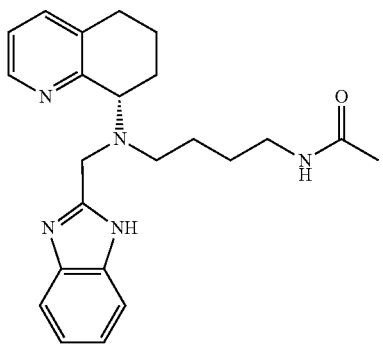

I-6

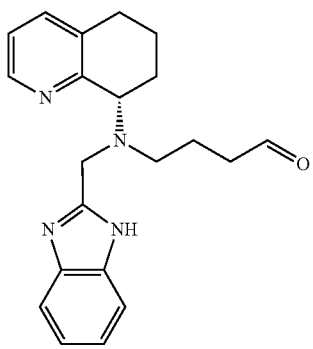

I-7

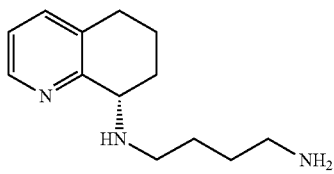

or a pharmaceutically acceptable salt thereof.

In some embodiments, the present invention provides an X4P-001 composition comprising a compound of formula I:

I

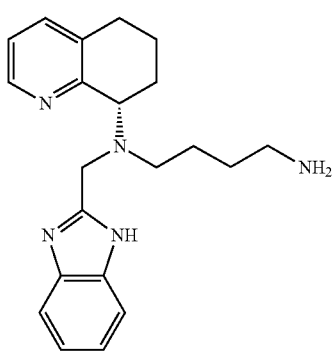

or a pharmaceutically acceptable salt thereof; and a compound of the following structure:

I-6

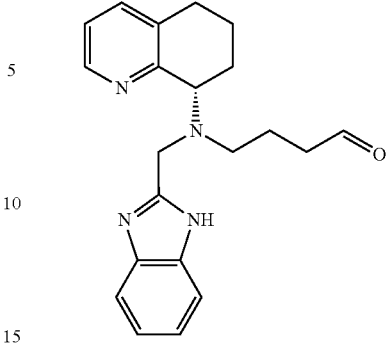

or a pharmaceutically acceptable salt thereof. In some embodiments, the total weight of I-6 and any additional impurities that are present comprise no more than about 0.8% w/w of the X4P-001 composition.

In some embodiments, the X4P-001 composition comprises I-6, or a pharmaceutically acceptable salt thereof, in at least a detectable amount.

In some embodiments, the X4P-001 composition comprises two, three, or four compounds selected from I-1, I-2, I-3, I-4, I-5, I-6, or I-7; or a pharmaceutically acceptable salt thereof. In some embodiments, the X4P-001 composition comprises at least a detectable amount of two, three, or four compounds selected from I-1, I-2, I-3, I-4, I-5, I-6, or I-7; or a pharmaceutically acceptable salt thereof.

In some embodiments, the X4P-001 composition comprises three compounds selected from I-1, I-2, I-3, I-4, I-5, I-6, or I-7; or a pharmaceutically acceptable salt thereof. In some embodiments, the X4P-001 composition comprises at least a detectable amount of three compounds selected from I-1, I-2, I-3, I-4, I-5, I-6, or I-7; or a pharmaceutically acceptable salt thereof.

In some embodiments, the X4P-001 composition comprises each of I-1, I-2, I-3, I-5, I-6, and I-7; or a pharmaceutically acceptable salt thereof. In some embodiments, the X4P-001 composition comprises at least a detectable amount of each of I-1, I-2, I-3, I-5, I-6, and I-7; or a pharmaceutically acceptable salt thereof.

In some embodiments, the total amount of I-6 or a pharmaceutically acceptable salt thereof represents no more than about 0.2% w/w of the X4P-001 composition relative to the total weight in the X4P-001 composition of the compound of formula I and the one or more compounds selected from I-1, I-2, I-3, I-4, I-5, I-6, or I-7; or a pharmaceutically acceptable salt thereof. In some embodiments, the X4P-001 composition comprises at least a detectable amount of I-6 or a pharmaceutically acceptable salt thereof.

In some embodiments, the X4P-001 composition comprises no more than 0.15% w/w of I-6 relative to the total weight in the X4P-001 composition of the compound of formula I and the one or more compounds selected from I-1, I-2, I-3, I-4, I-5, I-6, or I-7; or a pharmaceutically acceptable salt thereof. In some embodiments, the X4P-001 composition comprises at least a detectable amount of I-6 or a pharmaceutically acceptable salt thereof.

In some embodiments, the one or more compounds selected from I-1, I-2, I-3, I-4, I-5, I-6, or I-7; or a pharmaceutically acceptable salt thereof together represent less than about 3.0% w/w of the X4P-001 composition relative to the total weight in the X4P-001 composition of the compound of formula I and the one or more compounds selected from I-1, I-2, I-3, I-4, I-5, I-6, or I-7; or a pharmaceutically acceptable salt thereof. In some embodiments, the one or more compounds selected from I-1, I-2, I-3, I-4, I-5, I-6, or I-7; or a pharmaceutically acceptable salt thereof are present in at least a detectable amount in the X4P-001 composition. In some embodiments, the X4P-001 composition comprises a compound of formula I, or a pharmaceutically acceptable salt thereof, and does not comprise a compound of formula I-4, or a pharmaceutically acceptable salt thereof, in a detectable amount.

In some embodiments, the total organic impurities, including the one or more compounds selected from I-1, I-2, I-3, I-4, I-5, I-6, or I-7; or a pharmaceutically acceptable salt thereof, comprise less than about 4.0% w/w of the X4P-001 composition.

In some embodiments, the amount of I-1, or a pharmaceutically acceptable salt thereof, is less than about 0.5% w/w of the X4P-001 composition.

In some embodiments, the amount of I-2, or a pharmaceutically acceptable salt thereof, is less than about 0.3% w/w of the X4P-001 composition.

In some embodiments, the amount of I-3, or a pharmaceutically acceptable salt thereof, is less than about 0.4% w/w of the X4P-001 composition.

In some embodiments, the X4P-001 composition does not include I-4, or a pharmaceutically acceptable salt thereof, in a detectable amount.

In some embodiments, the amount of I-5, or a pharmaceutically acceptable salt thereof, is less than about 0.07% w/w of the X4P-001 composition.

In some embodiments, the amount of I-6, or a pharmaceutically acceptable salt thereof, is less than about 0.4% w/w of the X4P-001 composition.

In some embodiments, the amount of I-7, or a pharmaceutically acceptable salt thereof, is less than about 0.25% w/w of the X4P-001 composition.

In some embodiments, at least a detectable amount of I-1, I-2, I-3, I-5, I-6, or I-7; or a pharmaceutically acceptable salt thereof is present in the X4P-001 composition.

In some embodiments, the amount of I-1, or a pharmaceutically acceptable salt thereof, is from about 0.02 to about 0.5% w/w of the X4P-001 composition.

In some embodiments, the amount of I-2, or a pharmaceutically acceptable salt thereof, is from about 0.01 to about 0.3% w/w of the X4P-001 composition.

In some embodiments, the amount of I-3, or a pharmaceutically acceptable salt thereof, is from about 0.01 to about 0.4% w/w of the X4P-001 composition.

In some embodiments, the amount of I-5, or a pharmaceutically acceptable salt thereof, is from about 0.01 to about 0.07% w/w of the X4P-001 composition.

In some embodiments, the amount of I-6, or a pharmaceutically acceptable salt thereof, is from about 0.01 to about 0.4% w/w of the X4P-001 composition.

In some embodiments, the amount of I-7, or a pharmaceutically acceptable salt thereof, is from about 0.01 to about 0.25% w/w of the X4P-001 composition.

In some embodiments, the X4P-001 composition comprises the compound of formula I or a pharmaceutically acceptable salt thereof in at least 99.3% purity by HPLC and comprises less that 0.7% total additional compounds selected from I-1, I-2, I-3, I-5, I-6, or I-7; or a pharmaceutically acceptable salt thereof, as measured by HPLC. In some embodiments, at least a detectable amount of one or more of the additional compounds is present.

In one aspect, the present invention provides an X4P-001 composition comprising a compound of formula I:

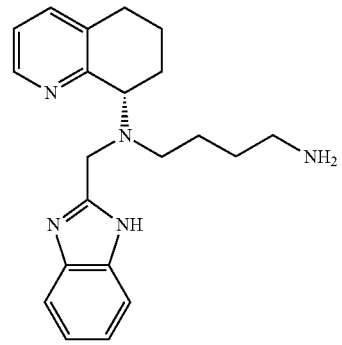

or a pharmaceutically acceptable salt thereof, and one or more compounds selected from the following:

(a)

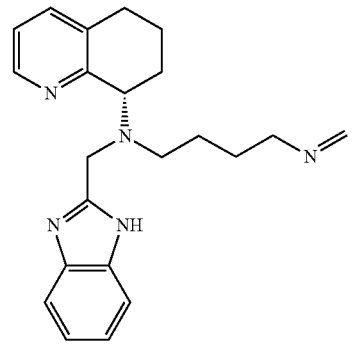

or a pharmaceutically acceptable salt thereof, in an amount that is not more than about 0.5% w/w of the X4P-001 composition;

(b)

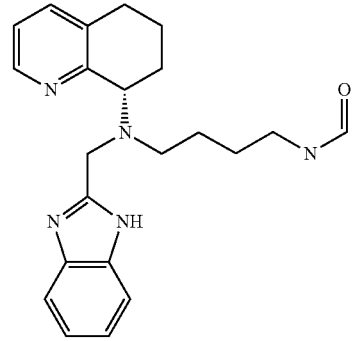

or a pharmaceutically acceptable salt thereof, in an amount that is not more than about 0.3% w/w of the X4P-001 composition;

(c)

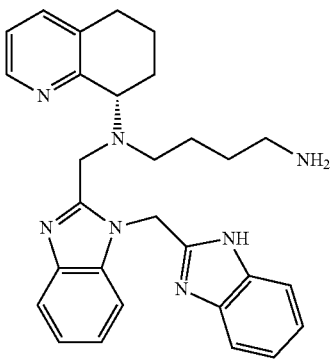

I-3 or a pharmaceutically acceptable salt thereof, in an amount that is not more than about 0.4% w/w of the X4P-001 composition;

(d)

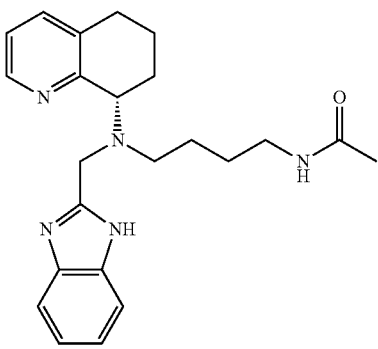

I-5 or a pharmaceutically acceptable salt thereof, in an amount that is not more than about 0.5% w/w of the X4P-001 composition;

(e)

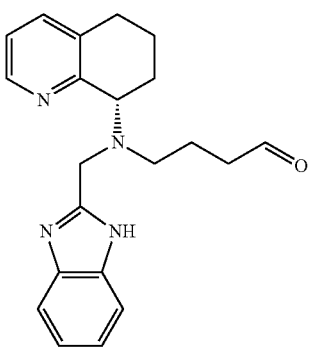

I-6 or a pharmaceutically acceptable salt thereof, in an amount that is not more than about 0.4% w/w of the X4P-001 composition; or (f)

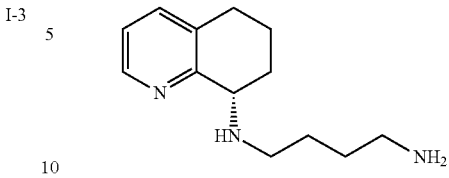

I-7 or a pharmaceutically acceptable salt thereof, in an amount that is not more than about 0.25% w/w of the X4P-001 composition; wherein each % w/w is measured relative to the total weight in the X4P-001 composition of the compound of formula I and the one or more compounds selected from I-1, I-2, I-3, I-5, I-6, or I-7. In some embodiments, the X4P-001 composition comprises a compound of formula I, or a pharmaceutically acceptable salt thereof, and does not comprise a compound of formula I-4, or a pharmaceutically acceptable salt thereof, in a detectable amount.

In some embodiments, the chiral purity of the X4P-001 composition is at least about 97% enantiomeric excess (% ee).

In some embodiments, the X4P-001 composition comprises 7000, 6000, 5000, 4500, 4000, 3500, 3000, 2500, 2000, 1750, 1700, 1650, 1600, 1550, 1500, 1450, 1400, or 1350 ppm of toluene or less.

In some embodiments, toluene is used as a crystallization solvent for isolation of X4P-001. In certain embodiments, a specification for residual toluene in X4P-001 freebase is such that the X4P-001 composition comprises no more than 4500 ppm. In other embodiments, the X4P-001 composition comprises no more than 4000 ppm, 3500 ppm, 3000 ppm, 2500 ppm, 2000 ppm, 1750 ppm, 1700 ppm, 1650 ppm, 1600 ppm, 1550 ppm, 1500 ppm, 1450 ppm, 1400 ppm or 1350 ppm of toluene. In some embodiments, a permitted daily exposure (PDE) approach is used. The term permitted daily exposure (PDE) is defined as a pharmaceutically acceptable intake of residual solvents in a drug. See, e.g., *Guidance for Industry: Q3C Impurities: Residual Solvents* published by the Department of Health and Human Services, Food and Drug Administration (FDA).

In some embodiments, the % purity of the X4P-001 composition as measured by HPLC decreases by less than 1% when the X4P-001 composition is stored for three months at 25° C./60% relative humidity.

In some embodiments, the X4P-001 composition further comprises one or more of the following:

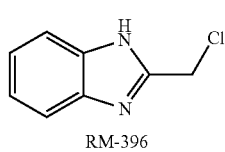

I-8

RM-396

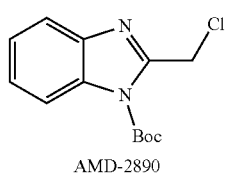

I-9

AMD-2890

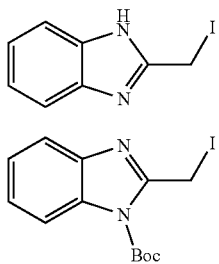

and wherein compound I-8, I-9, I-10 and/or I-11 are present in an amount less than about 25 parts-per-million (ppm) of the X4P-001 composition.

In some embodiments, compound I-8, I-9, I-10 and/or I-11 are present in an amount less than about 50, 40, 30, 20, 15, 10, 5, 4, 3, 2, or 1 ppm of the X4P-001 composition. In some embodiments, compound I-8, I-9, I-10 and/or I-11 are each independently present in an amount between about 1 ppm and about 25 ppm, or between about 100 parts-per-billion (ppb) and 4 ppm. In some embodiments, the X4P-001 composition comprises a compound of formula I, or a pharmaceutically acceptable salt thereof, and does not comprise a compound of formula I-4, or a pharmaceutically acceptable salt thereof, in a detectable amount.

In one aspect, the present invention provides a pharmaceutical composition comprising a disclosed X4P-001 composition and a pharmaceutically acceptable adjuvant, carrier, or vehicle.

In one aspect, the present invention provides a solid unit dosage form formulated for oral administration comprising a disclosed X4P-001 composition or pharmaceutical composition.

In some embodiments, the present invention provides a disclosed X4P-001 composition in combination with an additional therapeutic agent.

In another aspect, the present invention provides a unit dosage form comprising a pharmaceutical composition comprising:
(a) a disclosed X4P-001 composition, in about 10-20% by weight of the composition;
(b) microcrystalline cellulose in about 70-85% by weight of the composition;
(c) croscarmellose sodium in about 5-10% by weight of the composition;
(d) sodium stearyl fumarate in about 0.5-2% by weight of the composition; and
(e) colloidal silicon dioxide in about 0.1-1.0% by weight of the composition.

In another aspect, the present invention provides a unit dosage form comprising a pharmaceutical composition comprising:
(a) a disclosed X4P-001 composition, in about 30-40% by weight of the composition;
(b) microcrystalline cellulose in about 20-25% by weight of the composition;
(c) dibasic calcium phosphate dihydrate in about 30-35% by weight of the composition;
(d) croscarmellose sodium in about 5-10% by weight of the composition;
(e) sodium stearyl fumarate in about 0.5-2% by weight of the composition;
(f) colloidal silicon dioxide in about 0.1-1.0% by weight of the composition; and
(g) sodium lauryl sulfate in about 0.1-1.0% by weight of the composition.

In another aspect, the present invention provides a unit dosage form comprising a pharmaceutical composition comprising:
(a) a disclosed X4P-001 composition, in about 35-75% by weight of the composition;
(b) microcrystalline cellulose in about 5-28% by weight of the composition;
(c) dibasic calcium phosphate dihydrate in about 7-30% by weight of the composition;
(d) croscarmellose sodium in about 2-10% by weight of the composition;
(e) sodium stearyl fumarate in about 0.3-2.5% by weight of the composition;
(f) colloidal silicon dioxide in about 0.05-1.2% by weight of the composition; and
(g) sodium lauryl sulfate in about 0.2-1.2% by weight of the composition.

In some embodiments, the unit dosage form is in the form of a capsule.

In some embodiments, the capsule comprises about 25 mg, about 100 mg, or about 200 mg of X4P-001, or a pharmaceutically acceptable salt thereof.

In another aspect, the present invention provides a method of treating, preventing, or reducing a risk of a disease, disorder, or condition associated with CXCR4 in a subject in need thereof, comprising administering to the subject a disclosed X4P-001 composition.

In some embodiments, the disease, disorder, or condition is cancer.

In some embodiments, the cancer is selected from kidney cancer, renal tumor, renal carcinoma (including clear cell and papillary renal carcinoma), ovarian cancer, or melanoma.

In some embodiments, the X4P-001 composition comprises a compound of formula I, or a pharmaceutically acceptable salt thereof, and one additional compound selected from I-1, I-2, I-3, I-4, I-5, I-6, or I-7; or a pharmaceutically acceptable salt thereof.

In some embodiments, the X4P-001 composition comprises a compound of formula I, or a pharmaceutically acceptable salt thereof, and two additional compounds selected from I-1, I-2, I-3, I-4, I-5, I-6, or I-7; or a pharmaceutically acceptable salt thereof.

In some embodiments, the X4P-001 composition comprises a compound of formula I, or a pharmaceutically acceptable salt thereof, and three additional compounds selected from I-1, I-2, I-3, I-4, I-5, I-6, or I-7; or a pharmaceutically acceptable salt thereof.

In some embodiments, the X4P-001 composition comprises a compound of formula I, or a pharmaceutically acceptable salt thereof, and four additional compounds selected from I-1, I-2, I-3, I-4, I-5, I-6, or I-7; or a pharmaceutically acceptable salt thereof.

In some embodiments, the X4P-001 composition comprises a compound of formula I, or a pharmaceutically acceptable salt thereof, and does not comprise a compound of formula I-4, or a pharmaceutically acceptable salt thereof, in a detectable amount.

In some embodiments, the additional compound or compounds is present in at least a detectable amount.

In some embodiments, the X4P-001 composition comprises a compound of formula I, or a pharmaceutically acceptable salt thereof, and each of I-1, I-2, I-3, I-4, I-5, I-6, or I-7; or a pharmaceutically acceptable salt thereof.

In some embodiments, the X4P-001 composition comprises a compound of formula I, or a pharmaceutically acceptable salt thereof, and I-1, or a pharmaceutically acceptable salt thereof.

In some embodiments, the X4P-001 composition comprises a compound of formula I, or a pharmaceutically acceptable salt thereof, and I-2, or a pharmaceutically acceptable salt thereof.

In some embodiments, the X4P-001 composition comprises a compound of formula I, or a pharmaceutically acceptable salt thereof, and I-3, or a pharmaceutically acceptable salt thereof.

In some embodiments, the X4P-001 composition comprises a compound of formula I, or a pharmaceutically acceptable salt thereof, and I-4, or a pharmaceutically acceptable salt thereof.

In some embodiments, the X4P-001 composition comprises a compound of formula I, or a pharmaceutically acceptable salt thereof, and I-5, or a pharmaceutically acceptable salt thereof.

In some embodiments, the X4P-001 composition comprises a compound of formula I, or a pharmaceutically acceptable salt thereof, and I-6, or a pharmaceutically acceptable salt thereof.

In some embodiments, the X4P-001 composition comprises a compound of formula I, or a pharmaceutically acceptable salt thereof, and I-7, or a pharmaceutically acceptable salt thereof.

In some embodiments, the X4P-001 composition comprises a compound of formula I, or a pharmaceutically acceptable salt thereof; and I-1, I-2, I-3, I-4, I-5, I-6, and I-7; or a pharmaceutically acceptable salt thereof.

In some embodiments, a % w/w amount of a compound in a disclosed X4P-001 composition is measured by comparing the area percentage in an HPLC chromatogram of the compound vs. any other compounds present in the X4P-001 composition. For example, if measured in this manner, 0.2% w/w of compound I-6 present in an X4P-001 composition comprising I-6 and a compound of formula I means that the composition contains 0.2% peak area % of I-6 and 99.8% peak area % by HPLC of the compound of formula I. In other embodiments, the % w/w is measured using another means known to one of ordinary skill in the art, such as those described herein.

In one aspect, the present invention provides a method of preparing a disclosed X4P-001 composition, wherein the composition is prepared substantially as described in the Examples and Figures herein.

In another aspect, the present invention provides a compound selected from these depicted in Table 1, below.

TABLE 1

Representative Compounds of the Present Invention

I-1

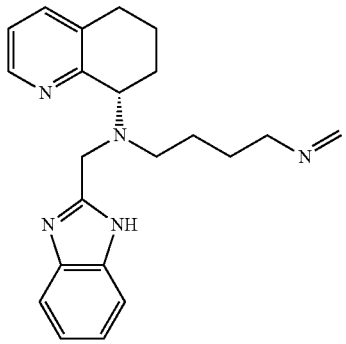 [SMILES: C=NCCCCN(Cc1nc2ccccc2[nH]1)[C@H]1CCCc2cccnc21]

(S)-N-((1H-benzo[d]imidazol-2-yl)methyl)-N-(4-(methyleneamino)butyl)-5,6,7,8-tetrahydroquinolin-8-amine TABLE 1-continued Representative Compounds of the Present Invention

I-2

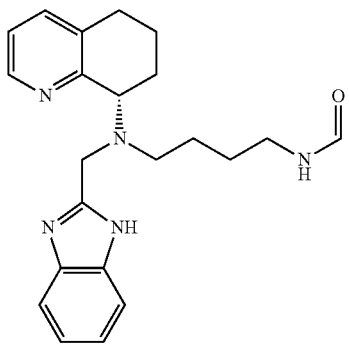 [SMILES: O=CNCCCCN(Cc1nc2ccccc2[nH]1)[C@H]1CCCc2cccnc21]

(S)-N-(4-(((1H-benzo[d]imidazol-2-yl)methyl)(5,6,7,8-tetrahydroquinolin-8-yl)amino)butyl)formamide

I-3

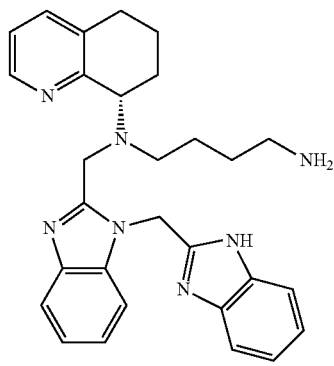 [SMILES: NCCCCN(Cc1nc2ccccc2n1Cc1nc2ccccc2[nH]1)[C@H]1CCCc2cccnc21]

(S)-N$^1$-((1-((1H-benzo[d]imidazol-2-yl)methyl)-1H-benzo[d]imidazol-2-yl)methyl)-N$^1$-(5,6,7,8-tetrahydroquinolin-8-yl)butane-1,4-diamine

I-4

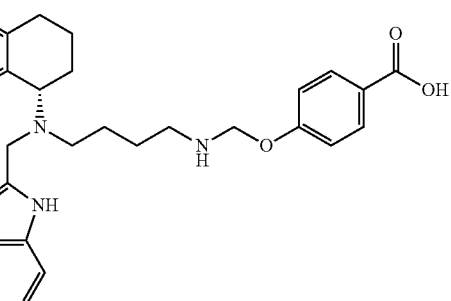

(S)-4-(((4-(((1H-benzo[d]imidazol-2-yl)methyl)(5,6,7,8-tetrahydroquinolin-8-yl)amino)butyl)amino)methoxy)benzoic acid

TABLE 1-continued

Representative Compounds of the Present Invention

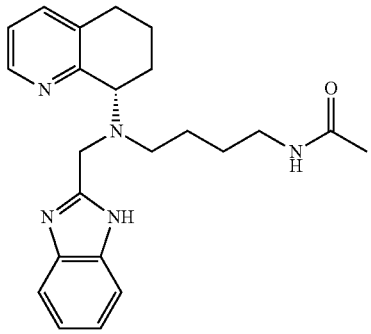 [SMILES: CC(=O)NCCCCN(Cc1nc2ccccc2[nH]1)[C@H]1CCCc2cccnc21]

I-5

(S)-N-(4-(((1H-benzo[d]imidazol-2-yl)methyl)(5,6,7,8-tetrahydroquinolin-8-yl)amino)butyl)acetamide

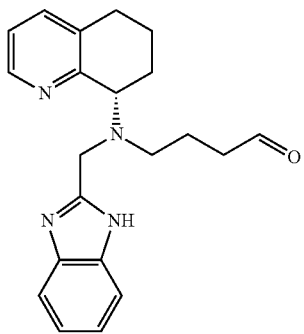 [SMILES: O=CCCCN(Cc1nc2ccccc2[nH]1)[C@H]1CCCc2cccnc21]

I-6

(S)-4-(((1H-benzo[d]imidazol-2-yl)methyl)(5,6,7,8-tetrahydroquinolin-8-yl)amino)butanal

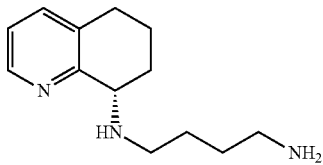 [SMILES: NCCCCN[C@H]1CCCc2cccnc21]

I-7

(S)-$N^1$-(5,6,7,8-tetrahydroquinolin-8-yl)butane-1,4-diamine

In some embodiments, the present invention provides a compound depicted in Table 1, above, or a pharmaceutically acceptable salt thereof.

In some embodiments, the present invention provides a pharmaceutical composition that comprises a compound of formula I, or a pharmaceutically acceptable salt thereof, and at least one of the compounds depicted in Table 1 above or a pharmaceutically acceptable salt thereof. The composition may comprise 1, 2, 3, 4, 5, 6, or 7 of the compounds. In some embodiments, the composition does not comprise compound I-4 in a detectable amount.

Typically, the wt % of each impurity is determined by HPLC, and is measured either initially or after storage, and optionally on an on-going basis during the shelf life of the X4P-001 composition. In some embodiments, the level of an impurity is measured after storage of the composition under stressed conditions, which are conditions of elevated temperature, humidity, or both, used to approximate the effect of long-term storage under ambient conditions.

In some embodiments, the compound of formula I or pharmaceutically acceptable salt thereof is present in the X4P-001 composition in an amount of at least about 96, 97, 97.5, 98, 98.5, 98.7, 98.9, 99.0, 99.1, 99.2, 99.3, 99.4, 99.5, 99.6, 99.7, 99.75, 99.8, 99.85, 99.9, 99.95, 99.97, or 99.999 weight percent where the percentages are based on the free base of the compound and the total weight of the X4P-001 composition. In other embodiments, the X4P-001 composition contains no more than about 2.0 area percent HPLC of total organic impurities or, in other embodiments, no more than about 5.0, 4.0, 2.0, 1.9, 1.8, 1.7, 1.6, 1.5, 1.25, 1, 0.75, 0.5, 0.25, 0.2, 0.1, 0.01, 0.005, or 0.001 area percent HPLC total organic impurities relative to the total area of the HPLC chromatogram.

In other embodiments, the X4P-001 composition contains no more than about 5.0, 4.0, 2.0, 1.9, 1.8, 1.7, 1.6, 1.5, 1.25, 1, 0.75, 0.5, 0.25, 0.2, 0.1, 0.01, 0.005, or 0.001 area percent (measured by HPLC) of compounds I-1, I-2, I-3, I-4, I-5, I-6, and I-7 relative to the total area of the HPLC chromatogram.

In other embodiments, the X4P-001 composition comprises a compound of formula I, or a pharmaceutically acceptable salt thereof, and one or more additional compounds selected from I-1, I-2, I-3, I-4, I-5, I-6, or I-7; or a pharmaceutically acceptable salt thereof, and at least one pharmaceutically acceptable carrier. In some embodiments, the X4P-001 composition contains the compound of formula I or pharmaceutically acceptable salt thereof in an amount of about 1 weight percent to about 99 weight percent, where the percentages are based on the free base of said compound and on the total weight of the X4P-001 composition. In other embodiments, the X4P-001 composition contains no more than about 2.0 area percent HPLC of total organic impurities or, in other embodiments, no more than about 5.0, 4.0, 2.0, 1.9, 1.8, 1.7, 1.6, 1.5, 1.25, 1.1, 1.05, 1, 0.95, 0.9, 0.8, 0.75, 0.7, 0.6, 0.5, 0.25, 0.2, 0.1, 0.01, 0.005, or 0.001 area percent HPLC total organic impurities relative to the total area of the HPLC chromatogram.

In some embodiments, the one or more compounds selected from I-1, I-2, I-3, I-4, I-5, I-6, or I-7; or a pharmaceutically acceptable salt thereof, together or individually comprise about 0.01-0.20 area percent of the HPLC chromatogram relative to the compound of formula I or pharmaceutically acceptable salt thereof. In some embodiments, the one or more compounds selected from I-1, I-2, I-3, I-4, I-5, I-6, or I-7; or a pharmaceutically acceptable salt thereof, together or individually comprise about 0.02-0.18, 0.03-0.16, 0.05-0.15, 0.075-0.13, 0.09-0.1, 0.1-0.2, or 0.15-0.2 area percent of the HPLC chromatogram relative to the compound of formula I or pharmaceutically acceptable salt thereof. In some embodiments, the foregoing area percentages of the HPLC chromatogram are measured relative to the total area of the HPLC chromatogram instead of relative to the peak area of the compound of formula I or pharmaceutically acceptable salt thereof.

In some embodiments, the one or more compounds selected from I-1, I-2, I-3, I-4, I-5, I-6, or I-7; or a pharmaceutically acceptable salt thereof, together or individually comprise less than about 5.0 weight percent (% w/w), or about 0.01-5.0% w/w relative to the compound of formula I or pharmaceutically acceptable salt thereof. In some embodiments, the one or more compounds selected from I-1, I-2, I-3, I-4, I-5, I-6, or I-7; or pharmaceutically acceptable salt thereof, together or individually comprise less than about 3.0% w/w of the X4P-001 composition; or comprise about 0.02-4.0, 0.03-3.5, 0.05-3.1, 0.05-2.9, 0.05-2.5, 0.05-2.0, 0.05-1.8, 0.05-1.6, 0.05-1.5, 0.05-1.4, 0.05-1.2, 0.05-1.1, 0.05-1.0, 0.05-0.9, 0.05-0.8, 0.05-0.7, 0.05-0.6, 0.05-0.5, 0.05-0.4, 0.05-0.3, 0.05-0.2, 0.05-0.1, or about 0.1-0.5% w/w of the X4P-001 composition.

In some embodiments, the total organic impurities, including the one or more compounds selected from I-1, I-2, I-3, I-4, I-5, I-6, or I-7; or a pharmaceutically acceptable salt thereof, comprise less than about 0.05% w/w, about 0.1, 0.5, 1.0, 2.0, 3.0, or about 4.0% w/w or less of the X4P-001 composition. In some embodiments, the total organic impurities comprise about 0.02-4.0, 0.03-3.5, 0.05-3.1, 0.05-2.9, 0.05-2.5, 0.05-2.0, 0.05-1.8, 0.05-1.6, 0.05-1.5, 0.05-1.4, 0.05-1.2, 0.05-1.1, 0.05-1.0, 0.05-0.9, 0.05-0.8, 0.05-0.7, 0.05-0.6, 0.05-0.5, 0.05-0.4, 0.05-0.3, 0.05-0.2, 0.05-0.1, or about 0.1-0.5% w/w of the X4P-001 composition.

In some embodiments, the amount of I-1, or a pharmaceutically acceptable salt thereof, is less than about 1.1%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01% w/w of the X4P-001 composition.

In some embodiments, the amount of I-2, or a pharmaceutically acceptable salt thereof, is less than about 0.3%, 0.2%, 0.1%, 0.09%, 0.08%, 0.07%, 0.06%, 0.05%, 0.04%, 0.03%, 0.02%, or 0.01% w/w of the X4P-001 composition.

In some embodiments, the amount of I-3, or a pharmaceutically acceptable salt thereof, is less than about 0.4%, 0.3%, 0.2%, 0.1%, 0.09%, 0.08%, 0.07%, 0.06%, 0.05%, 0.04%, 0.03%, 0.02%, or 0.01% w/w of the X4P-001 composition.

In some embodiments, the amount of I-4, or a pharmaceutically acceptable salt thereof, is less than about 0.5%, 0.4%, 0.3%, 0.2%, 0.1%, 0.09%, 0.08%, 0.07%, 0.06%, 0.05%, 0.04%, 0.03%, 0.02%, or 0.01% w/w of the X4P-001 composition.

In some embodiments, the amount of I-5, or a pharmaceutically acceptable salt thereof, is less than about 0.5%, 0.4%, 0.3%, 0.2%, 0.1%, 0.09%, 0.08%, 0.07%, 0.06%, 0.05%, 0.04%, 0.03%, 0.02%, or 0.01% w/w of the X4P-001 composition.

In some embodiments, the amount of I-6, or a pharmaceutically acceptable salt thereof, is less than about 0.5%, 0.4%, 0.3%, 0.2%, 0.1%, 0.09%, 0.08%, 0.07%, 0.06%, 0.05%, 0.04%, 0.03%, 0.02%, or 0.01% w/w of the X4P-001 composition.

In some embodiments, the amount of I-7, or a pharmaceutically acceptable salt thereof, is less than about 0.5%, 0.4%, 0.3%, 0.2%, 0.1%, 0.09%, 0.08%, 0.07%, 0.06%, 0.05%, 0.04%, 0.03%, 0.02%, or 0.01% w/w of the X4P-001 composition.

In some embodiments, the amount of I-1, or a pharmaceutically acceptable salt thereof, is from about 0.001 to about 1.1%, about 0.01 to about 1.1%, about 0.01 to about 0.8%, 0.01 to about 0.7%, about 0.01 to about 0.6%, 0.01 to about 0.5%, 0.01 to about 0.4%, 0.01 to about 0.3%, 0.01 to about 0.2%, 0.01 to about 0.1%, 0.01 to about 0.09%, 0.01 to about 0.08%, 0.01 to about 0.07%, 0.01 to about 0.06%, 0.01 to about 0.05%, 0.01 to about 0.03%, or 0.01 to about 0.02% w/w of the X4P-001 composition.

In some embodiments, the amount of I-2, or a pharmaceutically acceptable salt thereof, is from about 0.001 to about 0.3%, about 0.01 to about 0.3%, 0.01 to about 0.2%, 0.01 to about 0.1%, 0.01 to about 0.09%, 0.01 to about 0.08%, 0.01 to about 0.07%, 0.01 to about 0.06%, 0.01 to about 0.05%, 0.01 to about 0.03%, or 0.01 to about 0.02% w/w of the X4P-001 composition.

In some embodiments, the amount of I-3, or a pharmaceutically acceptable salt thereof, is from about 0.001 to about 0.4%, about 0.01 to about 0.4%, about 0.01 to about 0.3%, 0.01 to about 0.2%, 0.01 to about 0.1%, 0.01 to about 0.09%, 0.01 to about 0.08%, 0.01 to about 0.07%, 0.01 to about 0.06%, 0.01 to about 0.05%, 0.01 to about 0.03%, or 0.01 to about 0.02% w/w of the X4P-001 composition.

In some embodiments, the amount of I-4, or a pharmaceutically acceptable salt thereof, is from about 0.001 to about 0.5%, about 0.01 to about 0.5%, about 0.01 to about 0.3%, 0.01 to about 0.2%, 0.01 to about 0.1%, 0.01 to about 0.09%, 0.01 to about 0.08%, 0.01 to about 0.07%, 0.01 to about 0.06%, 0.01 to about 0.05%, 0.01 to about 0.03%, or 0.01 to about 0.02% w/w of the X4P-001 composition.

In some embodiments, the amount of I-5, or a pharmaceutically acceptable salt thereof, is from about 0.001 to about 0.5%, about 0.01 to about 0.5%, about 0.01 to about 0.4%, about 0.01 to about 0.3%, 0.01 to about 0.2%, 0.01 to about 0.1%, 0.01 to about 0.09%, 0.01 to about 0.08%, 0.01 to about 0.07%, 0.01 to about 0.06%, 0.01 to about 0.05%, 0.01 to about 0.03%, or 0.01 to about 0.02% w/w of the X4P-001 composition.

In some embodiments, the amount of I-6, or a pharmaceutically acceptable salt thereof, is from about 0.001 to about 0.5%, about 0.01 to about 0.5%, about 0.01 to about 0.4%, about 0.01 to about 0.3%, 0.01 to about 0.2%, 0.01 to about 0.1%, 0.01 to about 0.09%, 0.01 to about 0.08%, 0.01 to about 0.07%, 0.01 to about 0.06%, 0.01 to about 0.05%, 0.01 to about 0.03%, or 0.01 to about 0.02% w/w of the X4P-001 composition.

In some embodiments, the amount of I-7, or a pharmaceutically acceptable salt thereof, is from about 0.001 to about 0.5%, about 0.01 to about 0.5%, about 0.01 to about 0.4%, about 0.01 to about 0.3%, 0.01 to about 0.2%, 0.01 to about 0.1%, 0.01 to about 0.09%, 0.01 to about 0.08%, 0.01 to about 0.07%, 0.01 to about 0.06%, 0.01 to about 0.05%, 0.01 to about 0.03%, or 0.01 to about 0.02% w/w of the X4P-001 composition.

In some embodiments, the amount of any additional or unknown impurities in the X4P-001 composition is from about 0.01 to about 0.2% w/w of the composition.

In some embodiments, the amount of p-hydroxybenzoic acid present in the X4P-001 composition is from about 0.01 to about 0.5% w/w of the composition. In some embodiments, the composition is substantially free of p-hydroxybenzoic acid. In some embodiments, p-hydroxybenzoic acid is not present in the composition in a detectable amount. In some embodiments, the X4P-001 composition comprises a compound of formula I, or a pharmaceutically acceptable salt thereof, and does not comprise a compound of formula I-4, or a pharmaceutically acceptable salt thereof, in a detectable amount.

In some embodiments, the chiral purity of the X4P-001 composition is at least about 97% enantiomeric excess (% ee). In some embodiments, the chiral purity of the compound of formula I is at least 97% ee. In some embodiments, the chiral purity of the compound of formula I is at least 98% ee. In some embodiments, the chiral purity of the compound of formula I is at least 99% ee. In some embodiments, the chiral purity of the compound of formula I is at least 99.1, 99.2, 99.3, 99.4, 99.5, 99.6, 99.7, 99.8, or 99.9% ee.

In some embodiments, the present invention provides any compound described above and herein in isolated form. As used herein, the term "isolated" means that a compound is provided in a form that is separated from other components that might be present in that compound's usual environment. In certain embodiments, an isolated compound is in solid form. In some embodiments, an isolated compound is at least about 50% pure as determined by a suitable HPLC method. In certain embodiments, an isolated compound is at least about 60%, 70%, 80%, 90%, 95%, 98%, 99%, 99.5%, 99.6%, 99.7%, 99.8%, 99.9%, 99.95%, 99.99%, or 99.999% pure as determined by a suitable HPLC method. Percent purity may be measured by weight percent of the desired compound (% w/w), by area % relative to the total area of the HPLC chromatogram, or by other methods known in the art.

Methods of preparation and analysis applicable to certain compounds of the invention are disclosed in U.S. Pat. No. 7,354,934, WO 00/56729, U.S. Ser. No. 60/232,891, and U.S. Ser. No. 60/234,510, as well as An, H.; Wang, T.; Mohan, V.; Griffey, R. H.; Cook, P. D. *Tetrahedron* 1998, 54, 3999-4012; the entire contents of each of which is hereby incorporated by reference.

Disclosed compounds may be purified by any means known in the art. Such means include, e.g. silica gel column chromatography; medium pressure liquid chromatography (MPLC); high pressure liquid chromatography (HPLC); preparative HPLC (prep-HPLC); flash chromatography (FC); liquid chromatography (LC); supercritical fluid chromatography (SFC); thin layer chromatography (TLC); preparative TLC (prep-TLC); liquid chromatography-mass spectrometry (LC-MS, LCMS or LC/MS); recrystallization; precipitation; trituration; distillation; derivitization; acid-base extraction; and the like.

The term "purified," "in purified form," or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer or stereoisomer thereof, or pharmaceutically acceptable salt or solvate of said compound, said stereoisomer, or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

The term "detectable amount," as used herein, refers to a component present in a sample, for example a sample of a disclosed X4P-001 composition, that is present at least in an amount that is capable of being detected by analytical means known in the art. For example, in some embodiments, a "detectable amount" is at least an amount detectable by HPLC, LC-MS, mass spectrometry, NMR, or other analytical methods known to one of ordinary skill in the art or described herein.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of chiral HPLC column.

4. Uses, Formulation, and Administration

Pharmaceutically Acceptable Compositions

In one aspect, the invention provides an X4P-001 composition comprising a disclosed compound, pharmaceutically acceptable salt, or pharmaceutically acceptable derivative; or a disclosed X4P-001 composition; and a pharmaceutically acceptable excipient, carrier, adjuvant, or vehicle. The amount of compound in compositions of this invention is such that is effective to measurably inhibit CXCR4, or a mutant thereof, in a biological sample or in a patient. In certain embodiments, the amount of compound in compositions of this invention is such that is effective to measurably inhibit CXCR4, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of CXCR4, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

The compounds and compositions, according to the method of the present invention, may be administered using any amount and any route of administration effective for treating or lessening the severity of a cancer, an autoimmune disorder, a primary immune deficiency, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. In some embodiments, compounds of the invention are formulated in dosage unit form for ease of administration and uniformity of dosage.

The term "patient" or "subject" as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg or, e.g., from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In certain embodiments, the composition is formulated for oral administration in the form of a tablet or a capsule. In some embodiments, the composition comprising X4P-001 is formulated for oral administration in the form of a capsule.

In certain embodiments, a provided method comprises administering to the patient one or more capsules comprising 10 mg to 1200 mg X4P-001 active ingredient; and one or more pharmaceutically acceptable excipients. In certain embodiments, the capsule is comprised of hard gelatin.

In certain embodiments, the present invention provides a pharmaceutical composition comprising an X4P-001 composition, one or more diluents, a disintegrant, a lubricant, a flow aid, and a wetting agent. In some embodiments, the present invention provides a pharmaceutical composition comprising 10 mg to 1200 mg of an X4P-001 composition, microcrystalline cellulose, dibasic calcium phosphate dihydrate, croscarmellose sodium, sodium stearyl fumarate, colloidal silicon dioxide, and sodium lauryl sulfate. In some embodiments, the present invention provides a unit dosage form wherein said unit dosage form comprises a pharmaceutical composition comprising 10-200 mg of an X4P-001 composition, microcrystalline cellulose, dibasic calcium phosphate dihydrate, croscarmellose sodium, sodium stearyl fumarate, colloidal silicon dioxide, and sodium lauryl sulfate. In certain embodiments, the present invention provides a unit dosage form comprising a pharmaceutical composition comprising an X4P-001 composition, present in an amount of about 10 mg, about 20 mg, about 25 mg, about 50 mg, about 75 mg, about 100 mg, about 150 mg, about 200 mg, about 250 mg, about 300 mg, about 400 mg, about 450 mg, about 500 mg, about 600 mg, about 700 mg, about 750 mg, about 800 mg, about 900 mg, about 1000 mg, about 1100 mg, or about 1200 mg. In some embodiments, a provided composition (or unit dosage form) is administered to the patient once per day, twice per day, three times per day, or four times per day. In some embodiments, a provided composition (or unit dosage form) is administered to the patient once per day or twice per day.

In some embodiments, the present invention provides a pharmaceutical composition comprising:
  (a) a disclosed X4P-001 composition, representing about 30-40% by weight of the composition;
  (b) microcrystalline cellulose in about 20-25% by weight of the composition;
  (c) dibasic calcium phosphate dihydrate in about 30-35% by weight of the composition;
  (d) croscarmellose sodium in about 5-10% by weight of the composition;
  (e) sodium stearyl fumarate in about 0.5-2% by weight of the composition;
  (f) colloidal silicon dioxide in about 0.1-1.0% by weight of the composition; and
  (g) sodium lauryl sulfate in about 0.1-1.0% by weight of the composition.

In some embodiments, the present invention provides a pharmaceutical composition comprising:
  (a) a disclosed X4P-001 composition, representing about 8-25% by weight of the composition;
  (b) microcrystalline cellulose in about 65-85% by weight of the composition;
  (c) croscarmellose sodium in about 2-10% by weight of the composition;
  (d) sodium stearyl fumarate in about 0.1-3% by weight of the composition; and
  (e) colloidal silicon dioxide in about 0.05-0.7% by weight of the composition.

In some embodiments, the present invention provides a pharmaceutical composition comprising:
  (a) a disclosed X4P-001 composition, representing about 25-45% by weight of the composition;
  (b) microcrystalline cellulose in about 10-35% by weight of the composition;
  (c) dibasic calcium phosphate dihydrate in about 15-45% by weight of the composition;
  (d) croscarmellose sodium in about 2-10% by weight of the composition;
  (e) sodium stearyl fumarate in about 0.3-2.5% by weight of the composition;
  (f) colloidal silicon dioxide in about 0.05-1.2% by weight of the composition; and
  (g) sodium lauryl sulfate in about 0.2-1.2% by weight of the composition.

In some embodiments, the present invention provides a pharmaceutical composition comprising:
  (a) a disclosed X4P-001 composition, representing about 35-75% by weight of the composition;
  (b) microcrystalline cellulose in about 5-28% by weight of the composition;
  (c) dibasic calcium phosphate dihydrate in about 7-30% by weight of the composition;
  (d) croscarmellose sodium in about 2-10% by weight of the composition;
  (e) sodium stearyl fumarate in about 0.3-2.5% by weight of the composition;
  (f) colloidal silicon dioxide in about 0.05-1.2% by weight of the composition; and
  (g) sodium lauryl sulfate in about 0.2-1.2% by weight of the composition.

In some embodiments, the X4P-001 composition is present in an amount of about 10 mg, about 20 mg, about 25 mg, about 50 mg, about 75 mg, about 100 mg, about 150 mg, about 200 mg, about 250 mg, about 300 mg, about 400 mg, about 450 mg, about 500 mg, about 600 mg, about 700 mg, about 750 mg, about 800 mg, about 900 mg, about 1000 mg, about 1100 mg, or about 1200 mg.

In some embodiments, the composition comprises about 37 wt % of a disclosed X4P-001 composition.

In some embodiments, the present invention provides a unit dosage form comprising a disclosed X4P-001 composition or pharmaceutical composition.

In some embodiments, the present invention provides a unit dosage form comprising a pharmaceutical composition comprising:
  (a) a disclosed X4P-001 composition, in about 10-30% by weight of the composition;
  (b) microcrystalline cellulose in about 60-80% by weight of the composition;
  (c) croscarmellose sodium in about 5-10% by weight of the composition;
  (d) sodium stearyl fumarate in about 0.5-2% by weight of the composition; and
  (e) colloidal silicon dioxide in about 0.1-1.0% by weight of the composition.

In some embodiments, the present invention provides a unit dosage form comprising a pharmaceutical composition comprising:
  (a) a disclosed X4P-001 composition, in about 14.7% by weight of the composition;
  (b) microcrystalline cellulose in about 78.1% by weight of the composition;
  (c) croscarmellose sodium in about 6.0% by weight of the composition;
  (d) sodium stearyl fumarate in about 1.0% by weight of the composition; and
  (e) colloidal silicon dioxide in about 0.2% by weight of the composition.

In some embodiments, the present invention provides a unit dosage form comprising a pharmaceutical composition comprising:

(a) a disclosed X4P-001 composition in about 10-20% by weight of the composition;
(b) microcrystalline cellulose in about 25-40% by weight of the composition;
(c) dibasic calcium phosphate dihydrate in about 35-55% by weight of the composition;
(d) croscarmellose sodium in about 4-15% by weight of the composition;
(e) sodium stearyl fumarate in about 0.3-2% by weight of the composition;
(f) colloidal silicon dioxide in about 0.1-1.5% by weight of the composition; and
(g) sodium lauryl sulfate in about 0.1-1.5% by weight of the composition.

In some embodiments, the present invention provides a unit dosage form comprising a pharmaceutical composition comprising:
(a) a disclosed X4P-001 composition, in about 12.85% by weight of the composition;
(b) microcrystalline cellulose in about 31.92% by weight of the composition;
(c) dibasic calcium phosphate dihydrate in about 44.4% by weight of the composition;
(d) croscarmellose sodium in about 8.33% by weight of the composition;
(e) sodium stearyl fumarate in about 1.38% by weight of the composition;
(f) colloidal silicon dioxide in about 0.42% by weight of the composition; and
(g) sodium lauryl sulfate in about 0.7% by weight of the composition.

International Patent Application No. PCT/US2016/066634 describes additional compositions and methods of use of X4P-001, and is incorporated by reference in its entirety.

Inasmuch as it may be desirable to administer a combination of active compounds, for example, for the purpose of treating a particular disease or condition, it is within the scope of the present invention that two or more pharmaceutical compositions, at least one of which contains a composition in accordance with the invention, may conveniently be combined in the form of a kit suitable for co-administration of the compositions. Thus the kit of the invention includes two or more separate pharmaceutical compositions, at least one of which contains an X4P-001 composition of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

Uses of Compounds and Pharmaceutically Acceptable Compositions

It has been discovered that certain impurities arise during the synthesis of X4P-001 such as the compounds shown in Table 1, above, or a stereoisomer or pharmaceutically acceptable salt thereof. Isolation and characterization of each impurity is useful for a number of purposes. Generally, pharmaceutical compositions require a high level of purity to meet regulated standards for drug quality and purity. For example, in the synthesis of X4P-001, impurities are often formed, including degradants or by-products of manufacture, which may hinder the therapeutic effects of X4P-001 and/or may be toxic if present in high enough quantities. As such, it is desirable to have the ability to determine the presence and amounts of such impurities and to monitor the chemical purity, including stereochemical purity, of X4P-001. To do this, it is important to identify, isolate, and chemically characterize impurities, which can be used in chromatographic procedures as standards to confirm the purity of X4P-001.

Accordingly, in one aspect, the present invention provides a method of preparing a disclosed compound, or a pharmaceutically acceptable salt thereof, comprising contacting an appropriate starting material or materials under conditions shown, e.g., in the Examples below, to prepare the compound or pharmaceutically acceptable salt thereof. In some embodiments, the compound or pharmaceutically acceptable salt thereof is useful as a reference standard and/or in methods of determining the presence of an impurity in a sample, such as a sample of a compound of formula I, or a pharmaceutically acceptable salt thereof.

The present invention also provides methods for determining an impurity, comprising injecting a reference solution comprising a compound of formula I, or a pharmaceutically acceptable salt thereof, into an HPLC column under a set of conditions to obtain a first HPLC chromatogram, wherein the amount and/or chemical identity of the compound present in the reference solution is known; injecting a sample solution comprising a compound of formula I, or a pharmaceutically acceptable salt thereof, into the HPLC column under said set of conditions to obtain a second HPLC chromatogram; and determining the presence and/or the amount of the compound in the sample solution. In some embodiments, the reference solution is injected multiple times. In some embodiments, the determining comprises comparing retention times of peaks in the first HPLC chromatogram and peaks in the second HPLC chromatogram to determine the presence of the compound in the sample solution. In other embodiments, the determining comprises quantifying peak areas of the sample solution and peak areas of the reference solution on the HPLC chromatograms and estimating from these the amount of the compound in the sample solution. In some embodiments, the HPLC column is a reverse phase column and the column is eluted using a mobile phase comprising water, methanol, trifluoroacetic acid, or mixtures thereof.

The present invention also provides methods for determining the presence or amount of an impurity in a sample comprising or consisting essentially of a compound of formula I, or a pharmaceutically acceptable salt thereof, comprising injecting into an HPLC column, in a single or series of injections, a sample solution containing the material and spiked with a reference compound having a known chemical structure such as compound I-1, I-2, I-3, I-4, I-5, I-6, or I-7; obtaining an HPLC chromatogram; and determining the presence and/or the amount of the compound in the material. In some embodiments, the HPLC column is a reverse phase column and the column is eluted using a mobile phase comprising water, methanol, trifluoroacetic acid, or mixtures thereof. The method may further comprise documenting in a written form the chemical identity of the compound and the amount of the compound as an impurity.

In some embodiments, the method further comprises documenting in a written form the chemical identity of the compound and the amount of the compound as an impurity in the material. In some cases, the amount in the material of the compound is determined by (i) identifying a peak on the chromatogram that corresponds to a peak on a control chromatogram of a compound known to have the structure of I-1, I-2, I-3, I-4, I-5, I-6, or I-7; (ii) identifying a peak on the chromatogram that corresponds to a relative retention time of a compound known to have the structure of I-1, I-2, I-3, I-4, I-5, I-6, or I-7; and/or (iii) identifying a peak on the chromatogram that corresponds to a known amount of a spike of the compound known to have the structure of I-1, I-2, I-3, I-4, I-5, I-6, or I-7. In some embodiments, the HPLC column is a reverse phase column and the column is eluted using a mobile phase comprising water, methanol, trifluoroacetic acid, or mixtures thereof.

In some embodiments, the present invention provides a compound selected from I-1, I-2, I-3, I-4, I-5, I-6, or I-7; or a pharmaceutically acceptable salt thereof, in sufficient purity in order to enable its use as a reference or standard in various analytical methods (e.g., HPLC, GC, SFC, LCMS), as described more fully below. In some embodiments, the compound or pharmaceutically acceptable salt thereof may be isolated with at least 0.5% purity, at least 1% purity, at least 5% purity, at least 10% purity, at least 15% purity, at least 25% purity, at least 50% purity, at least 75% purity, at least 95% purity, or with at least 97% purity. In some embodiments, the compound or pharmaceutically acceptable salt thereof is isolated and/or packaged as a solid.

In another aspect, the present invention provides methods for determining the presence and/or amount of I-1, I-2, I-3, I-4, I-5, I-6, or I-7; or a pharmaceutically acceptable salt thereof. For example, the compound or a pharmaceutically acceptable salt thereof may be formed as an impurity during the synthesis of X4P-001. As used herein, the term "impurity" may refer to degradants which arise during storage of X4P-001 and/or by-products formed in a chemical reaction for manufacturing of X4P-001. In one embodiment, the method comprises injecting a reference solution comprising I-1, I-2, I-3, I-4, I-5, I-6, or I-7; or a pharmaceutically acceptable salt thereof, into an HPLC column under a set of conditions to obtain a first HPLC chromatogram wherein the amount and/or chemical identity of I-1, I-2, I-3, I-4, I-5, I-6, or I-7; or a pharmaceutically acceptable salt thereof, present in the reference solution is known, injecting a sample solution comprising X4P-001 into the HPLC column under the same set of conditions to obtain a second HPLC chromatogram, and comparing the first HPLC chromatogram with the second HPLC chromatogram to determine the presence and/or amount of the impurity (I-1, I-2, I-3, I-4, I-5, I-6, or I-7; or a pharmaceutically acceptable salt thereof). The reference solution may be formed by dissolving a sample (e.g., solid sample) of I-1, I-2, I-3, I-4, I-5, I-6, or I-7; or a pharmaceutically acceptable salt thereof, in a first solvent, and the sample solution may be formed by dissolving a solid sample in a second solvent. In some embodiments, the reference solution may contain an additional compound(s), wherein the amount and/or identity of the additional compound(s) is also known. In one embodiment, the sample (e.g., sample solution) may comprise X4P-001. It should be understood that the invention may encompass other samples suspected of containing a compound selected from I-1, I-2, I-3, I-4, I-5, I-6, or I-7; or a pharmaceutically acceptable salt thereof.

In one embodiment, the presence of I-1, I-2, I-3, I-4, I-5, I-6, or I-7; or a pharmaceutically acceptable salt thereof, in the sample solution may be determined by comparing retention times of peaks in the first HPLC chromatogram with the retention times of peaks in the second HPLC chromatogram. For example, the standard solution comprising I-1, I-2, I-3, I-4, I-5, I-6, or I-7; or a pharmaceutically acceptable salt thereof, may produce a chromatogram with a peak corresponding to I-1, I-2, I-3, I-4, I-5, I-6, or I-7; or a pharmaceutically acceptable salt thereof, and having a particular retention time. A sample solution may then be injected into the HPLC column under the same conditions as the standard solution, and the resulting chromatogram may be studied to determine if a peak exists at the same retention time as the peak corresponding to I-1, I-2, I-3, I-4, I-5, I-6, or I-7; or a pharmaceutically acceptable salt thereof, in the HPLC chromatogram of the standard solution. The existence of such a peak can indicate that I-1, I-2, I-3, I-4, I-5, I-6, or I-7; or a pharmaceutically acceptable salt thereof, is present in the sample. In another embodiment, the amount of I-1, I-2, I-3, I-4, I-5, I-6, or I-7; or a pharmaceutically acceptable salt thereof, in the sample solution may be determined by comparing the area of peaks in the first HPLC chromatogram with the area of peaks in the second HPLC chromatogram, and calculating from these the content of I-1, I-2, I-3, I-4, I-5, I-6, or I-7; or a pharmaceutically acceptable salt thereof, in the sample solution.

In some embodiments, the present invention provides methods for determining an impurity in a material consisting essentially of X4P-001, wherein a sample solution containing the material and spiked with a reference compound having a known chemical structure of I-1, I-2, I-3, I-4, I-5, I-6, or I-7; or a pharmaceutically acceptable salt thereof, as described herein, is injected into an HPLC column and an HPLC chromatogram is obtained to determine the presence and/or the amount of the compound in the material.

Methods of the invention may further comprise documenting in a written form the chemical identity of the compound and the amount of the compound as an impurity in the material.

In other embodiments, the present invention provides methods for determining an impurity in a material consisting essentially of X4P-001, wherein a solution in which the material is dissolved is injected into an HPLC column and an HPLC chromatogram is obtained to determine the amount in the material of a compound known to have the structure of I-1, I-2, I-3, I-4, I-5, I-6, or I-7; or a pharmaceutically acceptable salt thereof, as described herein. The chemical identity of the compound and the amount of the compound as an impurity in the material may then be documented. The amount in the material of the compound may be determined by (i) identifying a peak on the chromatogram that corresponds to a peak on a control chromatogram, (ii) identifying a peak on the chromatogram that corresponds to a relative retention time of a compound known to have the structure of I-1, I-2, I-3, I-4, I-5, I-6, or I-7; or pharmaceutically acceptable salt thereof, and/or (iii) identifying a peak on the chromatogram that corresponds to a known amount of a spike of the compound known to have the structure of I-1, I-2, I-3, I-4, I-5, I-6, or I-7; or a pharmaceutically acceptable salt thereof.

Some embodiments of the invention may be useful in determining the amount and/or presence of I-1, I-2, I-3, I-4, I-5, I-6, or I-7; or a pharmaceutically acceptable salt thereof, in a sample comprising X4P-001. The sample may be a sample of freshly manufactured material or the sample may be one stored for a given period of time. In one embodiment, a sample of X4P-001 may be stored and periodically analyzed using methods described herein to determine the presence and/or amount of I-1, I-2, I-3, I-4, I-5, I-6, or I-7; or a pharmaceutically acceptable salt thereof, in the sample which may have been formed by, for example, degradation of X4P-001. In some cases, the sample may be placed under stressed conditions, i.e. conditions to intentionally promote degradation of X4P-001 such as elevated temperatures and/or elevated humidity, wherein the sample is periodically analyzed using methods described herein to determine the presence and/or amount of I-1, I-2, I-3, I-4, I-5, I-6, or I-7; or a pharmaceutically acceptable salt thereof, in the sample.

Compounds and compositions described herein are generally useful for the inhibition of CXCR4 or a mutant thereof. Certain compounds and compositions described herein are found to be useful in treatment, prevention, and/or reduction of a risk of a disease, disorder, or condition associated with CXCR4.

In one aspect, the present invention provides a method of inhibiting CXCR4, or a mutant thereof, activity in a patient comprising the step of administering to said patient a disclosed X4P-001 composition. In other embodiments, the present invention provides a method for treating a disorder mediated by CXCR4, or a mutant thereof, in a patient in need thereof, comprising the step of administering to said patient a disclosed X4P-001 composition according to the present invention or a pharmaceutically acceptable composition thereof. Such disorders are described in detail herein.

Certain methods of treating a disease or disorder with X4P-001 are described in PCT Application No. PCT/US2018/038776, filed Jun. 21, 2018, the entirety of which is hereby incorporated by reference. The presently disclosed compounds and compositions are applicable in such methods of treating a disease or disorder.

In certain embodiments, the composition containing X4P-001, or a pharmaceutically acceptable salt thereof, is administered orally, in an amount from about 200 mg to about 1200 mg daily. In certain embodiments, the dosage composition may be provided twice a day in divided dosage, approximately 12 hours apart. In other embodiments, the dosage composition may be provided once daily. The terminal half-life of X4P-001 has been generally determined to be between about 12 to about 24 hours, or approximately 14.5 hrs. Dosage for oral administration may be from about 100 mg to about 1200 mg once or twice per day. In certain embodiments, the dosage of X4P-0001, or a pharmaceutically acceptable salt thereof, useful in the invention is from about 200 mg to about 800 mg daily. In other embodiments, the dosage of X4P-001, or a pharmaceutically acceptable salt thereof, useful in the invention may range from about 200 mg to about 600 mg, from about 400 mg to about 800 mg, from about 600 mg to about 1000 mg or from about 800 mg to about 1200 mg daily.

In one aspect, the present invention provides a method of treating a cancer, such as those described herein, by administering to a patient in need thereof an effective amount of a disclosed X4P-001 composition. In some embodiments, the method includes co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound or composition and the additional therapeutic agent or agents acts synergistically to prevent or reduce immune escape and/or angiogenic escape of the cancer. In some embodiments, the patient has previously been administered another anticancer agent, such as an adjuvant therapy or immunotherapy. In some embodiments, the cancer is refractory.

In some embodiments, the disease, disorder, or condition associated with CXCR4 is selected from cellular proliferative disorders, Alzheimer's disease, HIV, rheumatoid arthritis, or pulmonary fibrosis. In some embodiments, the disease, disorder, or conditions is a hyperproliferative disorder such as cancer. In some embodiments, the cancer is breast, ovarian, renal, lung cancer, or melanoma. In some embodiments, the cancer is selected from renal cell carcinoma (RCC), refractory RCC, or clear cell RCC (ccRCC).

In some embodiments, the present invention provides a method for treating patients with cancer that presents as a solid tumor. In some embodiments, the patient has kidney cancer, renal tumor, renal carcinoma (including clear cell and papillary renal carcinoma), ovarian cancer, or melanoma.

Provided compounds are inhibitors of CXCR4 and are therefore useful for treating one or more disorders associated with activity of CXCR4. Thus, in certain embodiments, the present invention provides a method for treating a CXCR4-mediated disorder comprising the step of administering to a patient in need thereof a disclosed X4P-001 composition, or pharmaceutically acceptable composition thereof.

In one aspect, the present invention provides a method of treating cancer in a patient in need thereof, wherein said method comprises administering to said patient a disclosed X4P-001 composition in combination with one or more additional therapeutic agents, such as one or more immunostimulatory therapeutic compounds.

In some embodiments, the one or more immunostimulatory therapeutic compounds are selected from elotuzumab, mifamurtide, an agonist or activator of a toll-like receptor, or an activator of RORγt.

In some embodiments, the method further comprises administering to said patient a third therapeutic agent, such as an immune checkpoint inhibitor. In some embodiments, the method comprises administering to the patient in need thereof three therapeutic agents selected from a disclosed X4P-001 composition, an immunostimulatory therapeutic compound, and an immune checkpoint inhibitor.

In some embodiments, the immune checkpoint inhibitor is selected from nivolumab, pembrolizumab, ipilimumab, avelumab, durvalumab, atezolizumab, or pidilizumab.

In another aspect, the present invention provides a method of treating cancer in a patient in need thereof, wherein said method comprises administering to said patient a disclosed X4P-001 composition in combination with one or more additional therapeutic agents selected from an indoleamine (2,3)-dioxygenase (IDO) inhibitor, a Poly ADP ribose polymerase (PARP) inhibitor, a histone deacetylase (HDAC) inhibitor, a CDK4/CDK6 inhibitor, or a phosphatidylinositol 3 kinase (PI3K) inhibitor.

In some embodiments, the IDO inhibitor is selected from epacadostat, indoximod, capmanitib, GDC-0919, PF-06840003, BMS:F001287, Phy906/KD108, or an enzyme that breaks down kynurenine.

In some embodiments, the PARP inhibitor is selected from olaparib, rucaparib, or niraparib.

In some embodiments, the HDAC inhibitor is selected from vorinostat, romidepsin, panobinostat, belinostat, entinostat, or chidamide.

In some embodiments, the CDK 4/6 inhibitor is selected from palbociclib, ribociclib, abemaciclib or trilaciclib.

In some embodiments, the method further comprises administering to said patient a third therapeutic agent, such as an immune checkpoint inhibitor. In some embodiments, the method comprises administering to the patient in need thereof three therapeutic agents selected from a disclosed X4P-001 composition, a second therapeutic agent selected from an indoleamine (2,3)-dioxygenase (IDO) inhibitor, a Poly ADP ribose polymerase (PARP) inhibitor, a histone deacetylase (HDAC) inhibitor, a CDK4/CDK6 inhibitor, or a phosphatidylinositol 3 kinase (PI3K) inhibitor, and a third therapeutic agent selected from an immune checkpoint inhibitor. In some embodiments, the immune checkpoint inhibitor is selected from nivolumab, pembrolizumab, ipilimumab, avelumab, durvalumab, atezolizumab, or pidilizumab.

In some embodiments, the PI3K inhibitor is selected from idelalisib, alpelisib, taselisib, pictilisib, copanlisib, duvelisib, PQR309, or TGR1202.

In another aspect, the present invention provides a method of treating cancer in a patient in need thereof, wherein said method comprises administering to said patient a disclosed X4P-001 composition in combination with one or more additional therapeutic agents selected from a platinum-based therapeutic, a taxane, a nucleoside inhibitor, or a therapeutic agent that interferes with normal DNA synthesis, protein synthesis, cell replication, or will otherwise inhibit rapidly proliferating cells.

In some embodiments, the platinum-based therapeutic is selected from cisplatin, carboplatin, oxaliplatin, nedaplatin, picoplatin, or satraplatin.

In some embodiments, the taxane is selected from paclitaxel, docetaxel, albumin-bound paclitaxel, cabazitaxel, or SID530.

In some embodiments, the therapeutic agent that interferes with normal DNA synthesis, protein synthesis, cell replication, or will otherwise interfere with the replication of rapidly proliferating cells is selected from trabectedin, mechlorethamine, vincristine, temozolomide, cytarabine, lomustine, azacitidine, omacetaxine mepesuccinate, asparaginase *Envinia chrysanthemi*, eribulin mesylate, capacetrine, bendamustine, ixabepilone, nelarabine, clorafabine, trifluridine, or tipiracil.

In some embodiments, the method further comprises administering to said patient a third therapeutic agent, such as an immune checkpoint inhibitor. In some embodiments, the method comprises administering to the patient in need thereof three therapeutic agents selected from a disclosed X4P-001 composition, a second therapeutic agent selected from a platinum-based therapeutic, a taxane, a nucleoside inhibitor, or a therapeutic agent that interferes with normal DNA synthesis, protein synthesis, cell replication, or will otherwise inhibit rapidly proliferating cells, and a third therapeutic agent selected from an immune checkpoint inhibitor.

In some embodiments, the immune checkpoint inhibitor is selected from nivolumab, pembrolizumab, ipilimumab, avelumab, durvalumab, atezolizumab, or pidilizumab.

In some embodiments, any one of the foregoing methods further comprises the step of obtaining a biological sample from the patient and measuring the amount of a disease-related biomarker.

In some embodiments, the biological sample is a blood sample.

In some embodiments, the disease-related biomarker is selected from circulating CD8+ T cells or the ratio of CD8+ T cells: Treg cells.

In some embodiments, the cancer is selected from hepatocellular carcinoma, ovarian cancer, ovarian epithelial cancer, fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical adenoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from hepatocellular carcinoma (HCC), hepatoblastoma, colon cancer, rectal cancer, ovarian cancer, ovarian epithelial cancer, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical adenoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the present invention provides a method for treating a cancer that presents as a solid tumor, such as a sarcoma, carcinoma, or lymphoma, comprising the step of administering a disclosed X4P-001 composition to a patient in need thereof. Solid tumors generally comprise an abnormal mass of tissue that typically does not include cysts or liquid areas. In some embodiments, the cancer is selected from renal cell carcinoma, or kidney cancer; hepatocellular carcinoma (HCC) or hepatoblastoma, or liver cancer; melanoma; breast cancer; colorectal carcinoma, or colorectal cancer; colon cancer; rectal cancer; anal cancer; lung cancer, such as non-small cell lung cancer (NSCLC) or small cell lung cancer (SCLC); ovarian cancer, ovarian epithelial cancer, ovarian carcinoma, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical carcinoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from renal cell carcinoma, hepatocellular carcinoma (HCC), hepatoblastoma, colorectal carcinoma, colorectal cancer, colon cancer, rectal cancer, anal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, chondrosarcoma, anaplastic thyroid cancer, adrenocortical carcinoma, pancreatic cancer, pancreatic ductal carcinoma, pancreatic adenocarcinoma, glioma, brain cancer, neurofibromatosis-1 associated malignant peripheral nerve sheath tumors (MPNST), Waldenstrom's macroglobulinemia, or medulloblastoma.

In some embodiments, the cancer is selected from hepatocellular carcinoma (HCC), hepatoblastoma, colon cancer, rectal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical carcinoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the cancer is hepatocellular carcinoma (HCC). In some embodiments, the cancer is hepatoblastoma. In some embodiments, the cancer is colon cancer. In some embodiments, the cancer is rectal cancer. In some embodiments, the cancer is ovarian cancer, or ovarian carcinoma. In some embodiments, the cancer is ovarian epithelial cancer. In some embodiments, the cancer is fallopian tube cancer. In some embodiments, the cancer is papillary serous cystadenocarcinoma. In some embodiments, the cancer is uterine papillary serous carcinoma (UPSC). In some embodiments, the cancer is hepatocholangiocarcinoma. In some embodiments, the cancer is soft tissue and bone synovial sarcoma. In some embodiments, the cancer is rhabdomyosarcoma. In some embodiments, the cancer is osteosarcoma. In some embodiments, the cancer is anaplastic thyroid cancer. In some embodiments, the cancer is adrenocortical carcinoma. In some embodiments, the cancer is pancreatic cancer, or pancreatic ductal carcinoma. In some embodiments, the cancer is pancreatic adenocarcinoma. In some embodiments, the cancer is glioma. In some embodiments, the cancer is malignant peripheral nerve sheath tumors (MPNST). In some embodiments, the cancer is neurofibromatosis-1 associated MPNST. In some embodiments, the cancer is Waldenstrom's macroglobulinemia. In some embodiments, the cancer is medulloblastoma.

In some embodiments, the present invention provides a method for treating a cancer selected from leukemia or a cancer of the blood, comprising administering to a patient in need thereof an effective amount of a disclosed X4P-001 composition, optionally in combination with an additional therapeutic agent such as those described herein. In some embodiments, the cancer is selected from acute myeloid leukemia (AML), chronic myeloid leukemia (CML), acute lymphocytic leukemia (ALL), chronic lymphocytic leukemia (CLL), or a virally induced leukemia.

In some embodiments, the patient has a resectable solid tumor, meaning that the patient's tumor is deemed susceptible to being removed by surgery. In other embodiments, the patient has an unresectable solid tumor, meaning that the patient's tumor has been deemed not susceptible to being removed by surgery, in whole or in part.

In some embodiments, the cancer is an advanced cancer, such as an advanced kidney cancer or advanced renal cell carcinoma.

In some embodiments, the present invention provides a method for treating refractory cancer in a patient in need thereof comprising administering to a patient in need thereof an effective amount of a disclosed X4P-001 composition or pharmaceutical composition thereof, optionally in combination with an additional therapeutic agent such as those described herein.

In certain embodiments, the patient was previously administered a protein kinase inhibitor. In some embodiments, the patient was previously administered a VEGF-R antagonist. In certain embodiments, the patient was previously administered an immune checkpoint inhibitor. In some embodiments, the patient was previously administered an immune checkpoint inhibitor selected from nivolumab (Opdivo®, Bristol-Myers Squibb), pembrolizumab (Keytruda®, Merck), or ipilumumab (Yervoy®, Bristol-Myers Squibb).

In some embodiments, a disclosed X4P-001 composition is administered to a patient in a fasted state.

Cellular Proliferative Disorders

The present invention features methods and compositions for the diagnosis and prognosis of cellular proliferative disorders (e.g., cancer) and the treatment of these disorders by targeting CXCR4. Cellular proliferative disorders described herein include, e.g., cancer, obesity, and proliferation-dependent diseases. Such disorders may be diagnosed using methods known in the art.

Cancer

Cancer includes, in one embodiment, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

In some embodiments, the cancer is glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, or retinoblastoma.

In some embodiments, the cancer is acoustic neuroma, astrocytoma (e.g. Grade I—Pilocytic Astrocytoma, Grade II—Low-grade Astrocytoma, Grade III—Anaplastic Astrocytoma, or Grade IV—Glioblastoma (GBM)), chordoma, CNS lymphoma, craniopharyngioma, brain stem glioma, ependymoma, mixed glioma, optic nerve glioma, subependymoma, medulloblastoma, meningioma, metastatic brain tumor, oligodendroglioma, pituitary tumors, primitive neuroectodermal (PNET) tumor, or schwannoma. In some embodiments, the cancer is a type found more commonly in children than adults, such as brain stem glioma, craniopharyngioma, ependymoma, juvenile pilocytic astrocytoma (WA), medulloblastoma, optic nerve glioma, pineal tumor, primitive neuroectodermal tumors (PNET), or rhabdoid tumor. In some embodiments, the patient is an adult human. In some embodiments, the patient is a child or pediatric patient.

Cancer includes, in another embodiment, without limitation, mesothelioma, hepatobilliary (hepatic and billiary duct), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, non-Hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

The present invention further features methods and compositions for the diagnosis, prognosis and treatment of viral-associated cancers, including human immunodeficiency virus (HIV) associated solid tumors, human papilloma virus (HPV)-16 positive incurable solid tumors, and adult T-cell leukemia, which is caused by human T-cell leukemia virus type I (HTLV-I) and is a highly aggressive form of CD4+ T-cell leukemia characterized by clonal integration of HTLV-I in leukemic cells (See https://clinicaltrials.gov/ct2/show/study/ NCT02631746); as well as virus-associated tumors in gastric cancer, nasopharyngeal carcinoma, cervical cancer, vaginal cancer, vulvar cancer, squamous cell carcinoma of the head and neck, and Merkel cell carcinoma. (See https://clinicaltrials.govict2/show/study/NCT02488759; see also https://clinicaltrials.gov/ct2/show/study/NC TO240886; https://clinicaltrials.gov/ct2/show/NCT02426892)

In some embodiments, the present invention provides a method for treating a tumor in a patient in need thereof, comprising administering to the patient a disclosed X4P-001 composition. In some embodiments, the tumor comprises any of the cancers described herein. In some embodiments, the tumor comprises melanoma cancer. In some embodiments, the tumor comprises breast cancer. In some embodiments, the tumor comprises lung cancer. In some embodiments the the tumor comprises small cell lung cancer (SCLC). In some embodiments the the tumor comprises non-small cell lung cancer (NSCLC).

In some embodiments, the tumor is treated by arresting further growth of the tumor. In some embodiments, the tumor is treated by reducing the size (e.g., volume or mass) of the tumor by at least 5%, 10%, 25%, 50%, 75%, 90% or 99% relative to the size of the tumor prior to treatment. In some embodiments, tumors are treated by reducing the quantity of the tumors in the patient by at least 5%, 10%, 25%, 50%, 75%, 90% or 99% relative to the quantity of tumors prior to treatment.

Primary Immune Deficiencies

In some embodiments, the present invention provides a method for treating one or more disorders, diseases, and/or conditions wherein the disorder, disease, or condition includes, but is not limited to, a primary immunodeficiency disease or disorder, comprising administering to a patient in need thereof an effective amount of a disclosed compound. Primary immune deficiencies treatable by the methods of the present invention include: warts, hypogammaglobulinemia, infections, myelokathexis (WHIM) syndrome; severe congenital neutropenia (SCN), especially those arising from G6PC3 deficiency (McDermott et al. (2010) Blood 116: 2793-2802); GATA2 deficiency (Mono MAC syndrome) (Maciejweski-Duval et al. (2015) J. Leukoc. Biol. 5MA0815-288R (Epub. ahead of printing); idiopathic CD4+ T lymphocytopenia (ICL); and Wiskott-Aldrich Syndrome.

In other embodiments, the invention relates to a method of inhibiting CXCR4 activity in a biological sample comprising the step of contacting said biological sample with a disclosed X4P-001 composition.

According to another embodiment, the invention relates to a method of inhibiting CXCR4, or a mutant thereof, activity in a biological sample comprising the step of contacting said biological sample with a disclosed X4P-001 composition. In certain embodiments, the invention relates to a method of inhibiting CXCR4, or a mutant thereof, activity in a biological sample comprising the step of contacting said biological sample with a disclosed X4P-001 composition.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Co-Administration With Additional Therapeutic Agents

In one aspect, the present invention provides a method of treating a cancer, such as those described herein, by administering to a patient in need thereof a disclosed X4P-001 composition. In some embodiments, the method includes co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of a disclosed X4P-001 composition and the additional therapeutic agent or agents acts synergistically to prevent or reduce immune escape and/or angiogenic escape of the cancer. In some embodiments, the patient has previously been administered another anticancer agent, such as an adjuvant therapy or immunotherapy. In some embodiments, the cancer is refractory.

Certain methods of treating a disease or disorder by co-administering X4P-001 with one or more additional agents are described in PCT Application No. PCT/US2018/038776, filed Jun. 21, 2018, the entirety of which is hereby incorporated by reference.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

In some embodiments, the additional therapeutic agent is a kinase inhibitor or VEGF-R antagonist. Approved VEGF inhibitors and kinase inhibitors useful in the present invention include: bevacizumab (Avastin®, Genentech/Roche) an anti-VEGF monoclonal antibody; ramucirumab (Cyramza®, Eli Lilly), an anti-VEGFR-2 antibody and ziv-aflibercept, also known as VEGF Trap (Zaltrap®; Regeneron/Sanofi). VEGFR inhibitors, such as regorafenib (Stivarga®, Bayer); vandetanib (Caprelsa®, AstraZeneca); axitinib (Inlyta®, Pfizer); and lenvatinib (Lenvima®, Eisai); Raf inhibitors, such as sorafenib (Nexavar®, Bayer AG and Onyx); dabrafenib (Tafinlar®, Novartis); and vemurafenib (Zelboraf®, Genentech/Roche); MEK inhibitors, such as cobimetanib (Cotellic®, Exelexis/Genentech/Roche); trametinib (Mekinist®, Novartis); Bcr-Abl tyrosine kinase inhibitors, such as imatinib (Gleevec®, Novartis); nilotinib (Tasigna®, Novartis); dasatinib (Sprycel®, BristolMyersSquibb); bosutinib (Bosulif®, Pfizer); and ponatinib (Inclusig®, Ariad Pharmaceuticals); Her2 and EGFR inhibitors, such as gefitinib (Iressa®, AstraZeneca); erlotinib (Tarceeva®, Genentech/Roche/Astellas); lapatinib (Tykerb®, Novartis); afatinib (Gilotrif®, Boehringer Ingelheim); osimertinib (targeting activated EGFR, Tagrisso®, AstraZeneca); and brigatinib (Alunbrig®, Ariad Pharmaceuticals); c-Met and VEGFR2 inhibitors, such as cabozanitib (Cometriq®, Exelexis); and multikinase inhibitors, such as sunitinib (Sutent®, Pfizer); pazopanib (Votrient®, Novartis); ALK inhibitors, such as crizotinib (Xalkori®, Pfizer); ceritinib (Zykadia®, Novartis); and alectinib (Alecenza®, Genentech/Roche); Bruton's tyrosine kinase inhibitors, such as ibrutinib (Imbruvica®, Pharmacyclics/Janssen); and Flt3 receptor inhibitors, such as midostaurin (Rydapt®, Novartis).

Other kinase inhibitors and VEGF-R antagonists that are in development and may be used in the present invention include tivozanib (Aveo Pharmaeceuticals); vatalanib (Bayer/Novartis); lucitanib (Clovis Oncology); dovitinib (TKI258, Novartis); Chiauanib (Chipscreen Biosciences); CEP-11981 (Cephalon); linifanib (Abbott Laboratories); neratinib (HKI-272, Puma Biotechnology); radotinib (Supect®, IY5511, Il-Yang Pharmaceuticals, S. Korea); ruxolitinib (Jakafi®, Incyte Corporation); PTC299 (PTC Therapeutics); CP-547,632 (Pfizer); foretinib (Exelexis, GlaxoSmithKline); quizartinib (Daiichi Sankyo) and motesanib (Amgen/Takeda).

In some embodiments, the additional therapeutic agent is an mTOR inhibitor, which inhibits cell proliferation, angiogenesis and glucose uptake. Approved mTOR inhibitors useful in the present invention include everolimus (Afinitor®, Novartis); temsirolimus (Torisel®, Pfizer); and sirolimus (Rapamune®, Pfizer).

In some embodiments, the additional therapeutic agent is a Poly ADP ribose polymerase (PARP) inhibitor. Approved PARP inhibitors useful in the present invention include olaparib (Lynparza®, AstraZeneca); rucaparib (Rubraca®, Clovis Oncology); and niraparib (Zejula®, Tesaro). Other PARP inhibitors being studied which may be used in the present invention include talazoparib (MDV3800/BMN 673/LT00673, Medivation/Pfizer/Biomarin); veliparib (ABT-888, AbbVie); and BGB-290 (BeiGene, Inc.).

In some embodiments, the additional therapeutic agent is a phosphatidylinositol 3 kinase (PI3K) inhibitor. Approved PI3K inhibitors useful in the present invention include idelalisib (Zydelig®, Gilead). Other PI3K inhibitors being studied which may be used in the present invention include alpelisib (BYL719, Novartis); taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

In some embodiments, the additional therapeutic agent is a proteasome inhibitor. Approved proteasome inhibitors useful in the present invention include bortezomib (Velcade®, Takeda); carfilzomib (Kyprolis®, Amgen); and ixazomib (Ninlaro®, Takeda).

In some embodiments, the additional therapeutic agent is a histone deacetylase (HDAC) inhibitor. Approved HDAC inhibitors useful in the present invention include vorinostat (Zolinza®, Merck); romidepsin (Istodax®, Celgene); panobinostat (Farydak®, Novartis); and belinostat (Beleodaq®, Spectrum Pharmaceuticals). Other HDAC inhibitors being studied which may be used in the present invention include entinostat (SNDX-275, Syndax Pharmaceuticals) (NCT00866333); and chidamide (Epidaza®, HBI-8000, Chipscreen Biosciences, China).

In some embodiments, the additional therapeutic agent is a CDK inhibitor, such as a CDK 4/6 inhibitor. Approved CDK 4/6 inhibitors useful in the present invention include palbociclib (Ibrance®, Pfizer); and ribociclib (Kisqali®, Novartis). Other CDK 4/6 inhibitors being studied which may be used in the present invention include abemaciclib (Ly2835219, Eli Lilly); and trilaciclib (G1T28, G1 Therapeutics).

In some embodiments, the additional therapeutic agent is an indoleamine (2,3)-dioxygenase (IDO) inhibitor. IDO inhibitors being studied which may be used in the present invention include epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); and an enzyme that breaks down kynurenine (Kynase, Kyn Therapeutics).

In some embodiments, the additional therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (Lartruvo®; Eli Lilly). Approved EGFR antagonists which may be used in the present invention include cetuximab (Erbitux®, Eli Lilly); necitumumab (Portrazza®, Eli Lilly), panitumumab (Vectibix®, Amgen); and osimertinib (targeting activated EGFR, Tagrisso®, AstraZeneca).

In some embodiments, the additional therapeutic agent is an aromatase inhibitor. Approved aromatase inhibitors which may be used in the present invention include exemestane (Aromasin®, Pfizer); anastazole (Arimidex®, AstraZeneca) and letrozole (Femora®, Novartis).

In some embodiments, the additional therapeutic agent is an antagonist of the hedgehog pathway. Approved hedgehog pathway inhibitors which may be used in the present invention include sonidegib (Odomzo®, Sun Pharmaceuticals); and vismodegib (Erivedge®, Genentech), both for treatment of basal cell carcinoma.

In some embodiments, the additional therapeutic agent is a folic acid inhibitor. Approved folic acid inhibitors useful in the present invention include pemetrexed (Alimta®, Eli Lilly).

In some embodiments, the additional therapeutic agent is a CC chemokine receptor 4 (CCR4) inhibitor. CCR4 inhibitors being studied that may be useful in the present invention include mogamulizumab (Poteligeo®, Kyowa Hakko Kirin, Japan).

In some embodiments, the additional therapeutic agent is an isocitrate dehydrogenase (IDH) inhibitor. IDH inhibitors being studied which may be used in the present invention include AG120 (Celgene; NCT02677922); AG221 (Celgene, NCT02677922; NCT02577406); BAY1436032 (Bayer, NCT02746081); IDH305 (Novartis, NCT02987010).

In some embodiments, the additional therapeutic agent is an arginase inhibitor. Arginase inhibitors being studied which may be used in the present invention include AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, the additional therapeutic agent is a glutaminase inhibitor. Glutaminase inhibitors being studied which may be used in the present invention include CB-839 (Calithera Biosciences).

In some embodiments, the additional therapeutic agent is an antibody that binds to tumor antigens, that is, proteins expressed on the cell surface of tumor cells. Approved antibodies that bind to tumor antigens which may be used in the present invention include rituximab (Rituxan®, Genentech/BiogenIdec); ofatumumab (anti-CD20, Arzerra®, GlaxoSmithKline); obinutuzumab (anti-CD20, Gazyva®, Genentech), ibritumomab (anti-CD20 and Yttrium-90, Zevalin®, Spectrum Pharmaceuticals); daratumumab (anti-CD38, Darzalex®, Janssen Biotech), dinutuximab (anti-glycolipid GD2, Unituxin®, United Therapeutics); trastuzumab (anti-HER2, Herceptin®, Genentech); ado-trastuzumab emtansine (anti-HER2, fused to emtansine, Kadcyla®, Genentech); and pertuzumab (anti-HER2, Perjeta®, Genentech); and brentuximab vedotin (anti-CD30-drug conjugate, Adcetris®, Seattle Genetics).

In some embodiments, the additional therapeutic agent is a topoisomerase inhibitor. Approved topoisomerase inhibitors useful in the present invention include irinotecan (Onivyde®, Merrimack Pharmaceuticals); topotecan (Hycamtin®, GlaxoSmithKline). Topoisomerase inhibitors being studied which may be used in the present invention include pixantrone (Pixuvri®, CTI Biopharma).

In some embodiments, the additional therapeutic agent is a nucleoside inhibitor, or other therapeutic that interfere with normal DNA synthesis, protein synthesis, cell replication, or will otherwise inhibit rapidly proliferating cells. Such nucleoside inhibitors or other therapeutics include trabectedin (guanidine alkylating agent, Yondelis®, Janssen Oncology), mechlorethamine (alkylating agent, Valchlor®, Aktelion Pharmaceuticals); vincristine (Oncovin®, Eli Lilly; Vincasar®, Teva Pharmaceuticals; Marqibo®, Talon Therapeutics); temozolomide (prodrug to alkylating agent 5-(3-methyltriazen-1-yl)-imidazole-4-carboxamide (MTIC) Temodar®, Merck); cytarabine injection (ara-C, antimetabolic cytidine analog, Pfizer); lomustine (alkylating agent, CeeNU®, Bristol-Myers Squibb; Gleostine®, NextSource Biotechnology); azacitidine (pyrimidine nucleoside analog of cytidine, Vidaza®, Celgene); omacetaxine mepesuccinate (cephalotaxine ester) (protein synthesis inhibitor, Synribo®; Teva Pharmaceuticals); asparaginase *Envinia chrysanthemi* (enzyme for depletion of asparagine, Elspar®, Lundbeck; Erwinaze®, EUSA Pharma); eribulin mesylate (microtubule inhibitor, tubulin-based antimitotic, Halaven®, Eisai); cabazitaxel (microtubule inhibitor, tubulin-based antimitotic, Jevtana®, Sanofi-Aventis); capacetrine (thymidylate synthase inhibitor, Xeloda®, Genentech); bendamustine (bifunctional mechlorethamine derivative, believed to form interstrand DNA cross-links, Treanda®, Cephalon/Teva); ixabepilone (semi-synthetic analog of epothilone B, microtubule inhibitor, tubulin-based antimitotic, Ixempra®, Bristol-Myers Squibb); nelarabine (prodrug of deoxyguanosine analog, nucleoside metabolic inhibitor, Arranon®, Novartis); clorafabine (prodrug of ribonucleotide reductase inhibitor, competitive inhibitor of deoxycytidine, Clolar®, Sanofi-Aventis); and trifluridine and tipiracil (thymidine-based nucleoside analog and thymidine phosphorylase inhibitor, Lonsurf®, Taiho Oncology).

In some embodiments, the additional therapeutic agent is a platinum-based therapeutic, also referred to as platins. Platins cause cross-linking of DNA, such that they inhibit DNA repair and/or DNA synthesis, mostly in rapidly reproducing cells, such as cancer cells. Approved platinum-based therapeutics which may be used in the present invention include cisplatin (Platinol®, Bristol-Myers Squibb); carboplatin (Paraplatin®, Bristol-Myers Squibb; also, Teva; Pfizer); oxaliplatin (Eloxitin® Sanofi-Aventis); and nedaplatin (Aqupla®, Shionogi). Other platinum-based therapeutics which have undergone clinical testing and may be used in the present invention include picoplatin (Poniard Pharmaceuticals); and satraplatin (JM-216, Agennix).

In some embodiments, the additional therapeutic agent is a taxane compound, which causes disruption of microtubules, which are essential for cell division. Approved taxane compounds which may be used in the present invention include paclitaxel (Taxol®, Bristol-Myers Squibb), docetaxel (Taxotere®, Sanofi-Aventis; Docefrez®, Sun Pharmaceutical), albumin-bound paclitaxel (Abraxane®; Abraxis/Celgene), and cabazitaxel (Jevtana®, Sanofi-Aventis). Other taxane compounds which have undergone clinical testing and may be used in the present invention include SID530 (SK Chemicals, Co.) (NCT00931008).

In some embodiments, the additional therapeutic agent is an inhibitor of anti-apoptotic proteins, such as BCL-2. Approved anti-apoptotics which may be used in the present invention include venetoclax (Venclexta®, AbbVie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signalling processes should proceed.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory $CD8^+$ (αβ) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), nivolumab (Opdivo®, BMS-936558; anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, or a CTLA-4 antagonist. In some embodiments, a CXCR4 antagonist such as X4P-001 or a pharmaceutically acceptable salt thereof is administered in combination with nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); or atezolizumab (anti-PD-L1 antibody, Tecentriq®, Genentech).

Other immune checkpoint inhibitors suitable for use in the present invention include REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; and PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

Nivolumab (Opdivo®, BMS-93568/1VDX1106; Bristol-Myers Squibb), is a fully human IgG4 monoclonal antibody that acts as an immunomodulator by binding to the programmed cell death 1 (PD-1) receptor and selectively blocking interaction with its ligands PD-L1 and PD-L2. The structure and other properties of nivolumab are specified at http://www.drugbank.ca/drugs/DB09035, accessed on Mar. 14, 2016, the disclosure of which is hereby incorporated herein. Nivolumab is approved for use in treatment of patients with advanced renal cell carcinoma who have received prior anti-angiogenic therapy; as a single agent in certain types of unresectable or metastatic melanoma; in treating unresectable or metastatic melanoma or in combination with ipilimumab in treating unresectable or metastatic melanoma; and for treatment of metastatic non-small cell lung cancer and progression on or after platinum-based chemotherapy. Additionally, nivolumab has been tested or mentioned as a possible treatment in other oncologic indications, including solid tumors; skin melanoma; glioblastoma; glioma; gliosarcoma; astrocytoma; brain cancer; leukemia; acute myeloid leukemia; chronic myeloid leukemia; chronic lymphocytic leukemia; advanced liver cancer or hepatocellular carcinoma; uveal melanoma; prostate cancer; pancreatic neoplasm and pancreatic cancer; bladder cancer; colorectal cancer; myelodysplastic syndrome; Hodgkin Lymphoma; Non-Hodgkin Lymphoma; multiple myeloma; cervical cancer; endometrial cancer; uterine cancer; ovarian cancer and ovarian carcinoma; peritoneal carcinoma; head and neck squamous cell cancer; gastric cancer; esophageal cancer; Kaposi sarcoma; breast neoplasm, breast adenocarcinoma and breast cancer; bone sarcoma; soft tissue sarcoma; meningiomas; and mesothelioma.

In a phase 3 trial of over 800 patients with advanced clear-cell renal cell carcinoma, for which they had received previous treatment with one or two regimens of antiangiogenic therapy, were randomly assigned to receive 3 mg/kg body weight of nivolumab, intravenously every two weeks, or a 10 mg everolimus tablet orally daily. Patients treated with nivolumab exhibited longer median overall survival, decreased hazard ratio for death, and higher objective response rate than those patients treated with nivolumab (25%) compared to everolimus (5%) ($P<0.001$), with lower incidence of Grade 3 or 4 treatment-related adverse events (Motzer et al. (2015), New England Journal of Medicine, 373:1803-1813). Accordingly, in some embodiments, the present invention provides a method of treating advanced clear-cell renal cell carcinoma, comprising administering to a patient in need thereof an effective amount of a CXCR4 antagonist such as X4P-001 or a pharmaceutically acceptable salt thereof or pharmaceutical composition thereof in combination with nivolumab or everolimus, optionally wherein that patient has received previous treatment with a regimen of antiangiogenic therapy.

Generally, the amount of nivolumab or other immune checkpoint inhibitor useful in the present invention will be dependent upon the size, weight, age and condition of the patient being treated, the severity of the disorder or condition, and the discretion of the prescribing physician. For example, in its current prescribed labeling for unresectable or metastatic renal cell carcinoma, the recommended course of administration for nivolumab is 3 mg/kg as an intravenous infusion over 60 minutes every two weeks, until disease progression or unacceptable toxicity. In the discretion of the clinician, depending upon individual tolerance, the prescribed dose of nivolumab may be increased, for example, increased in dosage and/or frequency. In the discretion of the clinician, together with the warnings provided with prescribing information, administration of nivolumab may be discontinued, or the dose reduced in the case of significant adverse effects. In some embodiments, nivolumab is administered in the methods of the present invention according to the labeling guidelines above.

In some embodiments, the present invention provides a method for treating a patient by administering a CXCR4 antagonist such as X4P-001 or a pharmaceutically acceptable salt thereof in combination with an immunostimulatory therapeutics. Approved immunostimulatory therapeutics which may be used in the present invention include elotuzumab (anti-SLAMF7-antibody, Empliciti®, Bristol-Myers Squibb). Immunostimulatory compounds being studied that may be used in the present invention include mifamurtide (Mepact®, Takeda Oncology).

Another immunostimulatory therapeutic that may be used in the present invention is recombinant human interleukin 15 (rhIL-15). rhIL-15 has been tested in the clinic as a therapy for melanoma and renal cell carcinoma (NCT01021059 and NCT01369888) and leukemias (NCT02689453). Another immunostimulatory therapeutic that may be used in the present invention is recombinant human interleukin 12 (rhIL-12). Another suitable IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). Recombinant human interleukin 12 (rhIL-12) has been tested in the clinic for many oncological indications, for example, as a therapy for lymphoma (NM-IL-12, Neumedicines, Inc.), (NCT02544724 and NCT02542124).

Another paradigm for immune-stimulation is the use of oncolytic viruses. In some embodiments, the present invention provides a method for treating a patient by administering a disclosed X4P-001 composition in combination with an immunostimulatory therapy such as oncolytic viruses. Approved immunostimulatory oncolytic viruses which may be used in the present invention include talimogene laherparepvec (live, attenuated herpes simplex virus, Imlygic®, Amgen).

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™ A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™ Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a P 13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3K$\alpha$, PI3K$\gamma$, PI3K$\delta$, PI3K$\beta$, PI3K-C2$\alpha$, PI3K-C2$\beta$, PI3K-C2$\gamma$, Vps34, p110-$\alpha$, p110-$\beta$, p110-$\gamma$, p110-$\delta$, p85-$\alpha$, p85-$\beta$, p55-$\gamma$, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, al endronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™ Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms," such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan) PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; Zd$_6$474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from a disclosed X4P-001 composition, as part of a multiple dosage regimen. Alternatively, those agents may be part of a single dosage form, mixed together with a disclosed X4P-001 composition in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both a disclosed X4P-001 composition and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed X4P-001 compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Methods of preparation applicable to certain compounds of the invention are disclosed in Crawford et al. (2008) Org. Process Res. Dev. 12:823-830; U.S. Pat. No. 7,354,934, WO 00/56729, U.S. Ser. No. 60/232,891, and U.S. Ser. No. 60/234,510, as well as An, H.; Wang, T.; Mohan, V.; Griffey, R. H.; Cook, P. D. *Tetrahedron* 1998, 54, 3999-4012; the entire contents of each of which is hereby incorporated by reference. One of ordinary skill in the art is capable of varying such disclosed methods, using no more than routine experimentation, to provide alternate means of preparation, testing, and analysis of compounds of the invention.

Example 1: Methyl Imine Impurity

By high performance liquid chromatography-mass spectrometry (HPLC-MS) analysis, a peak at relative retention time (RRT) 1.13 showed a [M+1]+ of 362 m/z (12 mass units higher than X4P-001). The peak disappears after a few hours if X4P-001 is solubilized in acidic aqueous media. The molecular weight of the impurity along with its chemical behavior suggest a methyl imine structure on the primary amine. The imine impurity, I-1, and likely route of formation are shown in Scheme 1, below.

Scheme 1

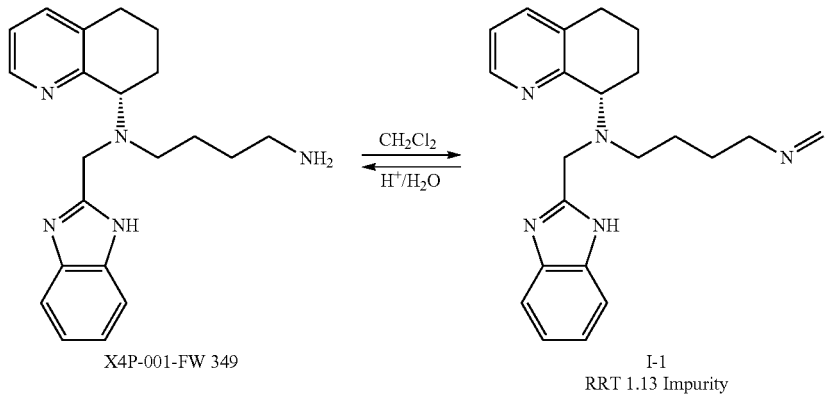

X4P-001-FW 349

I-1
RRT 1.13 Impurity

Example 2: N-Formyl Impurity

By HPLC-MS analysis a RRT 1.28 peak showed an [M+1]+ of 378 m/z (28 mass units higher than X4P-001), which suggested an N-formyl derivative of X4P-001. This has been confirmed by an independent synthesis. Direct reaction of X4P-001 with ethyl formate generated the N-formyl compound I-2, which is identical to the batch impurity based on MS and HPLC data. Formation of the formate is shown in Scheme 2, below.

Scheme 2

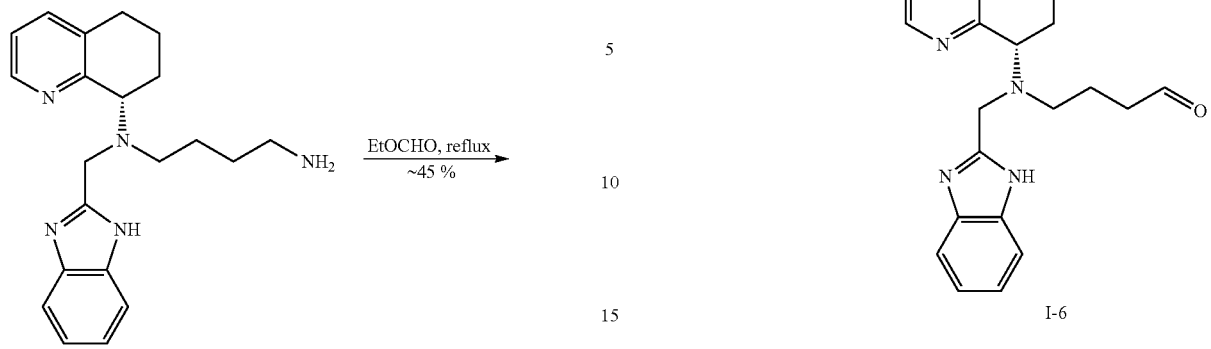

I-2

Example 3: Aldehyde Impurity

A RRT 1.14 peak was characterized as I-6. Without wishing to be bound by any particular theory, it is believed that I-6 results from oxidation of the amine on the alkyl chain of X4P-001, as shown in Scheme 3, below:

Scheme 3

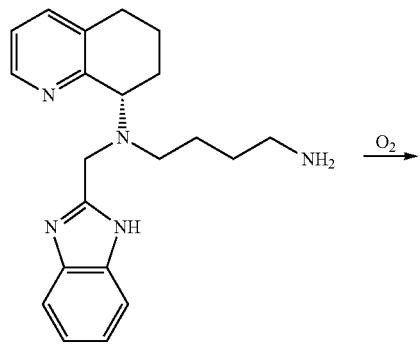

I-6

Example 4: Acetamide Impurity

By HPLC-MS analysis, a RRT 1.39 peak showed an [M+1]+ of 392 m/z (42 mass units higher than X4P-001), which was characterized as the X4P-001 acetamide. It is formed at elevated temperatures by reaction of X4P-001 with the isopropyl acetate crystallization solvent as shown in Scheme 4. An independent synthesis of the acetamide impurity confirmed the structure. Reaction of X4P-001 with acetic anhydride gave the acetamide I-5, which is identical to the batch impurity, based on the MS and HPLC data. Isopropyl acetate is used for certain methods of manufacture of X4P-001 free base that use the p-hydroxy benzoic acid salt of X4P-001.

Scheme 4

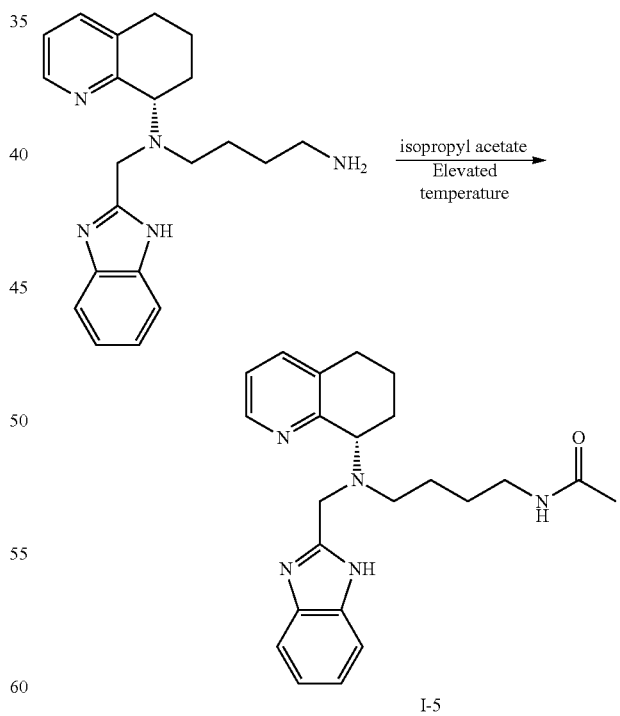

I-5

Example 5: Benzimidazole Impurity

By LC-MS analysis, a RRT 1.67 peak showed an [M+1]+ of 481 m/z (131 mass units higher than X4P-001), which was characterized as the M+benzimidazole compound I-3. It is formed as an impurity during the t-butoxycarbonyl (Boc group) protection of 2-chloromethylbenzimidazole as shown in Scheme 5, below. During the N-alkylation reaction (step 2 of the X4P-001 synthesis), the impurity undergoes alkylation and as a consequence is present throughout the remainder of the manufacturing process.

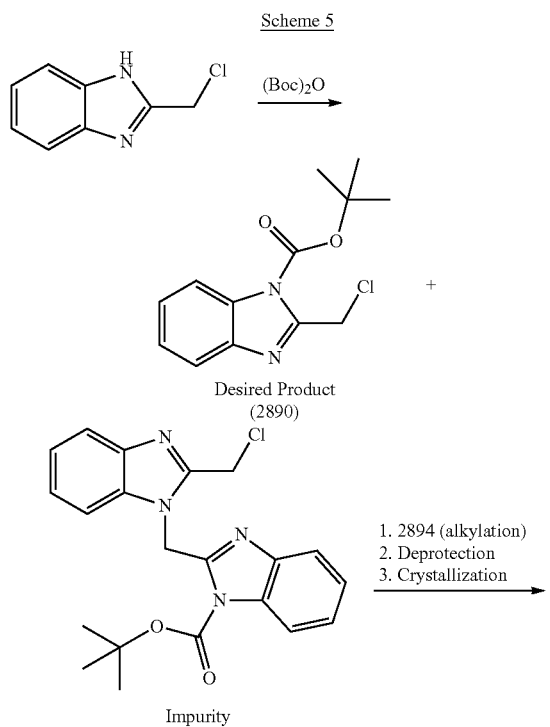

Scheme 5

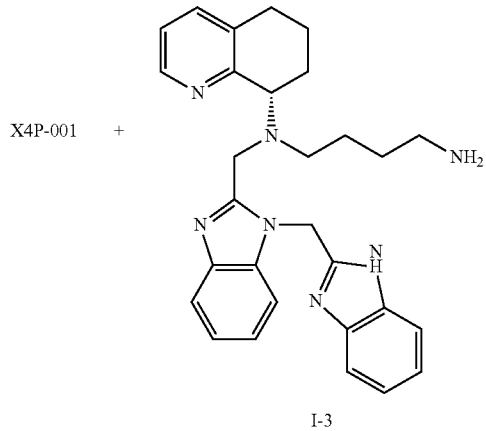

An independent synthesis, involving reaction of a secondary amine 2918 with boc-2-chloromethylbenzimidazole 2890 (I-9), followed by deprotection afforded I-3, which was identical to the observed impurity based on MS and HPLC.

Example 6: Aminal Impurity

An aminal impurity arises in the production of the p-hydroxybenzoic acid salt of X4P-001 by the reaction of the imine impurity with p-hydroxybenzoic acid. This impurity is relevant to the manufacture of X4P-001 in methods that use a p-hydroxybenzoic acid salt of X4P-001 or intermediates thereof.

The structure of the aminal impurity I-4 and its origin are shown below in Scheme 6.

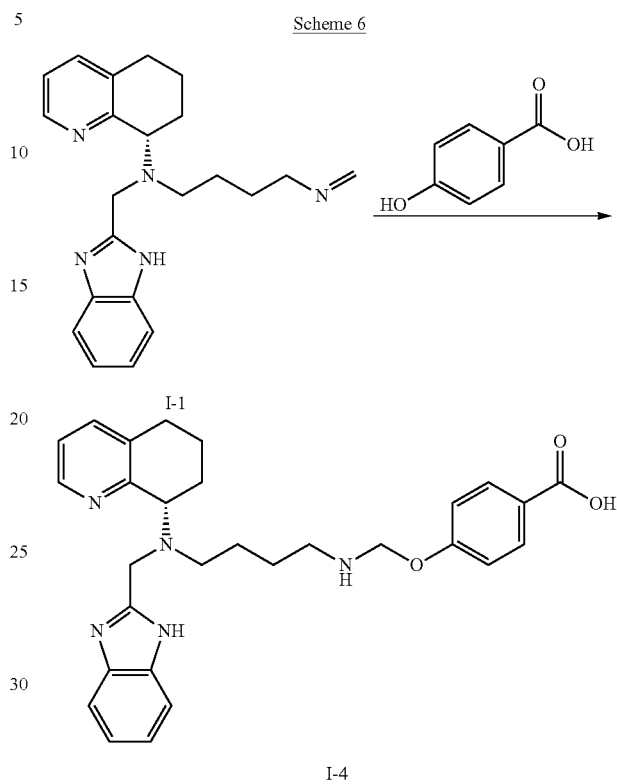

Scheme 6

Example 7: Basis for Setting the Acceptance Criteria for Organic Impurities

The impurity results for relevant batches of X4P-001 and its p-hydroxy benzoic acid (PHB) salt are shown in Table 2, below. The X4P-001 batches used in initial toxicology studies were primarily used in setting the impurity specifications. Batches of X4P-001 p-hydroxy benzoic acid salt were used in longer term toxicology studies and have also been presented in Table 2. Total impurities in these six batches ranged from <0.05% to 1.4% with individual unspecified impurities>0.05% present in only a single batch at the 0.1% level. Taking into account the limited number of batches produced and the impurity profiles of the X4P-001 batches used for toxicology and clinical studies, the drug substance release specification for total impurities has been set at <3.0% w/w with no single unspecified impurity greater than 0.2% w/w (0.5% for stability) (Table 2). Specified individual impurities and p-hydroxy benzoic acid content are all <0.5% w/w except for the imine impurity which has been set at 1.1% based on the level of this impurity administered in toxicology studies. A separate batch of product (not shown in Table 2), namely X4P-001 batch 3-1 (Table 4), provided the drug substance in high purity with total impurities being 1.20% w/w and no specified impurity being greater than 0.07% w/w except for the imine impurity, which was 0.62% w/w. The assay result of the clinical X4P-001 drug substance batch was 99.3% w/w and the chiral purity was >99% ee.

TABLE 2

| | \multicolumn{7}{c}{Batch Number} | | | | | | |
|---|---|---|---|---|---|---|---|
| | 2-1 | 2-2 | 2-3 | 2-4 | 2-5 | 2-6 | 2-7 |
| Drug Substance Type | Free Base | Free Base | Free Base | Free Base | Free Base | PHB salt | PHB salt |
| Individual Impurities by HPLC (% w/w) on anhydrous basis | | | | Results of Testing | | | |
| Imine (I-1) | 1.1 | 0.5 | 0.1 | 0.49 | 0.65 | 0.02 | 0.02 |
| Formyl (I-2) | 0.2 | 0.1 | 0.1 | 0.13 | 0.13 | ND | ND |
| Acetamide (I-5) | 0.1 | 0.1 | 0.1 | 0.10 | 0.06 | NA | NA |
| Aminal (I-4) | NA | NA | NA | NA | NA | 0.01 | ND |
| Benzimidazole (I-3) | 0.01[a] | NR | 0.2 | <LOQ | 0.11 | 0.01 | 0.01 |
| Single Unspecified | NR | NR | 0.1 | ND | NR | ND | ND |
| PHB Content | NA | NA | NA | NA | NA | 28.1 | 28.4 |
| Total Impurities (% w/w)[b] | 1.4 | 0.7 | 0.5 | 0.72 | 1.01 | <0.05 | <0.05 |
| (R)-enantiomer % ee by HPLC | >99 | >99 | >99 | >99 | >99 | >99 | >99 |

Abbreviations used:
[a]Value below LOQ (limit of quantitation)
[b]Specification only relevant for free base clinical drug substance manufactured using X4P-001 p-hydroxybenzoic acid salt as the starting material
NA = Not Applicable
ND = None Detected
NLT = Not Less Than
NMT = Not More Than
NR = None Reported Typically, the wt % of each impurity is determined by HPLC, and is measured either initially or after storage, and optionally on an on-going basis during the shelf life of the X4P-001 composition. In some embodiments, the level of an impurity is measured after storage of the composition under stressed conditions, which are conditions of elevated temperature, humidity, or both, used to approximate the effect of long-term storage under ambient conditions. Accordingly, in some embodiments, the present invention provides an X4P-001 composition comprising no more than 1.1% imine (I-1); no more than 0.3% formyl (I-2); no more than 0.4% benzamidazole (I-3); no more than 0.5% aminal (I-4); no more than 0.5% acetamide (I-5); no more than 0.4% aldehyde (I-6); no more than 0.3% de-BOC NT-316 (I-7); and no more than 0.2% of a single unspecified impurity. Additionally, when free base clinical drug substance is manufactured via X4P-001 p-hydroxybenzoic acid salt, no more than 1.0% PHB is present in the composition. In some embodiments, no more than 3.0% of total impurities are present. In some embodiments, the R-enantiomeric enantiomeric excess (% ee) is no less than 97.0%.

Example 8: Identification of Impurities Resulting After Storage

Upon analysis of stability trial samples of X4P-001 (PTL/ST/0511) by MET/CR/1448 stored at 25° C./60% Relative Humidity (25/60) for three months showed the formation of two unknown impurities.
Unknown 1—RRT 1.14
Unknown 2—RRT 1.24
The impurity at RRT 1.14 was also the principal degradation product under elevated temperature and humidity (80° C./80% RH) conditions in PTL/DA/0175.
Summary
Two impurities formed during a stability study on X4P-001 at t=3 months at 25° C./60% RH and in a forced degradation study under elevated temperature/humidity were identified by LC-MS.

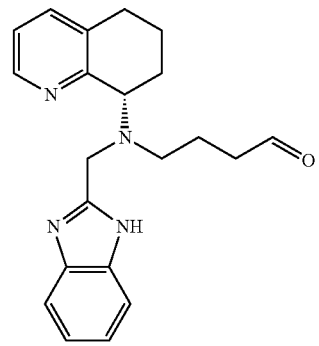

I-6

Impurity at RRT 1.14
MET/CR1448
Aldehyde oxidation product
Empirical formula = $C_{21}H_{24}N_4O$
Monoisotopic mass = 348.195

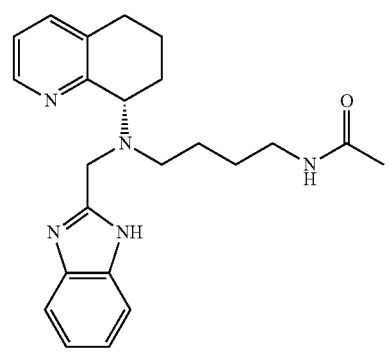

I-5

Impurity at RRT 1.24
MET/CR1448
Acetamide impurity
Empirical formula = $C_{23}H_{29}N_5O$
Monoisotopic mass = 391.237

Experimental
Instrument Parameters

Work was performed on a GMP Waters Alliance HPLC system connected to a ZQ 2000 single quad MS. Data were collected into Empower 2 software.

The assay and impurities method for X4P-001 (MET/CR/1448) is not ideally suited for mass spectrometry because it uses TFA as a modifier in the eluent which can signifcantly suppress ionisation. Initially this was substituted for 0.15% v/v formic acid. The flow rate was also changed to allow connection directly into the inlet of the MS (maximum flow 0.3 mL/min) and the gradient adjusted accordingly.

HPLC Conditions 1

Column: Zorbax Bonus-RP, 150×4.6 mm, 3.5 μm
Inj. volume: 100 L
Detection: UV @ 220 nm (190-400 nm)
  MS ES+100-700 Da, ES− 100-700 Da
Mobile phase A: 0.15% formic acid in Water
Mobile phase B: 0.15% formic acid in MeCN

| Time (mins) | % A | % B |
|---|---|---|
| 0.0 | 95 | 5 |
| 6 | 95 | 5 |
| 51 | 5 | 95 |
| 60 | 5 | 95 |
| 60.1 | 95 | 5 |
| 75 | 95 | 5 |

Flow rate: 0.3 mL/min
Column temperature: Ambient
Run time: 75 minutes

| MS Tune Parameters 1 | | |
|---|---|---|
|  | ES+ | ES− |
| Ion source tab | | |
| Capillary Voltage (kV) | 3.5 | 4 |
| Cone Voltage (V) | 25 | 25 |
| Extractor (V) | 3 | 0 |
| RF lens | 0.4 | 3 |
| Source Temp ° C. | 150 | 150 |
| Desolvation Temp ° C. | 150 | 150 |
| Desolvation gas flow (L/hr) | 300 | 300 |
| Cone gas flow (L/hr) | 50 | 50 |
| Analyzer tab | | |
| LM Res | 15 | 15 |
| HM Res | 15 | 15 |
| Ion Energy | 1.8 | 2 |
| Multiplier | 521 | 521 |

Figure 5:
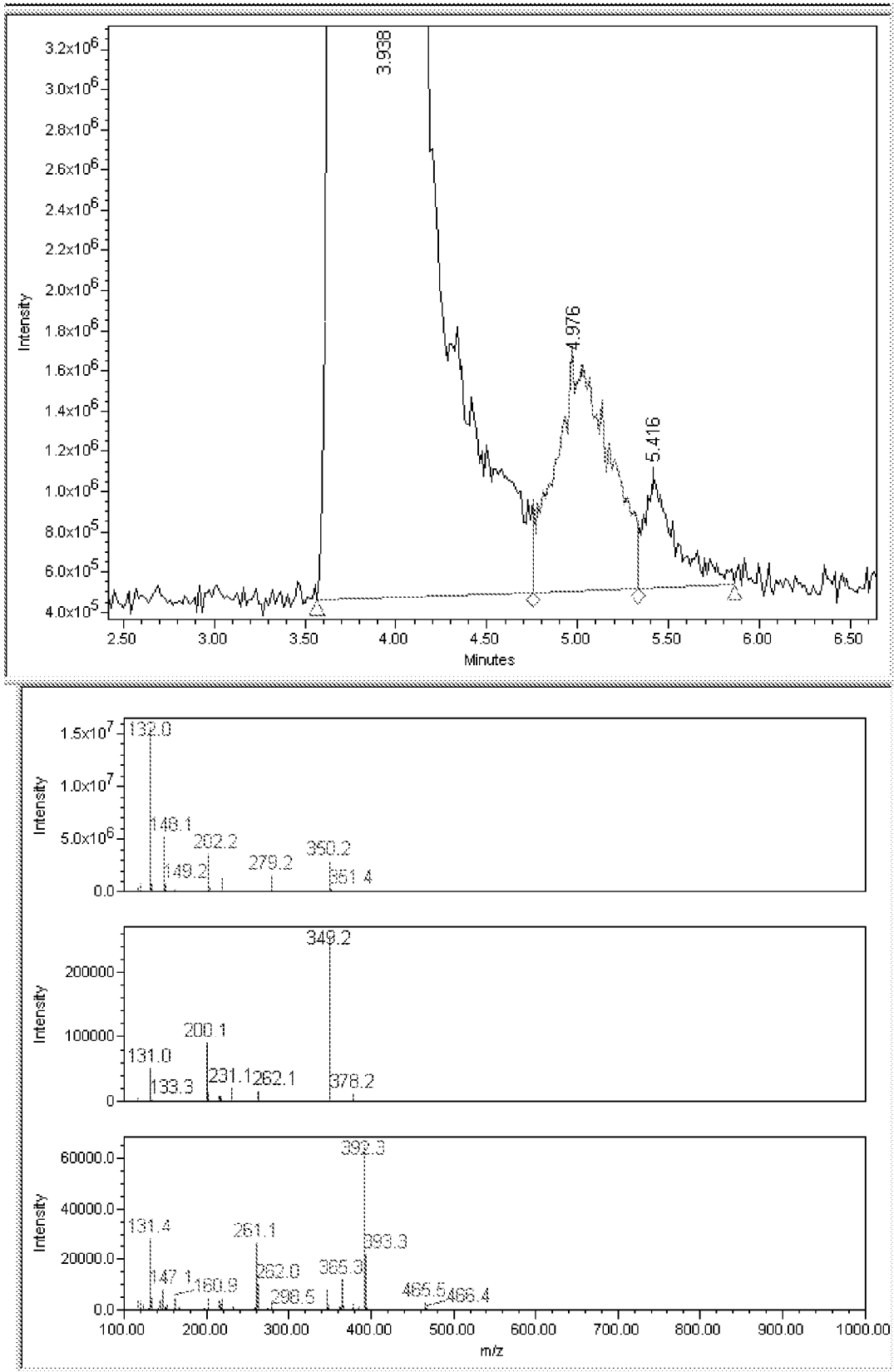
FIG. 5 shows HPLC and MS data for X4P-001, PTL/ST/0511, batch 3-1 (prepared using Process 2), 25° C./60% RH, t=3 months. HPLC conditions 1 (described in detail below); 1 mg/mL in methanol, injection volume 100 μL.
Figure 6:
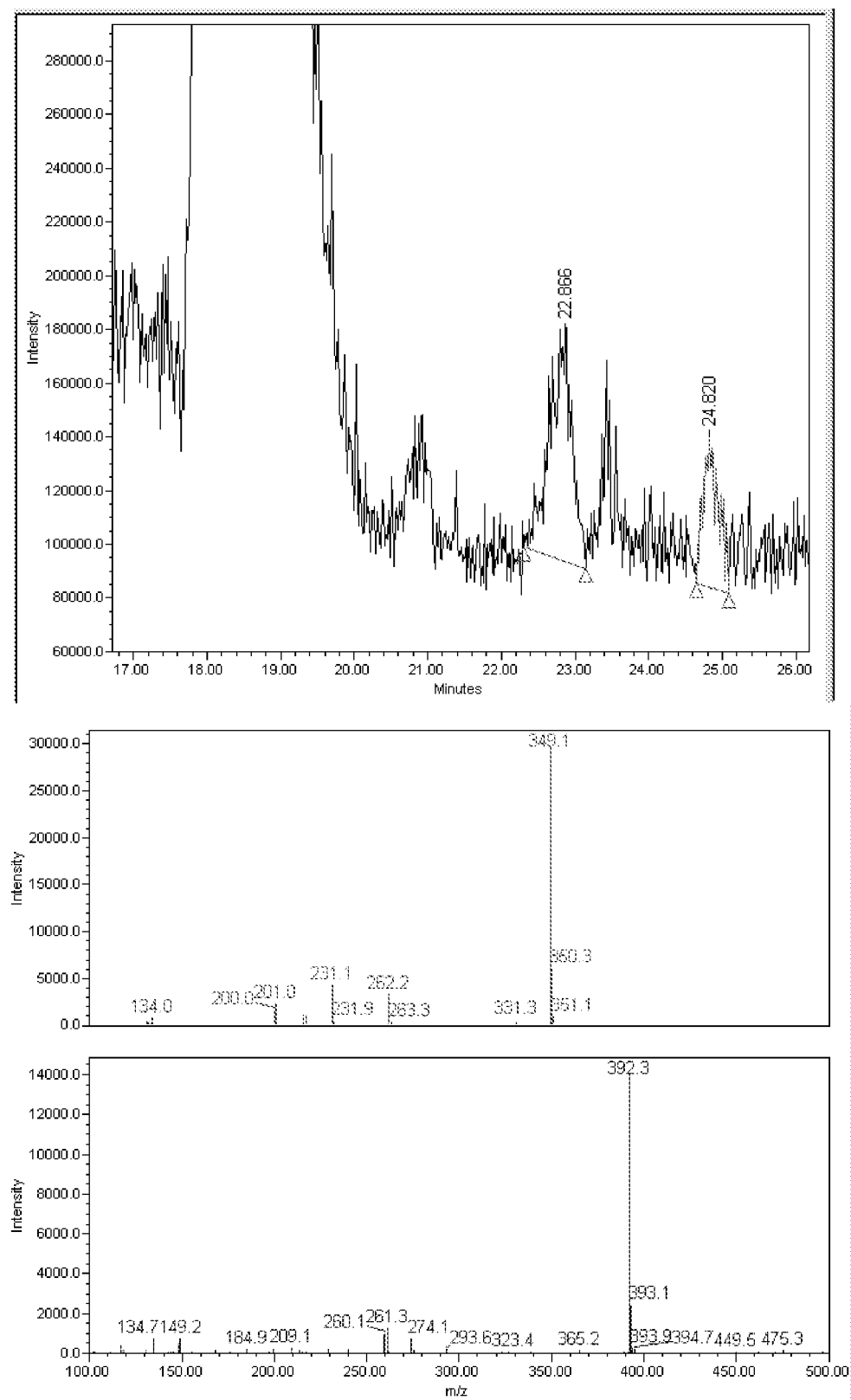
FIG. 6 shows HPLC and MS data for X4P-001, PTL/ST/0511, batch 3-1 (prepared using Process 2), 25° C./60% RH t=3 months. HPLC conditions 2 (described in detail below); 1 mg/mL in methanol, injection volume 100 μL.
Figure 7:
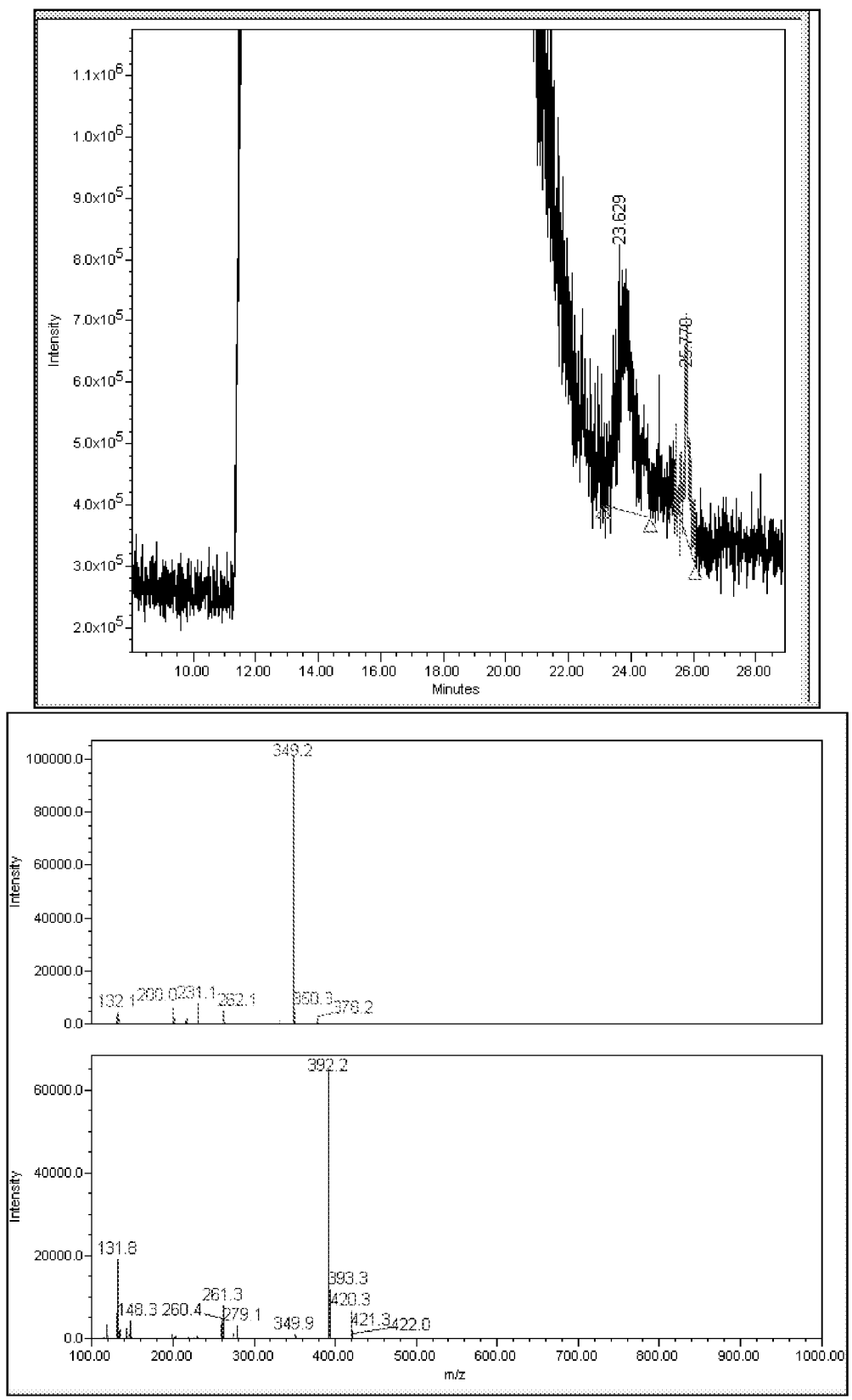
FIG. 7 shows HPLC and MS data for X4P-001, PTL/ST/0511, batch 3-1 (prepared using Process 2), 25° C./60% RH t=3 months. HPLC conditions 2 (described in detail below); sample concentration 10 mg/mL in methanol, 100 μL injection.
Figure 8:
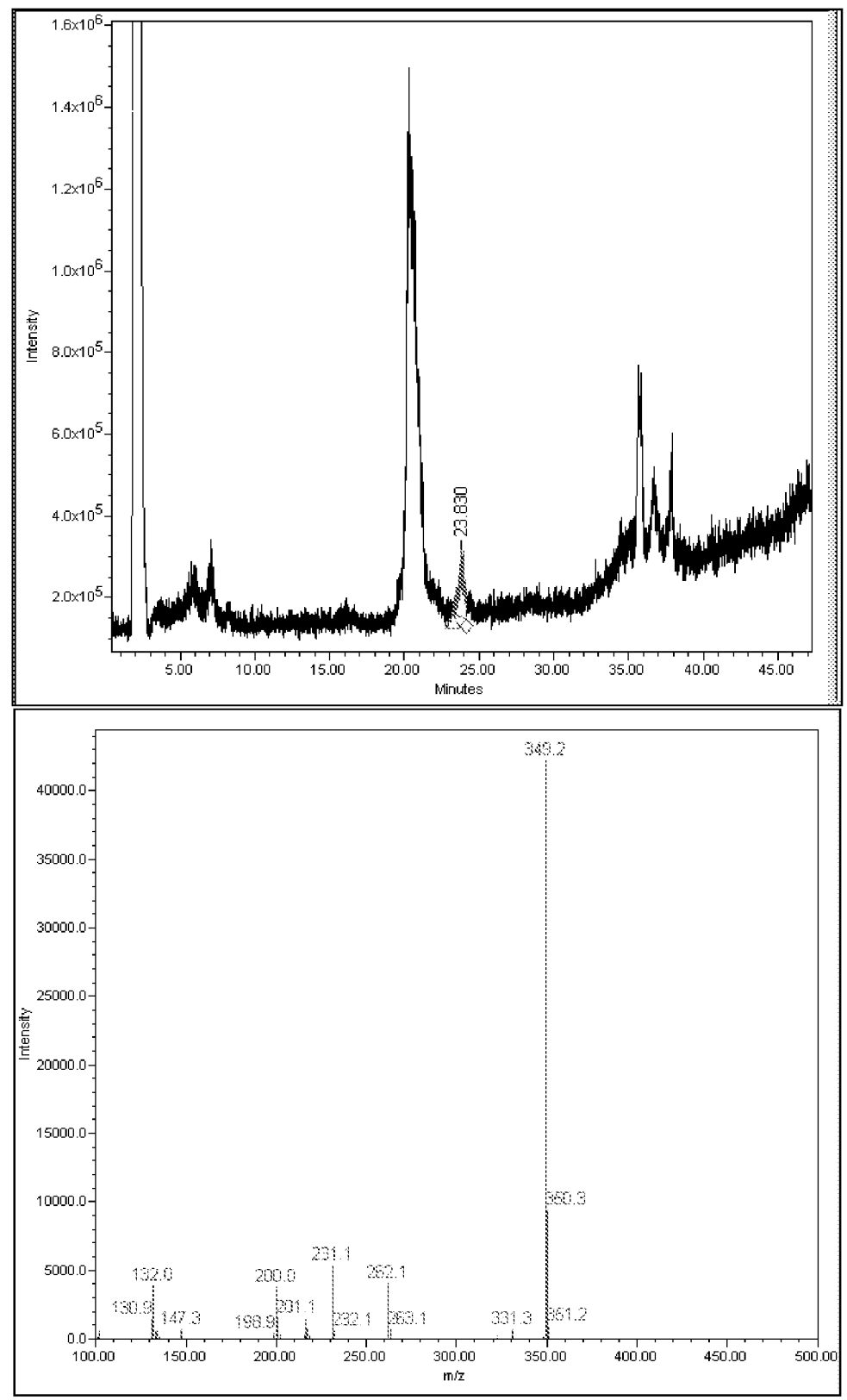
FIG. 8 shows HPLC and MS data for X4P-001, degradation sample 80° C./80% RH t=1 day. HPLC conditions 2 (described in detail below); sample concentration 10 mg/mL in methanol, 100 μL injection volume.
Figure 9:
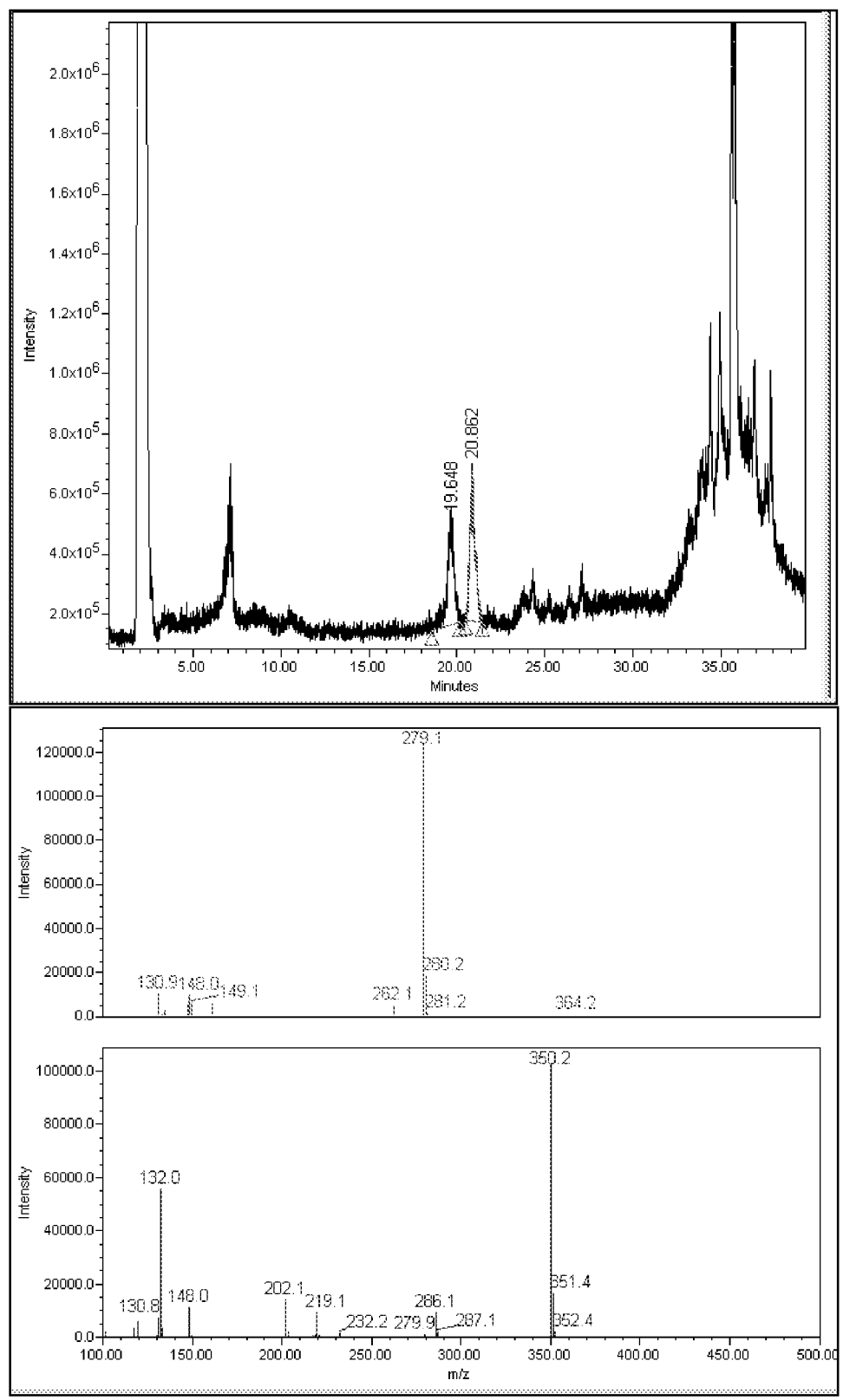
FIG. 9 shows HPLC and MS data for X4P-001, degradation sample 80° C./80% RH t=7 days. HPLC conditions 2 (described in detail below); sample concentration 10 mg/mL in methanol, 100 μL injection volume.

X4P-001 was not retained under these conditions because it required the ion-pairing of TFA. Chromatography and mass spectra obtained are presented in FIG. 5.

Tentative masses were obtained for two impurities. All mass spectra presented have been background corrected (region taken immediately before and after the peak of interest.

Unknown 1 MET/CR/1448 RRT 1.14 [M+H]=m/z 349.2
Unknown 2 MET/CR/1448 RRT 1.24 [M+H]=m/z 392.3

The inventors hypothesized that there was a possibility that the impurities of interest were co-eluting with other impurities. Samples were therefore run using the chromatographic conditions in MET/CR/1448. Concentration and injection volumes were increased to counteract suppression of ionization caused by the TFA.

HPLC Conditions 2

Column: Zorbax SB-C8, 150 mm×4.6 mm, 3.5 μm
Guard column: Zorbax SB-C8, 12.5 mm×4.6 mm, 5 μm
Inj. volume: Various
Detection: UV @ 270 nm
Mobile phase: Mobile phase A: 0.2% TFA in water
  Mobile phase B: 0.1% TFA in acetonitrile

| Gradient elution | | | |
|---|---|---|---|
| Time (mins) | % A | % B | Flow rate (mL/min) |
| 0 | 92 | 8 | 0.8 |
| 5 | 90 | 10 | 0.8 |
| 15 | 89 | 11 | 0.8 |
| 25 | 80 | 20 | 0.8 |
| 28 | 80 | 20 | 0.8 |
| 37 | 55 | 45 | 0.8 |
| 44 | 20 | 80 | 0.8 |
| 47 | 20 | 80 | 0.8 |
| 48 | 92 | 8 | 1.2 |
| 53 | 92 | 8 | 1.2 |
| 54 | 92 | 8 | 0.8 |
| 55 | 92 | 8 | 0.8 |

Initial flow rate: 0.8 mL/min (refer to gradient timetable) split 4:1 into the MS inlet.
Column temperature: 25° C.
Run time: 55 minutes
MS parameters as per Tune Parameters 1 above.

Figure 10:
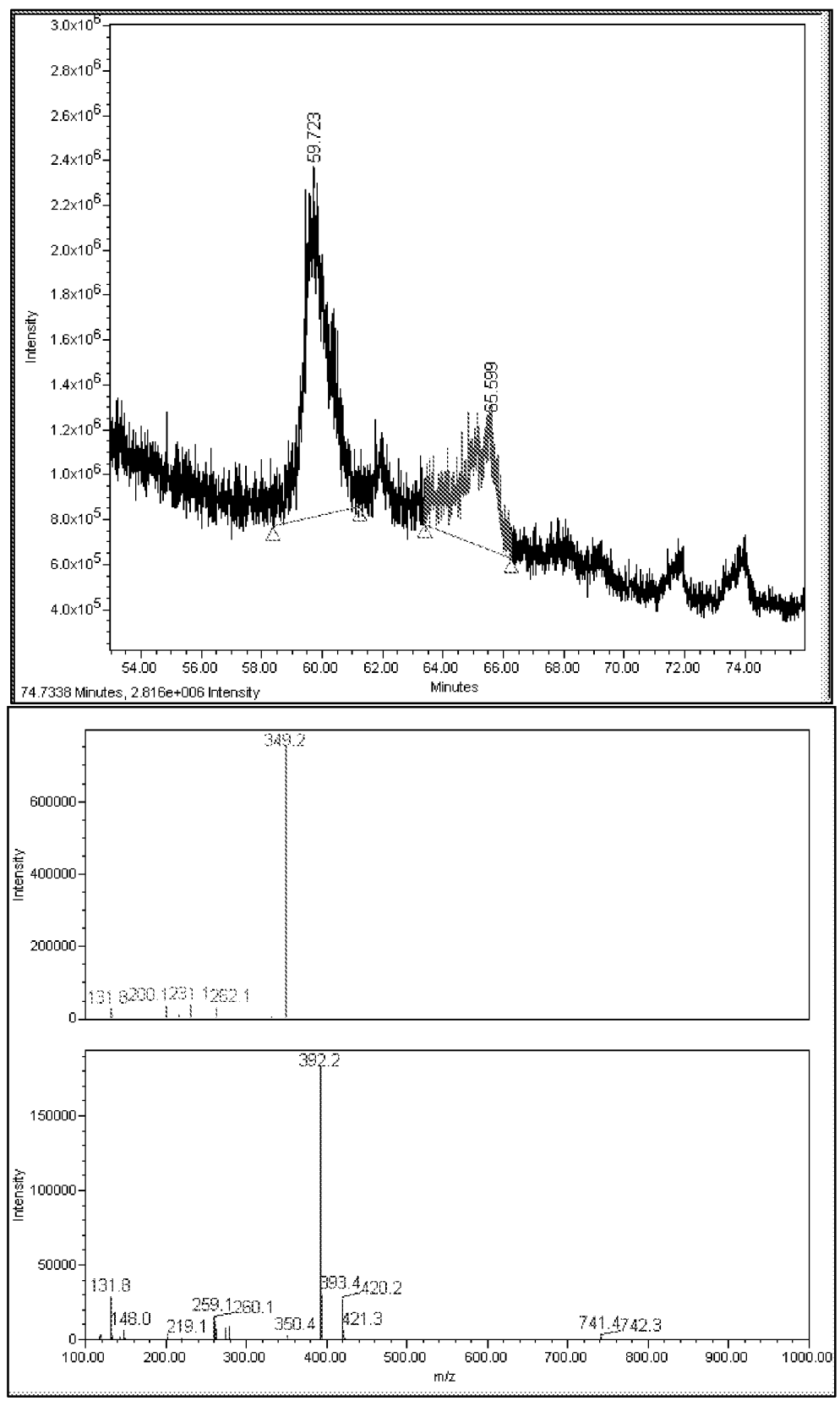
FIG. 10 shows HPLC and MS data for X4P-001, PTL/ST/0511, batch 3-1 (prepared using Process 2), 25° C./60% RH t=3 months. HPLC conditions 3 (described in detail below); sample concentration 10 mg/mL in methanol, 100 μL injection volume.

Various samples of X4P-001 in which the impurities of interest had been detected were prepared in methanol at either 1 or 10 mg/mL:

PTL/ST/0511, batch 3-1, 25/60 t=3 months
PTL/DA/0175 degradation sample 80° C./80% relative humidity (80/80) t=1 and 7 days.
Data obtained are presented in FIGS. 6-9.
Mass spectral data obtained from HPLC conditions 2 were confirmed:
Unknown 1 MET/CR/1448 RRT 1.14 [M+H]=m/z 349.2
Unknown 2 MET/CR/1448 RRT 1.24 [M+H]=m/z 392.3
Finally, the chromtographic conditions were modified to allow the flow to enter the MS without being split. Results from HPLC Conditions 3 are shown in FIG. 10.

HPLC Conditions 3

Column: Zorbax SB-C8, 150 mm×4.6 mm, 3.5 μm
Guard column: Zorbax SB-C8, 12.5 mm×4.6 mm, 5 μm
Inj. volume: Various
Detection: UV @ 270 nm
Mobile phase: Mobile phase A: 0.2% TFA in water
  Mobile phase B: 0.1% TFA in acetonitrile

| Gradient elution | | |
|---|---|---|
| Time (mins) | % A | % B |
| 0 | 92 | 8 |
| 13.3 | 90 | 10 |
| 39.9 | 89 | 11 |
| 66.50 | 80 | 20 |
| 74.48 | 80 | 20 |
| 98.42 | 55 | 45 |
| 117 | 20 | 80 |
| 125 | 20 | 80 |

-continued

Gradient elution

| Time (mins) | % A | % B |
|---|---|---|
| 125.10 | 92 | 8 |
| 140 | 92 | 8 |

Flow rate: 0.3 mL/min directly into the MS inlet
Column temperature: 25° C.
Run time: 140 minutes
MS parameters as per Tune Parameters 1 above.

Discussion of Results

All of the spectra obtained confirmed the initial results even though peak responses and resolution from X4P-001 varied.

Unknown 1 MET/CR/1448 RRT 1.14 [M+H]=m/z 349.2
Unknown 2 MET/CR/1448 RRT 1.24 [M+H]=m/z 392.3

Unknown 1 RRT 1.14 (Aldehyde)

The molecular weight of 348 indicates the loss of a nitrogen (nitrogen rule). This is consistent with the oxidation of the amine on the alkyl chain yielding the aldehyde. The postulated structure is shown below.

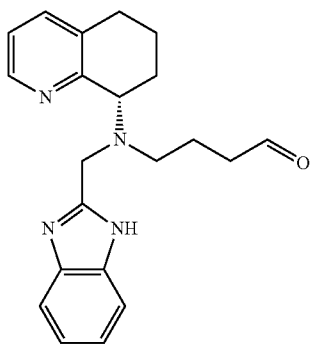

I-6

Empirical formula=C21H24N4O
Monoisotopic mass=348.195

Unknown 2 RRT 1.24 (Acetamide)

The molecular weight of 391 is consistent with I-5, the acetamide impurity (formed with the reaction of X4P-001 with residual isopropyl acetate). The structure of I-5 is shown below.

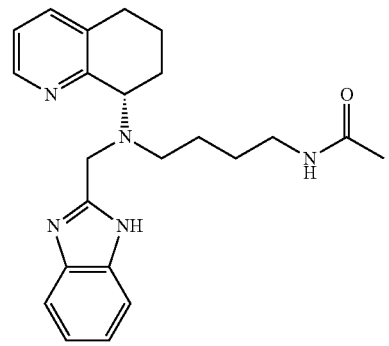

I-5

Empirical formula=$C_{23}H_{29}N_5O$ Monoisotopic mass=391.237

Conclusions

Both unknown impurities were identified from the mass specta data obtained. The impurity at RRT 1.14 is an aldehyde oxidation product and the impurity at RRT 1.24 is the acetamide impurity I-5.

Figure 2:
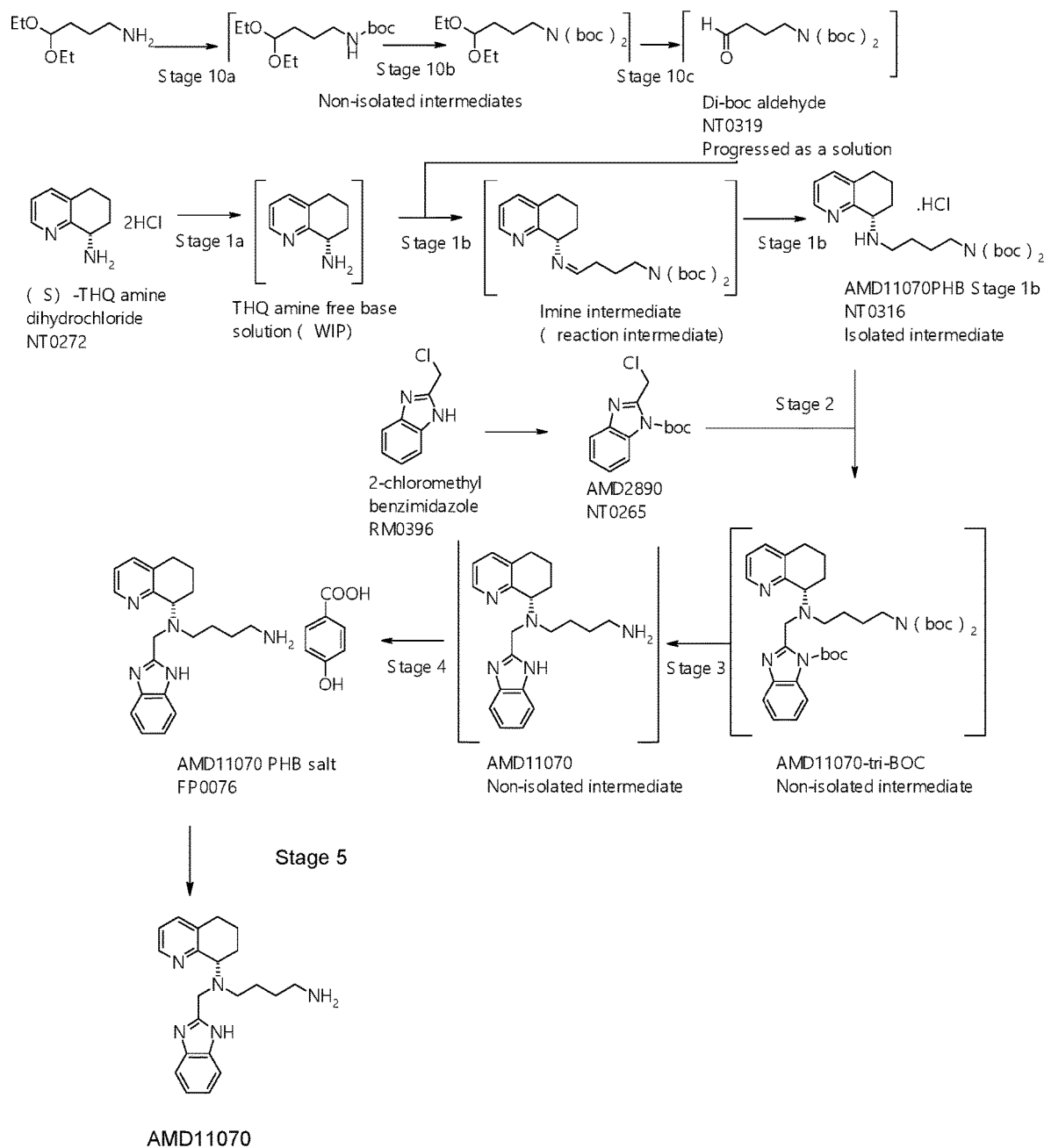
FIG. 2 shows a scheme of the original synthesis process (Process version 2 or Process 2) used to prepare X4P-001 for clinical trials.

Example 9: Improvements to Manufacturing Process for X4P-001 to Reduce and Control Impurity Levels Introduction The final step in the previous preparation of GMP drug substance in support of clinical studies (process version 2; shown in FIG. 2) started with compounds NT-316 and AMD-2890 (I-9). After studying the structure and origin of the most significant impurities which were formed in this preparation, a new process (process version 3) has been developed which offers improved control over the impurity profile as well as the crystallization of the API. Moreover, this effort has significantly enhanced the reproducibility and robustness of the final step in the process.

Description of Synthetic Route and Key Intermediates

API X4P-001 is assembled in 2 steps in a convergent manner starting from two key fragments: NT-316 and AMD-2890. The penultimate intermediate AMID-11070 is not isolated but immediately converted to the API, which is crystallized after a work-up procedure.

Scheme 7 and Scheme 8 show the synthesis for the API molecule X4P-001.

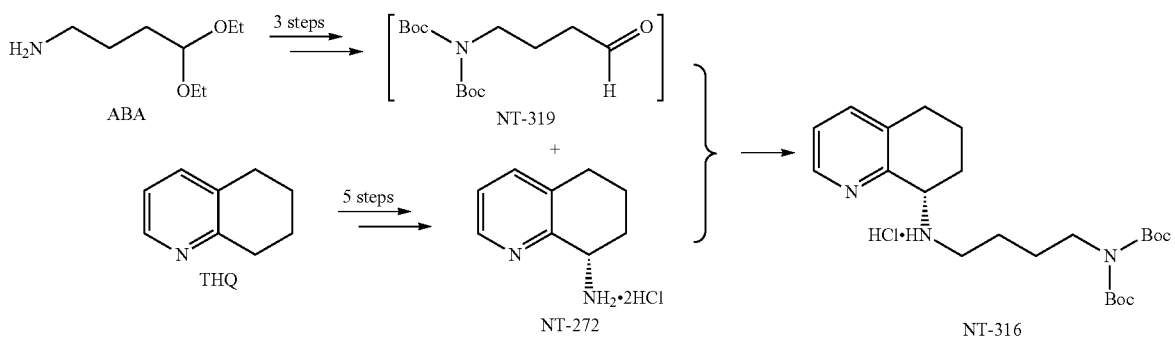

Scheme 7 Early steps in the syntheis of X4P-001.

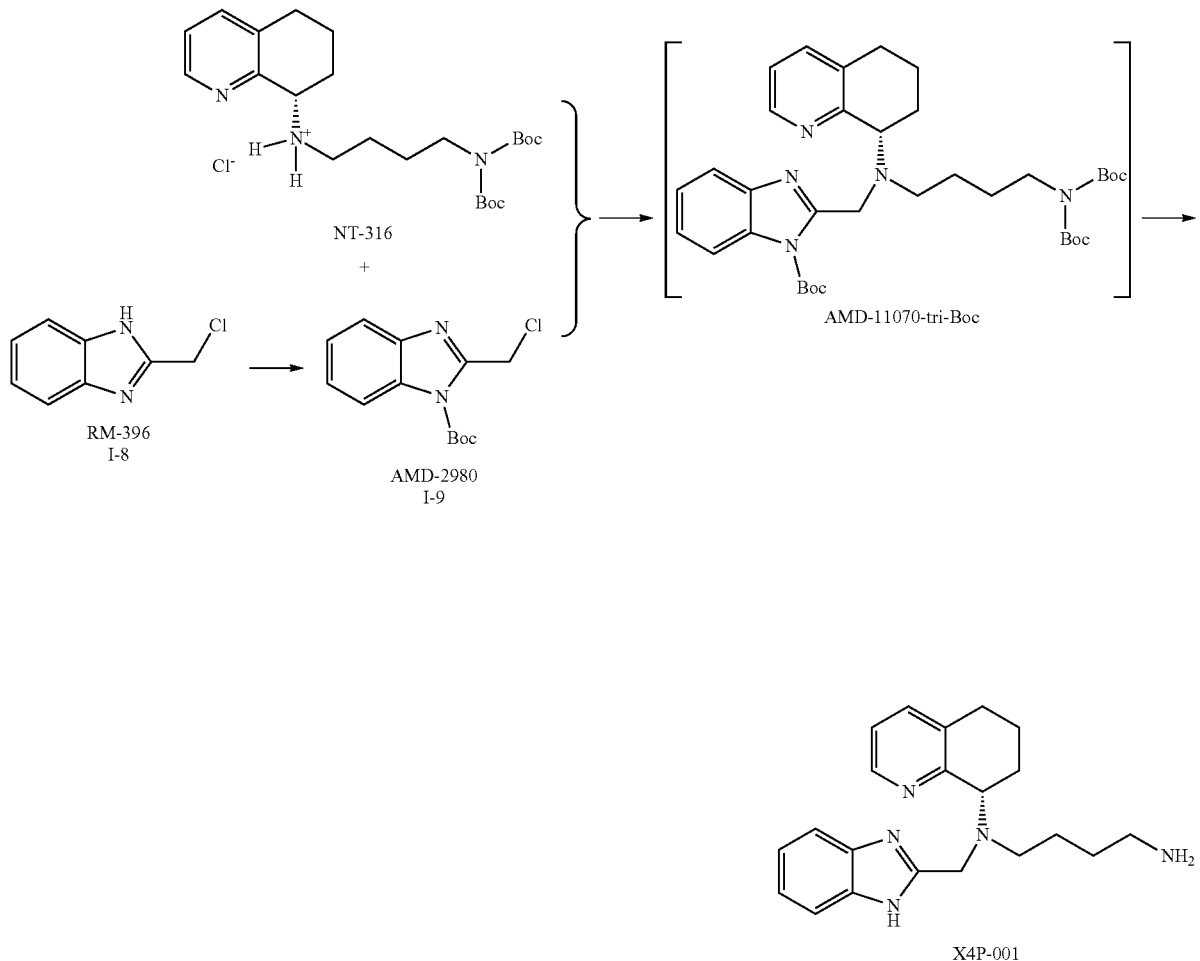

Scheme 8 Late steps in the synthesis of X4P-001.

Key fragment AMD-2890 is synthesized in one step from RM-396 (I-8). Even though RM-396 is commercially available, its purity is highly variable depending on its source. The purity of commercially sourced material can appear to be high (>97 area %) according to HPLC analysis, however the true wt % purity has been found to be as low as 90%. It is likely that RM-396 undergoes self-alkylation, resulting in the formation of a variable mixture of oligomeric impurities. Only after conversion of RM-396 into AMD-2890 is a stable compound with a well-defined impurity profile obtained.

The other key fragment is NT-316, a stable, crystalline and well-characterized compound that incorporates a significant part of the API structure. NT-316 is obtained by a convergent synthesis via reaction of NT-319 with the chiral amine salt NT-272. NT-272 is a stable crystalline compound, which can be procured via custom synthesis.

NT-319 is a highly unstable intermediate which cannot be isolated without degradation. It is prepared in 3 steps (each without isolation of intermediates) from commercial ABA. Control of the purity of ABA is difficult because it is not only an oil, but it also lacks a UV chromophore, severely limiting the methods for its precise analytical characterization.

On the basis of the above, it is the impurity profile of these two fragments NT-316 and AMD-2890 (I-9), in combination with the exact conditions of the two final chemical steps (which are to be conducted under GMP control), that determine the impurity profile and quality of the API.

In summary, the chemical and enantiomeric purity of NT-316 and the chemical purity of AMD-2890 can be directly correlated with the chemical and enantiomeric purity of the API (X4P-001).

Description of Key Process Changes

Figure 3:
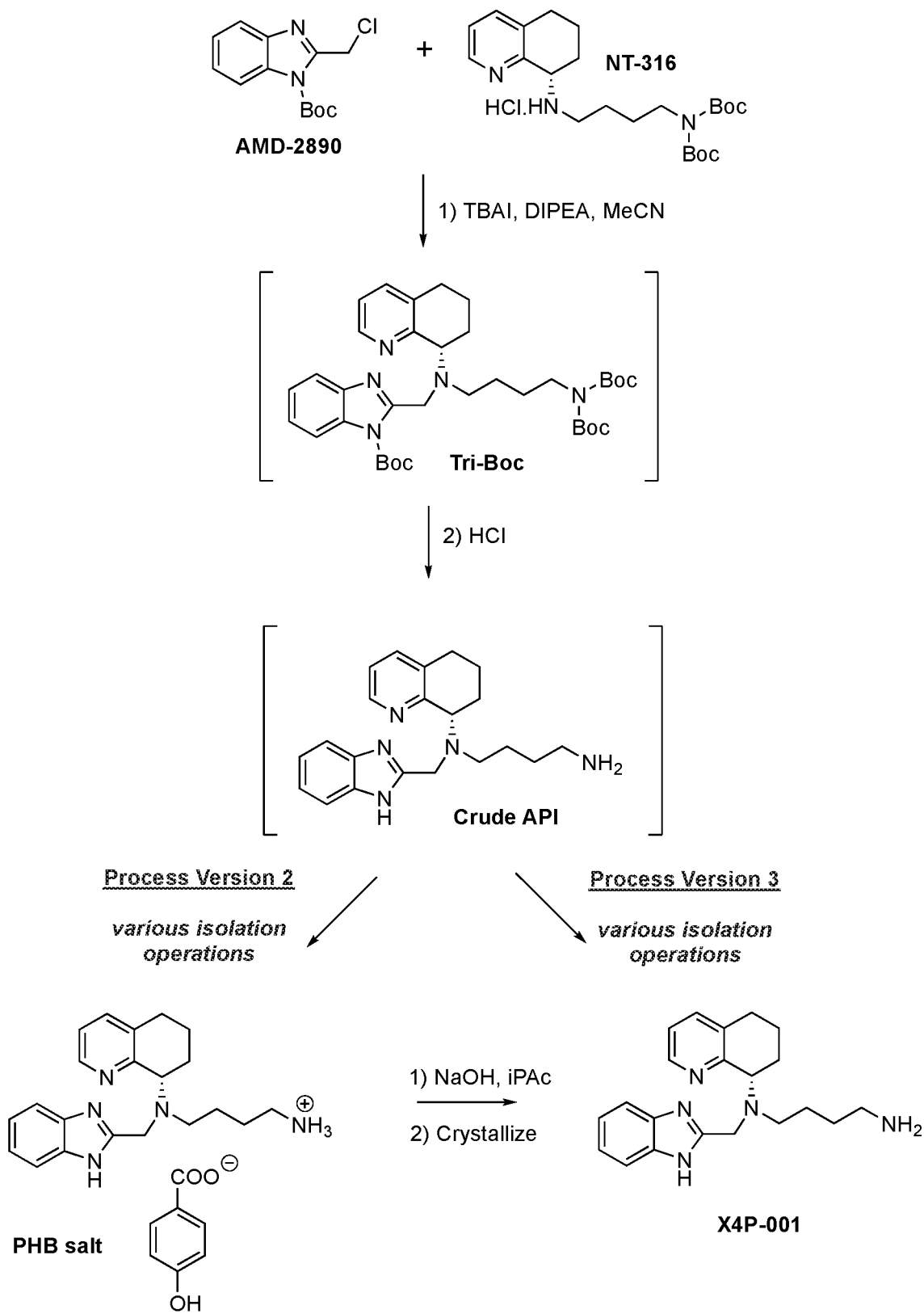
FIG. 3 shows a comparison of Process 3 (the current, improved synthesis) and Process 2 (the original process) for the preparation of X4P-001.

FIG. 3 shows how the new process (Process 3) differs from the previous version (Process 2). In process version 2, it proved necessary to isolate the API first as its 4-hydroxybenzoate salt. This salt was then converted to the corresponding free base in a separate step in order to obtain the API.

The chemical steps in process version 3 are unchanged. Compounds NT-316 and AMD-2890 (I-9) are reacted with each other and the resulting product (Tri-Boc), which is not isolated but rather deprotected immediately to afford the crude API. However, the method utilized for isolating the API has changed considerably in process version 3.

Among the most significant impurities that are produced in process version 2 are imine A (RRT 1.08) and N-formyl B (RRT 1.28), as shown in Scheme 9. It was shown that these impurities originated from the use of dichloromethane as a solvent during the extractions of the crude API. Furthermore, formation of acetamide impurity C (RRT 1.37) could be correlated with the use of isopropyl acetate as the solvent for the final crystallization of the API free base.

Scheme 9 Impurities Discovered in the Bulk Drug Substance

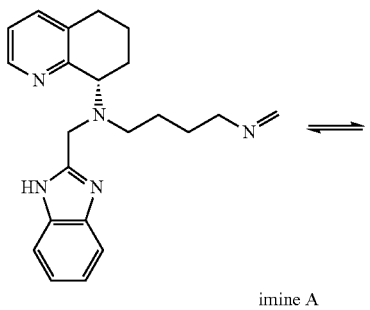

imine A

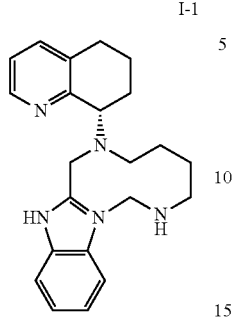

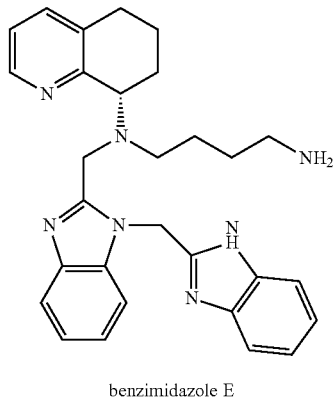

benzimidazole E

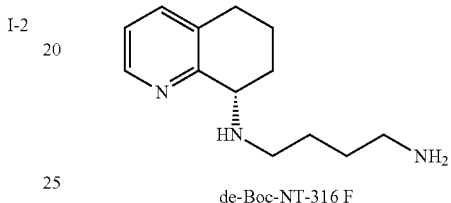

de-Boc-NT-316 F

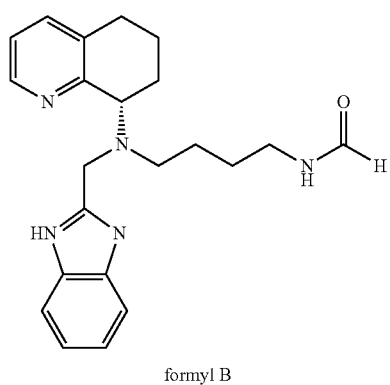

formyl B

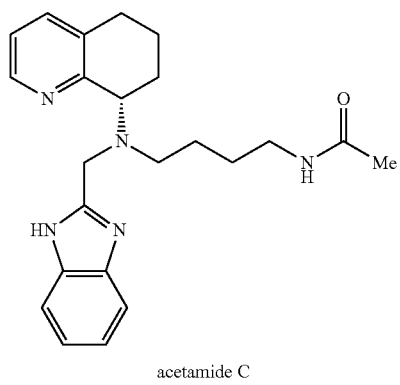

acetamide C

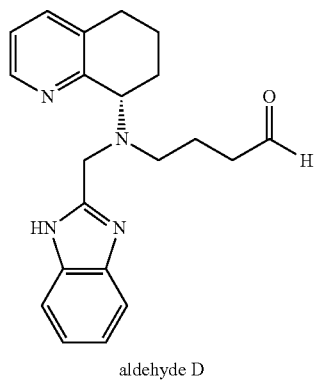

aldehyde D

Thus, dichloromethane and isopropyl acetate, which were used in the work-up and isolation of X4P-001 in version 2, were replaced with 1-butanol and a toluene/methanol mixture, respectively, for version 3. We have found that these solvents do not react with the API, and accordingly we believe that this change has caused the significant reduction of impurities A (imine), B (N-formyl) and C (acetamide) that we have observed.

In addition, it was found that problems with formation of gums and oiling of the API during the final product crystallization in process version 2 were due to the quality of the AMD-2890 starting material. This material is obtained from the commercial 2-chloromethylbenzimidazole (RM-396), which can have a low wt % purity even when the area % purity appears to be good (>98%). The development of an improved isolation procedure for AMD-2890 is an integral part of process version 3 and this has consistently resulted in the production of high quality AMD-2890, which possesses not only excellent % purity but also assay % w/w purity.

Further optimization of the aeration and carbon treatments during the isolation of the API has resulted in better control over the color of the isolated API and these operations are also included in process version 3.

Finally, the crystallization of the free base API from toluene was narrowly defined. The meta-stable zone and the optimum seeding point were determined. We also developed an optimum cooling rate after formation of the seed bed, as well as an appropriate washing and drying protocol.

Figure 4:
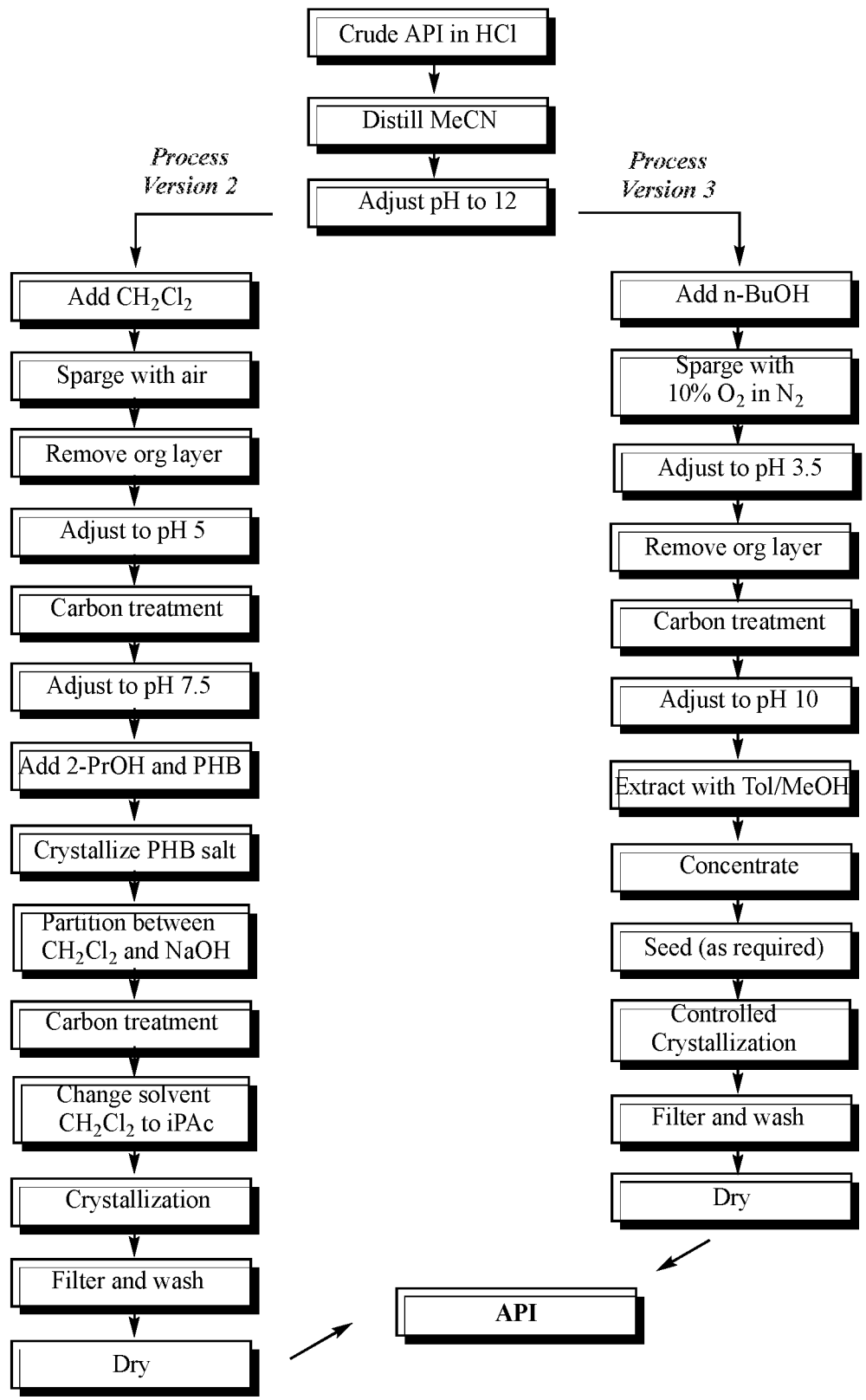
FIG. 4 shows a detailed comparison between Process version 2 and 3 for the consecutive downstream operations in the work-up and isolation of the API.

FIG. 4 provides a detailed comparison between Process version 2 and 3 for the consecutive downstream operations in the work-up and isolation of the API.

The robustness and reproducibility of the process version 3 was demonstrated through the performance of three identical lab experiments on 100 g scale. As the data in Table 3 and Table 4 show, this process demonstration was successful. We subsequently scaled up the process to a 10 kg scale. A total of 9.75 kg of GMP X4P-001 was prepared in a single batch with nearly identical outcomes. The details of these experiments are discussed below.

Description of Process Version 3 and Improvements of Process 1 and Process 2

The following section provides a brief description of the various operations in the synthesis and isolation of the API in the final step of process version 3.

Synthesis of NT-316

The early process steps for the preparation of the key starting material NT-316 from the custom synthesized chiral amine NT-272 and ABA are unchanged from earlier campaigns.

Synthesis of AMD-2890

As noted above, the synthesis AMD-2890 (I-9) has been improved, in particular its isolation and crystallization, to accommodate for the variable purity and color of commercial 2-chloromethylbenzimidazole (RM-396). This material is typically dark brown to black. A charcoal treatment was therefore introduced to allow better control of the color of AMD-2890.

Thus, 2-chloromethylbenzimidazole (RM-396) is reacted with 1.3 equiv. of di-tert-butyl dicarbonate in DMF (N,N-dimethylformamide) 8.6 volumes (vol) at 40° C. in the presence of 0.1 equivalent (equiv.) of DIPEA (diisopropylethylamine). After completion of the reaction decolorizing charcoal is added. After aging for 1.5 h at 40° C. the mixture is filtered, and the solids washed with 1 vol of DMF. Water (3.5 vol) is added slowly to the filtrates, resulting in a slightly turbid mixture which is seeded with 1% of AMD-2890. Upon aging, a slurry is produced which is allowed to cool slowly to 20° C. After slow addition of more water (1 vol) and further cooling to 0° C. the slurry is filtered. The solids are first washed with a 2:1 mixture of DMF and water, then with water (2×3 vol), all at 0° C. The filter cake is dried under a stream of nitrogen providing the light-yellow AMD-2890. This compound is typically >99 area % (by HPLC) and >99 wt % (by NMR) pure.

Synthesis and Isolation of X4P-001

As before, equimolar quantities of NT-316 and AMD-2890 are reacted in the presence of diisopropylethylamine (DIPEA) and tetrabutylammonium iodide (TBAI) in acetonitrile at 60-65° C. Once complete, the reaction is cooled to ambient temperature and quenched with 0.3 vol of ammonia before 1 vol of water is added. The resulting mixture is then added to mixture of 2 vol of concentrated hydrochloric acid and 3 vol of water. Aging for several hours at 35-40° C. in this acidic solution effects the deprotection of the protected intermediate to the API. The acetonitrile is subsequently removed via a vacuum distillation.

At this point, 2 vol of 1-butanol are added and the pH is adjusted to 12 with 20% NaOH solution. The resulting biphasic mixture is sparged with a mixture of 10% of oxygen in nitrogen for 2 h at 20° C. The pH is subsequently adjusted to 3.0-3.5 with a solution of 18% HCl in water. The resulting two phases are separated, and the aqueous layer is washed with 1-butanol (3×3 vol). The organic layers are combined and extracted with 3 vol of water. All aqueous phases are then combined and 0.4% (wt) of carbon is added. After 1-2 h the mixture is filtered, and the solids washed with 3 vol of water.

Toluene (7 vol) and methanol (1 vol) are added to the combined filtrates and the temperature is increased to 45-55° C. before the pH is adjusted to 9.5-10.0 with 20% sodium hydroxide solution. The phases are separated, and the aqueous layers is extracted twice more with 3 vol of toluene.

All toluene layers are combined and partially concentrated via vacuum distillation at 45-50° C. After several additions of fresh toluene and continued vacuum distillation at 45-50° C. to remove other volatile solvents a solution of the API in approximately 3 vol of toluene is obtained. This solution is heated to 60° C. and cleared via line filtration.

Upon cooling to 50° C. this solution is carefully seeded with up to 0.5 wt % of X4P-001. After a seedbed develops a steady crystallization of the API is allowed to occur over 2-3 h before the slurry is allowed to cool slowly to 0° C. The resulting slurry is gradually warmed back to 30-35° C. and then allowed to cool back to 0° C. to promote crystal growth. At the end the slurry is filtered, and the final solids are washed with toluene and dried in a filter dryer via heating under vacuum at 60° C. for 16 h, with occasional careful agitation.

This procedure has been demonstrated on 10 kg scale which provided X4P-001 with 99.0-99.5 area % purity (>99.9% enantiopurity) and 1337 ppm of residual toluene.

Comparison of Process 2 and Process 3

Table 3 provides a comparison of key process parameters and outcomes for batches produced most recently with Process 2 and 3. As mentioned above, process version 3 was first demonstrated on lab scale and subsequently scaled up in the plant for production of X4P-001. Table 4 provides a comparison of the impurity profiles of these batches.

Most importantly, Table 4 shows that a switch from process version 2 to process version 3 has consistently resulted in an overall 0.5-1.1 area % reduction in total impurities as well as a significant reduction in total residual solvents in the API with no adverse impacts on other critical process outcomes.

TABLE 3

Comparison of Key Process Parameters and Outcomes of Batches Produced with Process Versions 2 and 3.

| | 3-1 | | 3-2 | | 3-3 | | 3-4 | | 3-5 | | 3-6 | |
|---|---|---|---|---|---|---|---|---|---|---|---|---|
| Process version | 2 | | 2 | | 3 | | 3 | | 3 | | 3 | |
| Appearance | Pale yellow solid | | Pale yellow solid | | Pale yellow solid | | Pale yellow solid | | Pale yellow solid | | Pale yellow solid | |
| Chiral purity | >99% | | >99% | | >99.9% | | >99.9% | | >99.9% | | >99.9% | |
| Heavy metals | <20 ppm | | <20 ppm | | <5 ppm | | <5 ppm | | <5 ppm | | Not performed | |
| Residual solvents | iPAc | 4148 ppm | iPAc | 7440 ppm | iPAc | ND | iPAc | ND | iPAc | ND | iPAc | ND |
| (by GC) | DCM | 8 ppm | DCM | ND | DCM | ND | DCM | ND | DCM | ND | DCM | ND |
| | IPA | 6 ppm | IPA | 52 ppm | IPA | 65 ppm | IPA | ND | IPA | 109 ppm | IPA | ND |
| | Tol | ND | Tol | ND | Tol | 2020 ppm | Tol | 3022 ppm | Tol | 2020 ppm | Tol | 1337 ppm |

TABLE 3-continued

Comparison of Key Process Parameters and Outcomes of Batches Produced with Process Versions 2 and 3.

| | Batch number | | | | | |
|---|---|---|---|---|---|---|
| | 3-1 | 3-2 | 3-3 | 3-4 | 3-5 | 3-6 |
| Moisture (by KF) | <0.1 wt % | 0.2 wt % | 0.2 wt % | 0.2 wt % | 0.3 wt % | 0.2 wt % |
| PSD (by laser diffraction) | D(50) 140 μm | D(50) 118 μm | D(50) 91 μm | D(50) 169 μm | D(50) 122 μm | D(50) 48 μm |

ND = Not detected;
iPAc = isopropyl acetate;
DCM = dichloromethane;
IPA = isopropyl alcohol;
Tol = toluene.

TABLE 4

Comparison of HPLC Impurity Profile of Batches Produced with Process Version 2 and 3.

| | Batch number | | | | | |
|---|---|---|---|---|---|---|
| | 3-1 | 3-2 | 3-3 | 3-4 | 3-5 | 3-6 |
| Process version | 2 | 2 | 3 | 3 | 3 | 3 |
| Assay (wt %, oab) | 99.3 | 97.9 | 99.9 | 96.7 | 97.8 | 98.4 |
| Purity (%) | 98.8 | 98.3 | 99.46 | 99.40 | 99.28 | 99.51 |
| Identified impurities (%) | | | | | | |
| RRT 0.38 (de-Boc NT-316) (I-7) | ND | ND | 0.11 | 0.09 | 0.13 | 0.05 |
| RRT 1.08 (imine) (I-1) | 0.62 | 0.95 | 0.10 | 0.13 | 0.04 | 0.09 |
| RRT 1.21 (aldehyde) (I-6) | NT* | NT* | 0.09 | 0.14 | 0.20 | 0.14 |
| RRT 1.28 (formyl) (I-2) | 0.03 | ND | 0.03 | 0.03 | 0.03 | 0.05 |
| RRT 1.37 (acetamide) (I-5) | 0.07 | 0.42 | 0.02 | 0.04 | 0.06 | ND |
| RRT 1.93 (benzimidazole) (I-3) | 0.01 | ND | 0.06 | 0.05 | 0.04 | 0.04 |
| Total impurities (%) | 1.20 | 1.67 | 0.54 | 0.60 | 0.72 | 0.49 |

ND = Not detected.
NT = Not tested.
*For these two batches, it is unknown whether any aldehyde impurity was present in these batches.

Improvements in Residual Solvent Levels in Process 3

During early clinical development of X4P-001 (formerly AMD110170), the drug substance was directly isolated as the freebase using ethyl acetate as a crystallization solvent (Process 1). However, difficulties were encountered in removing the ethyl acetate from the final API, with development lots requiring laborious efforts, including grinding and exposure to hot nitrogen, in order to reduce the levels below the International Conference on Harmonisation (ICH) limit of NMT 5000 ppm. During development of AMD-110170, early efforts also employed isopropyl acetate in several batches of API as the isolation solvent in Process 1.

Later in development, the parahydroxybenzoate (PHB) salt of AMD-11070 was isolated as an intermediate, followed by conversion to the freebase (Process 2). We have used this process to manufacture drug substance for recent clinical trials. In Process 2, the freebase was isolated following salt release using isopropyl acetate instead of ethyl acetate. This API displayed similarly high levels of residual solvents as seen in API made via Process 1. Additionally, we have found that isopropyl acetate has been implicated in the generation of the acetamide impurity during production. Therefore, a change in the final API isolation solvent was warranted.

Our recent process development has afforded a direct free base isolation procedure (PHB salt is no longer an intermediate in the process) which now employs toluene instead of isopropyl acetate as the final crystallization solvent (Process 3). We found that toluene does not react with X4P-001, and therefore provides a more appropriate solvent for isolation. As noted above, eliminating use of isopropyl acetate also leads to a reduction in impurity levels. A summary of residual solvent levels in batches of X4P-001, and their residual crystallization solvent levels, is presented in Table 5.

TABLE 5

Residual Isolation Solvent Levels for X4P-001 During Development

| Isolation Solvent | Measured Levels (ppm) |
|---|---|
| Process #1 | |
| Ethyl or Isopropyl acetate | 7219 |
| Ethyl or Isopropyl acetate | 9108 |
| Ethyl or Isopropyl acetate | 1971 |
| Ethyl or Isopropyl acetate | 6820 |
| Ethyl or Isopropyl acetate | 9298 |
| Process #2 | |
| Isopropyl acetate | 2500 |
| Isopropyl acetate** | 4148** |
| Isopropyl acetate | 7440 |
| Isopropyl acetate & Toluene* | ND (iPAc)* |
| | 2280 (Toluene)* |
| Process #3 | |
| Toluene | 4487 |
| Toluene | 2020 |
| Toluene | 3022 |
| Toluene | 2020 |
| Toluene | 1337 |

*API batch was reworked from a batch originally crystallized using isopropyl acetate, using toluene at the final crystallization stage, therefore this lot was assayed for both isopropyl acetate (iPAc) and toluene.
**Batch 3-1.

Historically, batches of X4P-001 have shown average residual solvent levels of the primary crystallization solvent in the range of 1971 ppm to 9298 ppm. We have employed the PDE approach to set a specification for residual toluene in X4P-001 freebase.

Assuming a dose of 600 mg X4P-001 per day (a 50% safety margin over an exemplary clinical dose of 400 mg per day), the calculated levels of toluene in X4P-001 API would be not more than 4500 ppm. Therefore, in certain embodiments of the present invention, the specification for residual toluene in X4P-001 is not more than 4500 ppm. Accordingly, in some embodiments, the present invention provides an X4P-001 composition comprising no more than 4500 ppm of toluene or 1350 ppm of toluene.

85

Conclusions

Taken together, the above improvements in Process version 3 have resulted in a more robust and reproducible final process step when compared with version 2. Most importantly, the purity of the isolated API X4P-001 has significantly improved when compared with the previous process version. Importantly, we have discovered that the choice of solvents in the work-up and isolation of X4P-001 is key to the improved impurity profile described above. Specifically, we have replaced dichloromethane and isopropyl acetate, which were used in the work-up and isolation of X4P-001 in Process version 2, with 1-butanol and a toluene/methanol mixture, respectively, in Process version 3. We have found that, in batches produced using Process version 2, certain of the impurities are present in increased amounts in the final product due to the API, X4P-001, reacting with dichloromethane and isopropyl acetate. Another key discovery was that the formation of gums and oiling of the API during the final product crystallization in process version 2 were due to the variable (and often poor) quality of the AMD-2890 starting material. As described above, we have introduced an improved isolation procedure for AMD-2890 that consistently produces high quality AMD-2890 and avoids the formation of gums and oiling of the API.

Example 10: Mutagenicity Evaluation

We have performed a Mutagenic Risk Assessment on the synthetic process to generate X4P-001, all process intermediates, potential and actual impurities. The assessment included review of all raw materials, including key starting materials, as well as the potential and actual process impurities and degradation products. All assessments were carried out in accordance with ICH M7(R1) guidance.

Scheme 10 and Scheme 11 below depict the synthetic Process 2 and Process 3, respectively, for X4P-001. Scheme 12 depicts the synthesis of NT-319 and AMD-2890 process intermediates.

Table 6 below depicts the identified potentially mutagenic impurities in the process for manufacturing X4P-001.

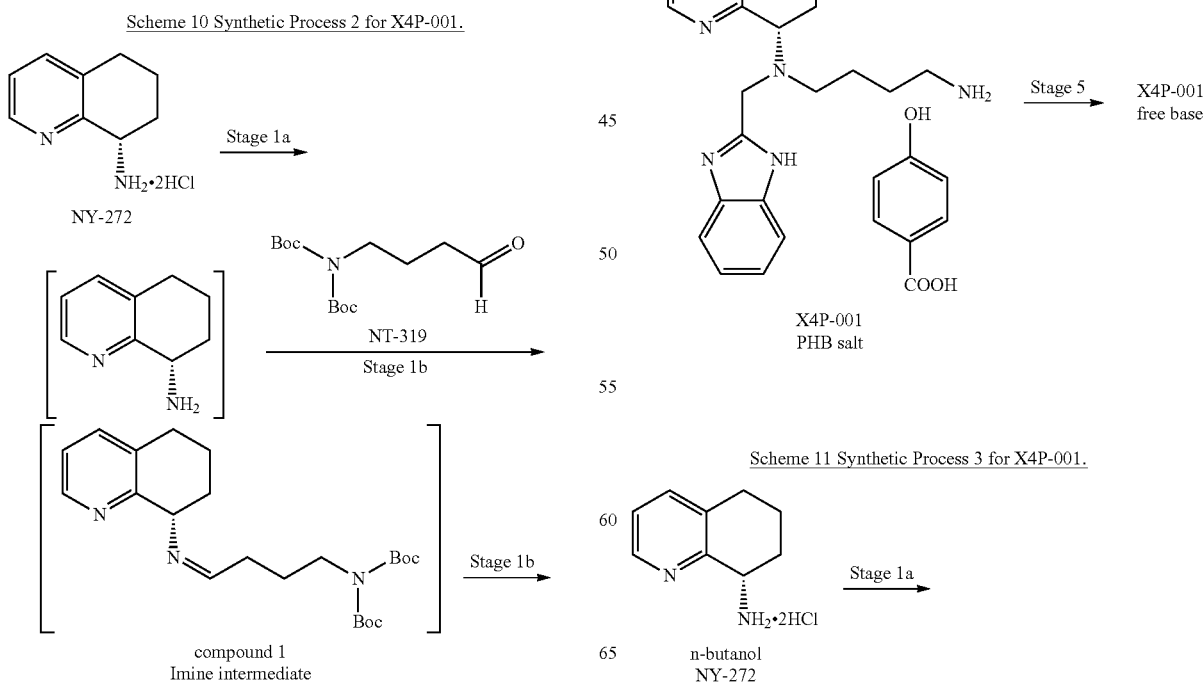

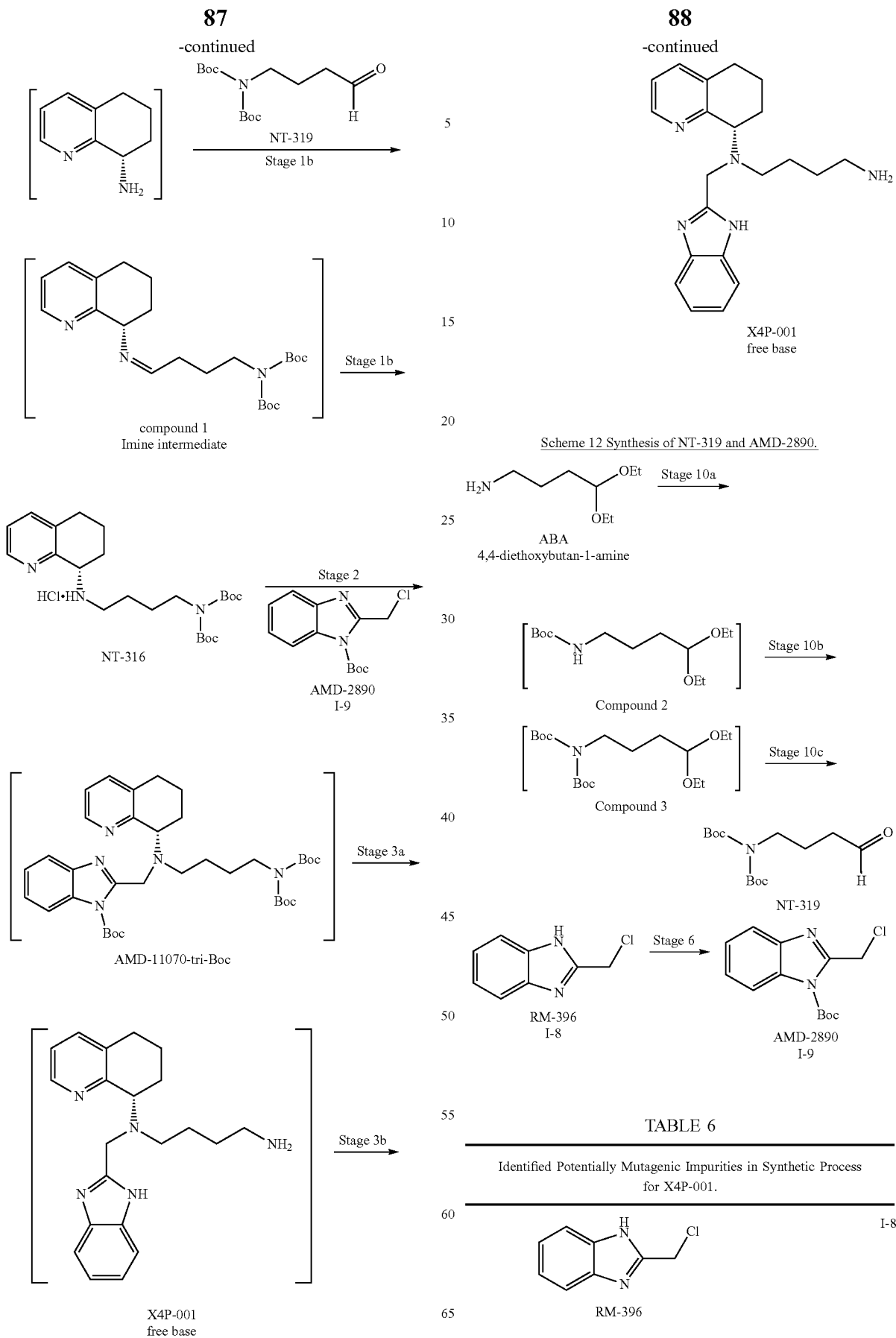

TABLE 6-continued

Identified Potentially Mutagenic Impurities in Synthetic Process for X4P-001.

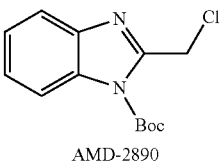 [SMILES: CC(C)(C)OC(=O)n1c(CCl)nc2ccccc21]

AMD-2890   I-9

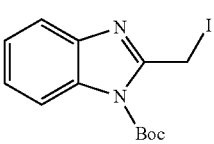 [SMILES: CC(C)(C)OC(=O)n1c(CI)nc2ccccc21]

I-10

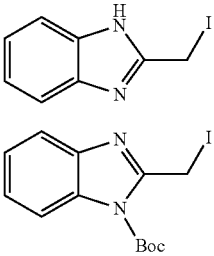

I-11

The expected duration of treatment for patients in clinical trials is less than 10 years. The acceptable intake of a drug with an exposure of >1 to 10 years is 10 μg/day of a mutagenic impurity, based on Table 2 in ICH M7(R1).

Based on a 400 mg/day dose of X4P-001, a limit of up to 25 ppm of a potentially mutagenic impurity is acceptable (10 μg/day/400 mg=25 ppm (μg/g)).

The potential impurities I-10 and I-11 have never been detected in X4P-001. Additionally, a theroretical purge factor calculation on synthetic process 3, based on published references such as by Teasdale et al., (Org. Process Res. Dev. 2013, 17, 221), showed that the process efficiently purges both potential impurities I-10 and I-11 with a theoretical purge factor of about $9 \times 10^8$ (I-10) and about $9 \times 10^{10}$ (I-11).

Based on the calculated purge factors, a theoretical residual amount of I-10 and I-11 of about <0.0001 ppm I-10 and about <0.000001 ppm I-11 in X4P-001 has been calculated, which shows that both potentially mutagenic impurities are efficiently purged with this process and no control in X4P-001 is required.

The potential impurities RM-396 and AMD-2890 (I-9) have never been detected (limit of quantitation, or LOQ, 2.5 ppm) in X4P-001, which shows that both potentially mutagenic impurities are efficiently purged with this process.

Example 11: 25 mg, 100 mg, and 200 mg Solid Formulations

During formulation development, the excipients were chosen based on screening studies involving short term compatibility of various excipients. Microcrystalline cellulose was chosen as a diluent/filler for 25 mg and lower strength capsules. Dibasic calcium phosphate dihydrate diluent/filler was added to the formulation to improve flowability for the 100 mg higher strength formulation. The ratio of microcrystalline cellulose to dibasic calcium phosphate dihydrate was chosen to approximate the bulk density of drug substance to reduce the probability of segregation during mixing. Sodium stearyl fumarate was chosen as a lubricant. To facilitate the capsule filling on an automated capsule filler, the glidant colloidal silicon dioxide was added to the formulation as a flow aid. Croscarmelose sodium was selected as a disintegrant to enable automated capsule filling. Sodium lauryl sulfate was added to the formulation to reduce sticking of drug substance during encapsulation and as a wetting agent.

TABLE 7

Composition of Exemplary X4P-001 25 mg Capsules

| Component | Reference to Standard | Function | Quantity (mg/capsule) | % w/w |
|---|---|---|---|---|
| X4P-001 composition | In House | Active Ingredient | 25.0 | 14.7 |
| Microcrystalline Cellulose | NF | Diluent | 132.7 | 78.1 |
| Croscarmellose Sodium | NF | Disintegrant | 10.2 | 6.0 |
| Sodium Stearyl Fumarate | NF | Lubricant | 1.7 | 1.0 |
| Colloidal Silicon Dioxide | USP | Flow Aid | 0.4 | 0.2 |
| Sum Total | | | 170.0 | 100.0 |
| Hard Gelatin Capsules, Size 1 | USP | Packaging | NA | NA |

TABLE 8

Composition of X4P-001 100 mg Capsules

| | | | 100 mg | |
| Component | Reference to Standard | Function | Quantity (mg/capsule) | w/w |
|---|---|---|---|---|
| X4P-001 composition | In House | Active substance | 100.0 | 37.6% |
| Dibasic Calcium Phosphate Dihydrate | USP/NF | Diluent | 84.3 | 31.7% |
| Microcrystalline Cellulose | NF/EP | Diluent | 60.9 | 22.9% |
| Croscarmellose Sodium | NF/EP | Disintegrant | 16.0 | 6.0% |
| Sodium Stearyl Fumarate | NF | Lubricant | 2.7 | 1.0% |
| Sodium Lauryl Sulfate | NF/EP | Wetting agent | 1.3 | 0.5% |
| Colloidal Silicon Dioxide | NF/EP | Flow Aid | 0.8 | 0.3% |
| Sum | | | 266.0 | 100% |
| Hard gelatin capsules, Size 1 white/white. Qualitative composition: Gelatin and Titanium dioxide. | USP | Encapsulation | N/A | N/A |

TABLE 9

Composition of X4P-001 200 mg Capsules

| | 200 mg | |
| Ingredients | Percent Per Capsule (%) | Theoretical Amount Per Capsule (mg) |
|---|---|---|
| X4P-001 composition | 61.5 | 200.0 |
| Microcrystalline Cellulose, NF/EP (Avicel PH 101) or equivalent | 12.9 | 41.93 |
| Dibasic Calcium Phosphate Dihydrate, USP/NF | 17.8 | 57.85 |
| Croscarmellose Sodium, NF/EP (Ac-Di-Sol) | 6.0 | 19.50 |

TABLE 9-continued

Composition of X4P-001 200 mg Capsules

| Ingredients | 200 mg | |
|---|---|---|
| | Percent Per Capsule (%) | Theoretical Amount Per Capsule (mg) |
| Sodium Lauryl Sulfate, NF/Ph. Eur. | 0.5 | 1.625 |
| Colloidal Silicone Dioxide, NF/Ph. Eur. (Cab-O-Sil M-5P) | 0.3 | 0.9750 |
| Sodium Stearyl Fumarate, NF (Pruv) | 1.0 | 3.250 |
| Total Capsule Fill | 100 | 325.0 |

The compatibility of excipients has been shown through ongoing long-term stability studies of the drug product where the product meets stability requirements for the specified refrigerated storage conditions for 3 lots of 100 mg capsules. Up to 24-month stability results are available for X4P-001 100 mg capsule lot 15K227 packaged in 30 count amber glass bottles and sealed in aluminum foil bags at the storage conditions of 5° C.±3° C. and 25° C./60% RH. At the recommended storage condition of 5° C.±3° C., the results show no significant trends in any stability test parameter up to 24-months (assay, impurities, dissolution, moisture, and microbial testing).

Up to 9 months of stability results for 100 mg capsules stored at 5° C.±3° C. and packaged in amber glass bottles sealed in aluminum foil bags or Oxy-Guard HDPE bottles showed an increase in the imine impurity over time, but well within specification. No trends from initial values in any of the other stability test parameters were observed.

Up to 3-month stability results for 100 mg capsules stored at 5° C.±3° C. and 25° C./60% RH and packaged in Oxy-Guard HDPE bottles showed an increase in the imine impurity over time, but well within specification. No trends from initial values in any of the other stability test parameters were observed. These capsules were produced with X4P-001 drug substance manufactured using a toluene rework procedure.

The continued use of refrigerated cold chain storage is an anticipated requirement for X4P-001 drug product. The X4P-001 drug product primary container packaging to be used in phase 3 clinical trials is the Oxy-Guard 60 cc HDPE bottle with 33 mm cap with induction seal. Rayon coil is placed above the capsules in each bottle and one desiccant pack (0.5 g Sorb-It or equivalent) is positioned at the top of each bottle between the Rayon coil and cap (30 count).

A detailed summary of the manufacturing process is provided in FIG. 1.

I claim:

1. An X4P-001 composition comprising a compound of formula I:

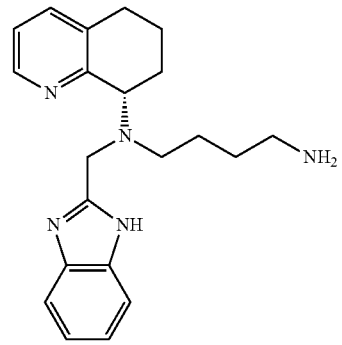

or a pharmaceutically acceptable salt thereof; and a compound of formula I-6:

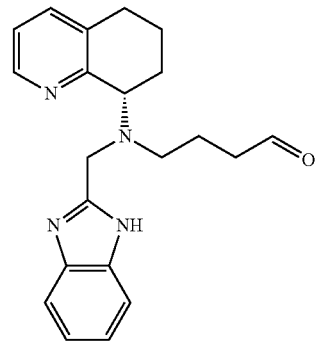

or a pharmaceutically acceptable salt thereof; and wherein the compound of formula I-6 is present in an amount less than about 0.3% w/w of the X4P-001 composition.

2. The X4P-001 composition of claim 1, wherein the compound of formula I-6 is present in an amount less than about 0.2% w/w of the X4P-001 composition.

3. The X4P-001 composition of claim 1, wherein the compound of formula I-6 is present in an amount less than about 0.1% w/w of the X4P-001 composition.

4. The X4P-001 composition of claim 1, wherein the X4P-001 composition further comprises one or more of the following compounds:

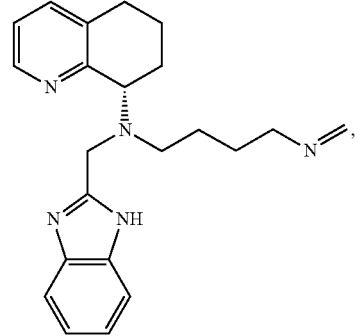

-continued

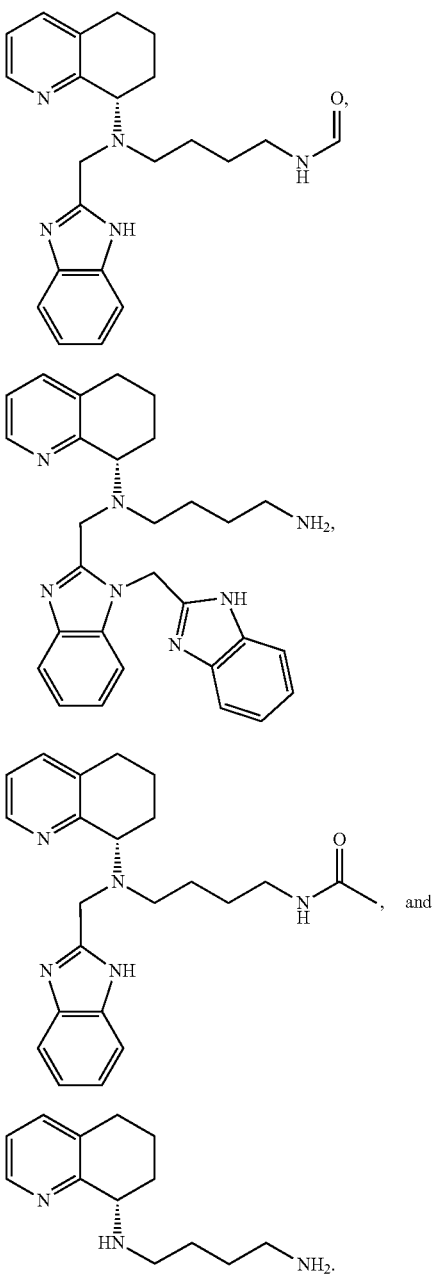

5. The X4P-001 composition of claim 4, wherein the X4P-001 composition comprises less than 0.7% w/w total of I-1, I-2, I-3, I-5, I-6, and I-7.

6. The X4P-001 composition of claim 1, wherein the amount of I-6, or a pharmaceutically acceptable salt thereof, is from about 0.01 to about 0.3% w/w of the X4P-001 composition; and wherein the X4P-001 composition comprises no more than 3.0% total impurities.

7. The X4P-001 composition of claim 1, wherein the amount of I-6, or a pharmaceutically acceptable salt thereof, is from 0.01 to 0.3% w/w of the X4P-001 composition; and wherein the total the total weight of I-6 and any additional impurities that are present comprise no more than 0.8% w/w of the X4P-composition.

8. The X4P-001 composition of claim 7, wherein the compound of formula I is present in the X4P-001 composition as a free base.

9. The X4P-001 composition of claim 8, wherein the X4P-001 composition comprises no more than 0.7% w/w total impurities.

10. The X4P-001 composition of claim 9, wherein the R-enantiomeric excess (% ee) of the compound of formula I is no less than 97.0%.

11. The X4P-001 composition of claim 10, wherein the X4P-001 composition comprises no more than 0.2% total organic impurities as an area percent (measured by HPLC) relative to the total area of an HPLC chromatogram.

12. A pharmaceutical composition comprising the X4P-001 composition of claim 1, and a pharmaceutically acceptable adjuvant, carrier, or vehicle.

13. A unit dosage form comprising the pharmaceutical composition of claim 12, wherein the X4P-001 composition is present in an amount of about 100 mg.

14. A pharmaceutical composition comprising the X4P-001 composition of claim 3, and a pharmaceutically acceptable adjuvant, carrier, or vehicle.

15. A unit dosage form comprising the pharmaceutical composition of claim 14, wherein the X4P-001 composition is present in an amount of about 100 mg.

16. A pharmaceutical composition comprising the X4P-001 composition of claim 5, and a pharmaceutically acceptable adjuvant, carrier, or vehicle.

17. A pharmaceutical composition comprising the X4P-001 composition of claim 10, and a pharmaceutically acceptable adjuvant, carrier, or vehicle.

18. A unit dosage form comprising the pharmaceutical composition of claim 16, wherein the X4P-001 composition is present in an amount of about 100 mg.

* * * * *

UNITED STATES PATENT AND TRADEMARK OFFICE
CERTIFICATE OF CORRECTION

| | | |
|---|---|---|
| PATENT NO. | : 12,115,156 B2 | Page 1 of 1 |
| APPLICATION NO. | : 18/312484 | |
| DATED | : October 15, 2024 | |
| INVENTOR(S) | : Karel Marie Joseph Brands | |

It is certified that error appears in the above-identified patent and that said Letters Patent is hereby corrected as shown below:

In the Claims

At Column 94, Claim number 7, Line number 12: Please replace the text:
"the total the total"

With:
--the total--.

Signed and Sealed this
Tenth Day of December, 2024

Katherine Kelly Vidal
*Director of the United States Patent and Trademark Office*